United States Patent
Zhang et al.

(10) Patent No.: US 12,338,206 B2
(45) Date of Patent: Jun. 24, 2025

(54) COMPOUNDS AND THEIR USES AS THYROID HORMONE RECEPTOR AGONISTS

(71) Applicant: Nanjing Ruijie Pharma Co., Ltd., Nanjing (CN)

(72) Inventors: Junbo Zhang, Nanjing (CN); Xiaoxin Qi, Nanjing (CN)

(73) Assignee: Nanjing Ruijie Pharma Co., Ltd., Jiangsu (CN)

( * ) Notice: Subject to any disclaimer, the term of this patent is extended or adjusted under 35 U.S.C. 154(b) by 936 days.

(21) Appl. No.: 17/432,089

(22) PCT Filed: Feb. 20, 2020

(86) PCT No.: PCT/CN2020/076038
§ 371 (c)(1),
(2) Date: Aug. 18, 2021

(87) PCT Pub. No.: WO2020/169069
PCT Pub. Date: Aug. 27, 2020

(65) Prior Publication Data
US 2022/0162161 A1    May 26, 2022

(51) Int. Cl.
| | |
|---|---|
| *C07D 403/10* | (2006.01) |
| *C07C 311/03* | (2006.01) |
| *C07D 261/12* | (2006.01) |
| *C07D 401/10* | (2006.01) |
| *C07D 401/12* | (2006.01) |
| *C07D 403/12* | (2006.01) |
| *C07D 413/12* | (2006.01) |
| *C07D 471/04* | (2006.01) |

(52) U.S. Cl.
CPC .......... *C07C 311/03* (2013.01); *C07D 261/12* (2013.01); *C07D 401/10* (2013.01); *C07D 401/12* (2013.01); *C07D 403/10* (2013.01); *C07D 403/12* (2013.01); *C07D 413/12* (2013.01); *C07D 471/04* (2013.01)

(58) Field of Classification Search
CPC .. C07D 403/10; C07D 261/12; C07D 401/10; C07C 311/03
See application file for complete search history.

(56) References Cited

U.S. PATENT DOCUMENTS

| | | |
|---|---|---|
| 5,141,938 A | 8/1992 | Lindner et al. |
| 6,787,652 B1 | 9/2004 | Dow et al. |
| 2012/0129512 A1 | 5/2012 | Kanai et al. |
| 2012/0129812 A1 | 5/2012 | Kawata et al. |

FOREIGN PATENT DOCUMENTS

| | | |
|---|---|---|
| CN | 101228135 A | 7/2008 |
| CN | 101801960 A | 8/2010 |
| CN | 102459185 A | 5/2012 |
| JP | H03261783 A | 11/1991 |
| JP | 2001114768 A | 4/2001 |
| JP | 2009500305 A | 1/2009 |
| JP | 2009501759 A | 1/2009 |
| JP | 2010539209 A | 12/2010 |
| JP | 2012106996 A | 6/2012 |
| JP | 2022521341 A | 4/2022 |
| WO | 01060784 A1 | 8/2001 |
| WO | 0230863 A2 | 4/2002 |
| WO | 2005086661 A2 | 9/2005 |
| WO | 2007003419 A1 | 1/2007 |
| WO | WO2007009913 A1 * | 1/2007 |
| WO | 2007128492 A1 | 11/2007 |
| WO | 2007134864 A1 | 11/2007 |
| WO | 2008030618 A1 | 3/2008 |
| WO | 2008046657 A1 | 4/2008 |
| WO | 2009037172 A1 | 3/2009 |

(Continued)

OTHER PUBLICATIONS

Danzi, S. et al., "Cardiac specific effects of thyroid hormone analogues", Hormone and Metabolic Research, Dec. 31, 2011, vol. 43, No. 11, pp. 737-742, ISSN:0018-5043. pp. 1-7.

(Continued)

*Primary Examiner* — Kamal A Saeed
*Assistant Examiner* — Karen Cheng
(74) *Attorney, Agent, or Firm* — NKL Law; Allen Xue

(57) ABSTRACT

A compound of formula (I) or (Ia), or a tautomer or a pharmaceutically acceptable salt thereof is provided. Compounds of formula (II) to (V), or a tautomer or a pharmaceutically acceptable salt thereof are also provided. These compounds and the pharmaceutical compositions containing them are useful for the treatment of diseases such as obesity, hyperlipidemia, hypercholesterolemia and diabetes and other related disorders and diseases, and may be useful for other diseases such as NASH, atherosclerosis, cardiovascular diseases, hypothyroidism, thyroid cancer and other disorders and diseases related thereto. (I), (Ia)

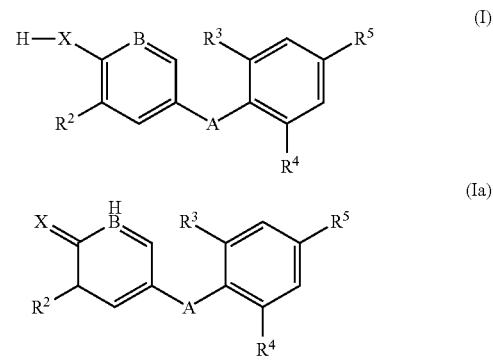

14 Claims, No Drawings

(56) References Cited

FOREIGN PATENT DOCUMENTS

| WO | 2010122980 A1 | 10/2010 |
| WO | 2014043706 A1 | 3/2014 |
| WO | 2018075650 A1 | 4/2018 |
| WO | 2019144835 A1 | 8/2019 |
| WO | 2019240938 A1 | 12/2019 |
| WO | 2019242766 A1 | 12/2019 |
| WO | 2020010068 A1 | 1/2020 |
| WO | WO2020073974 A1 * | 4/2020 |

OTHER PUBLICATIONS

Chemical Abstracts Service, Columbus, Ohio, "345935-02-6: 1, 2, 4-Triazine-6-carbonitrile, 2, 3, 4, 5-tetrahydro-3, 5-dioxo-2-[4-(2-thienylcarbonyl)phenyl]-", CAS Registry File, Jul. 15, 2001 (Jul. 15, 2001), pp. 3.

Miller, Max W. et al., "Anticoccidial derivatives of 6-azauracil. 3. Synthesis, high activity, and short plasma half-life of 1-phenyl-6-azauracils containing sulfonamide substituents", Journal of Medicinal Chemistry, Oct. 1, 1980, vol. 23, No. 10, pp. 1083-1087, ISSN:0022-2623.

Wiedermannova, Iveta et al., "The synthesis of some polycyclic N-H acids with quinoxaline and [1, 2, 4]triazines", ARKIVOC, Dec. 31, 2003, No. 15, pp. 65-74, ISSN:1551-7012.

Wiedermannova, Iveta et al., "Synthesis of some isomeric quinoxaline derivatives with 6-azauracil cycle", Journal of Heterocyclic Chemistry, Dec. 31, 2001, vol. 38, No. 06, pp. 1465-1468, ISSN:0022-152X.

Slouka, J., "5-Substituted 6-azauracils. Part 7: Synthesis of some derivatives of 5-[4-(6-azauracil-1-yl)benzyl]-6-azauracil", Chemical Information Service, Apr. 28, 1981, vol. 12, No. 17, pp. 99-100.

Kelly, Martha J. et al., "Discovery of 2-[3,5-dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β agonist in clinical trials for the treatment of dyslipidemia", Journal of Medicinal Chemistry, Apr. 8, 2014, vol. 57, No. 10, pp. 3912-3923, ISSN: 0022-2623.

Nagase, Hiroshi, "The Practice of Medicinal Chemistry", Aug. 15, 1998, vol. 1, K.K. Technomic, pp. 248-253, ISBN 4-924746-59-2.

Abel, E. Dale et al., "Divergent roles for thyroid hormone receptor beta isoforms in the endocrine axis and auditory system", The Journal of Clinical Investigation, Aug. 1999, vol. 104, No. 03, pp. 291-300.

* cited by examiner

COMPOUNDS AND THEIR USES AS THYROID HORMONE RECEPTOR AGONISTS

BACKGROUND OF THE INVENTION

1. Technical Field

The present invention is directed to novel thyroid hormone receptor agonists. The invention is also directed to the usage of such compounds for treating metabolic diseases such as obesity, hyperlipidemia, hypercholesterolemia, diabetes and other disorders and diseases such as NASH (nonalcoholic steatohepatitis), liver steatosis, atherosclerosis, cardiovascular diseases, hypothyroidism, thyroid cancer and related disorders and diseases.

2. Description of Related Art

Thyroid hormones are hormones produced and released by the thyroid gland. They are primarily responsible for regulation of metabolism and are critical for normal growth and development and for maintaining metabolic homeostasis. Circulating levels of thyroid hormones are tightly regulated by feedback mechanisms in the hypothalamus/pituitary/thyroid (HPT) axis. They also exert profound effects on cardiac function, body weight, metabolism, metabolic rate, body temperature, cholesterol, bone, muscle and behavior.

The biological activity of thyroid hormones is mediated by thyroid hormone receptors (TRs). TRs belong to the superfamily known as nuclear receptors. TRs form heterodimers with the retinoid receptor that act as ligand-inducible transcription factors. TRs have a ligand binding domain, a DNA binding domain, and an amino terminal domain. TRs regulate gene expression through interactions with DNA response elements and with various nuclear co-activators and co-repressors. TRs are derived from two separate genes, α and β, which can further classified as TRα1, TRα2, TRβ1 and TRβ2. Among them, thyroid hormone receptors α1, β1 and β2 can binding to thyroid hormone. Different subtypes of TRs can differ in their contribution to particular biological responses. For examples, TRβ1 plays an important role in regulating TRH (thyrotropin releasing hormone) and on regulating thyroid hormone actions in the liver; TRβ2 plays an important role in the regulation of TSH (thyroid stimulating hormone) (Abel et. al. J. Clin. Invest., Vol 104: pp. 291-300 (1999)).

Recent studies have revealed that the rational use of thyroid hormones can produce some beneficial therapeutic effects. For example, thyroid hormones increase metabolic rate, oxygen consumption and heat production and thereby reduce body weight. Reducing body weight will have a beneficial effect in obese patients, and may also have a beneficial effect on glycemic control in obese patients with Type 2 diabetes.

Other therapeutic benefit of thyroid hormones include the lowering of the low density lipoprotein (LDL), the increasing of hepatic LDL receptor expression, the stimulating of the metabolism of cholesterol to bile acids, the increasing of HDL cholesterol and the improving of the ratio LDL to HDL. Thyroid hormones also may lower the risk of atherosclerosis and other cardiovascular diseases.

With the incidence of obesity and its co-morbidities, diabetes, metabolic syndrome, and atherosclerotic vascular disease rising at epidemic rates, the utility of compounds capable of treating these diseases would be highly desirable. To date, the therapeutic uses of the naturally occurring thyroid hormone have been limited by the adverse side effects associated with hyperthyroidism, especially cardiovascular toxicity.

Therefore, efforts have been made to synthesize thyroid hormone analogs which exhibit increased TRβ selectivity and/or tissue selective action. Such thyroid hormone mimetics may yield desirable reductions in body weight, lipids, cholesterol, and lipoproteins, with reduced impact on cardiovascular function or normal function of the hypothalamus/pituitary/thyroid axis.

For examples, WO2001060784A1 disclosed aniline-derived ligands of the formula below for the thyroid receptor,

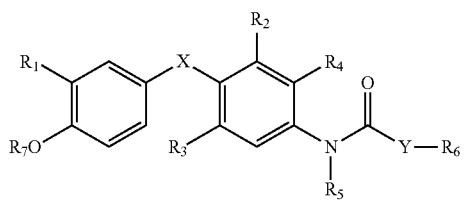

Wherein X is —O—, —S—, —CH$_2$—, —CO—, or —NH—; Y is —(CH$_2$)n- where n is an integer from 1 to 5, or cis- or trans-ethylene; R$_1$ is halogen, trifluoromethyl, or alkyl of 1 to 6 carbons or cycloalkyl of 3 to 7 carbons; R$_2$ and R$_3$ are the same or different and are hydrogen, halogen, alkyl of 1 to 4 carbons or cycloalkyl of 3 to 6 carbons, at least one of R$_2$ and R$_3$ being other than hydrogen; R$_4$ is hydrogen c or lower alkyl; R$_5$ is hydrogen or lower alkyl; R$_6$ is carboxylic acid or esters or prodrugs; R$_7$ is hydrogen or an alkanoyl or an aroyl.

WO2007009913A1 disclosed pyridazinone derivatives of the formula below as thyroid hormone receptor agonists,

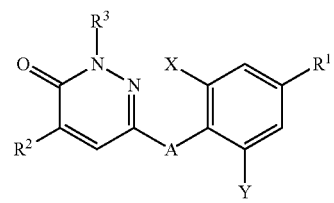

wherein A is O, CH$_2$, S, SO or SO$_2$; X and Y are each independently selected from the group consisting of Br, Cl and —CH$_3$; R$^1$ is selected from the group consisting of: —(CH$_2$)nCOOH; —OCH$_2$COOH; —NHC(=O)COOH; —NHCH$_2$COOH;

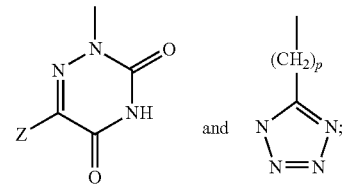

Z is H, or —C≡N; R$^2$ is lower alkyl; R$^3$ is H or lower alkyl; n is 1, 2 or 3; p is 1 or 2; or a pharmaceutically acceptable salt or ester thereof.

WO2009037172A1 disclosed pyridazinone derivatives of the formula below as prodrugs to thyroid hormone analogs,

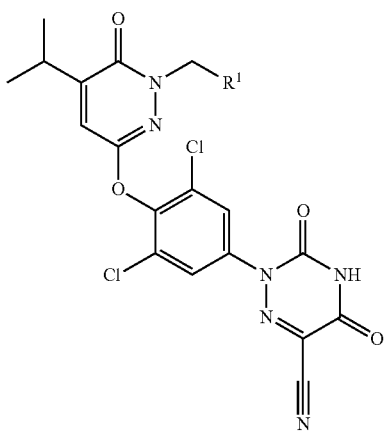

wherein R¹ is —OH, O-linked amino acid, —OP(O)(OH)² or —OC(O)—R²; R² is lower alkyl, alkoxy, alkyl acid, cycloalkyl, heterocycloalkyl, —(CH₂)n-heterocycloalkyl, aryl, heteroaryl, or —(CH₂)n-heteroaryl; and n is 0 or 1; or pharmaceutically acceptable salts and esters thereof.

WO2010122980A1 disclosed the formula below as thyroid hormone receptor agonists,

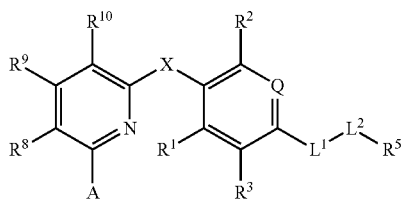

Wherein A is optionally substituted alkyl, optionally substitutedcarbocyclic group, optionally substituted aryl, optionallysubstituted heterocyclic group, optionally substitutedheteroaryl, optionally substituted amino, oroptionally-substitutedcarbamoyl, X is optionally substituted methylene, —O— or —S—, Q is N or C—R⁴, L¹ is single bond, methylene, —CH=CH—, —O—, —CO—, —NR¹¹—, —NR¹¹CO—, —CONR¹¹—, —CH₂NR¹¹— or —S—, L² is single bond-CR⁶R⁷—, or divalent heterocyclicgroup, R¹ and R² are the same or different and each is hydrogen, alkyl, alkenyl or halogen, R³ and R⁴ are the same or different and each is hydrogen, alkyl, alkoxy, cyano or halogen, R¹ and R³ are optionally bonded to form carbocycle orheterocycle, R⁵ is carboxyl group, alkoxycarbonyl group or bioisostericgroup of carboxyl group, R⁶ and R⁷ are the same or different and each is hydrogen, optionally substituted alkyl or halogen, or R⁶ and R⁷ are bonded to form cycloalkane or heterocycle, R⁸ is hydroxy, alkanoylamino or alkylsulfonylamino, R⁹ and R¹⁰ are the same or different and each is hydrogen, alkyl or halogen, and R¹⁰ is hydrogen or alkyl, or a pharmacologically acceptable salt thereof.

The development of thyroid hormone analogs which avoid the undesirable effects of hyperthyroidism and hypothyroidism while maintaining the beneficial effects of thyroid hormones would open new avenues of treatment for patients with metabolic diseases such as obesity, hyperlipidemia, hypercholesterolemia, diabetes and other disorders and diseases such as liver steatosis and NASH, atherosclerosis, cardiovascular diseases, hypothyroidism, thyroid cancer, thyroid diseases, and related disorders and diseases.

The continuing and increasing problems of metabolic diseases, and the current lack of safe and effective drugs for treating them, highlight the overwhelming need for new THR agonist drugs without undesirable effects to treat them.

BRIEF SUMMARY OF THE INVENTION

A technical problem to be solved by the present invention is to provide novel thyroid receptoragonists which are useful for treating metabolic diseases such as obesity, hyperlipidemia, hypercholesterolemia and diabetes and may be useful for other disorders and diseases such as NASH, liver steatosis, atherosclerosis, cardiovascular diseases, hypothyroidism, thyroid cancer and related disorders and diseases.

To solve the above technical problem, the following technical solutions are adopted in the present invention.

In one aspect, provided herein are compounds of Formula (I) or (Ia), ora tautomer ora pharmaceutically acceptable salt thereof,

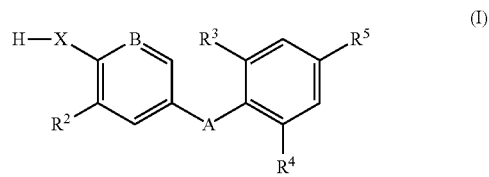

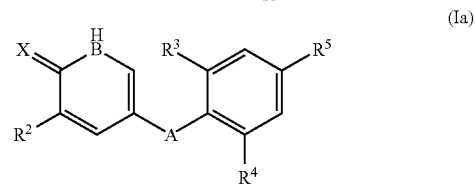

Wherein:
A is O or CH₂;
B is N or CH;
X is O or NR¹ or CHR¹;
R¹ is selected from bond or H or lower alkyl;
R² is H or lower alkyl;
or R¹ and R² together with the X—C=C to which they are connected to form a 5- to 9-membered carbon or hetero cycle, the hetero cycle is non-substituted or substituted by R⁶ and R⁷, R⁶ and R⁷ are independently selected from the group H or lower alkyl;
R³ and R⁴ are independently selected from the group consisting of H, F, Cl, Br and CH₃;
R⁵ is selected from the group consisting of:

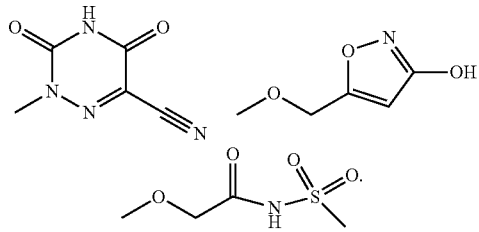

The compound of formula (I) or (Ia), wherein B is CH;
More preferably, wherein A is CH₂;
More preferably, wherein X is O, R² is lower alkyl.
More preferably, wherein R² is i-Pr.

More preferably, wherein $R^3$ and $R^4$ are independently selected from the group consisting of F, H, Cl or $CH_3$.

More preferably, wherein $R^5$ is

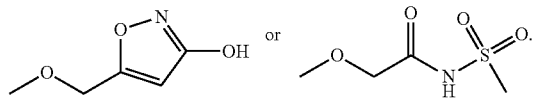

The compounds of formula (I) or (Ia), wherein B is CH, A is O.

More preferably, wherein $R^5$ is

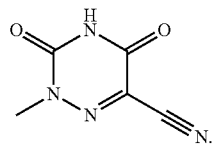

More preferably, wherein X is $NR^1$ or $CHR^1$, $R^1$ and $R^2$ together with the X—C=C to which they are connected to form a 5-membered hetero cycle which is

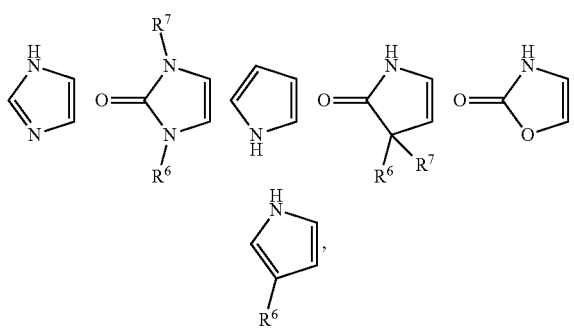

$R^6$ and $R^7$ are independently selected from the group H or Me.

More preferably, wherein $R^3$ and $R^4$ are independently selected from the group consisting of F, H, Cl, $CH_3$.

The compounds of formula (I) or (Ia), wherein B is N.

More preferably, wherein $R^5$ is

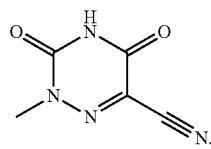

More preferably, wherein $R^3$ and $R^4$ are independently selected from the group consisting of F, H, Cl or $CH_3$.

In some embodiments, wherein A is $CH_2$.
More preferably, wherein X is O.
In some embodiments, wherein A is O.
More preferably, wherein X is O.
More preferably, wherein $R^2$ is i-Pr, Me or cyclopropyl.
In some embodiments, wherein A is O, X is $NR^1$.
More preferably, wherein $R^1$ and $R^2$ together with the X—C=C to which they are connected form a 5-membered heterocyclesubstituted by $R^6$, which is

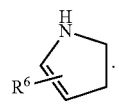

More preferably, wherein $R^6$ is H, Me, Et, Pr, i-Pr or cyclopropyl.

A particularly preferred compound of formula (I) or (Ia), as defined above is

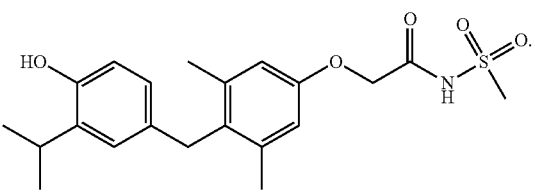

I1

Another particularly preferred compound of formula (I) or (Ia), as defined above is

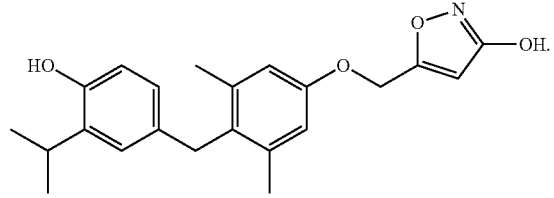

I2

Another particularly preferred compound of formula (I) or (Ia), as defined above is

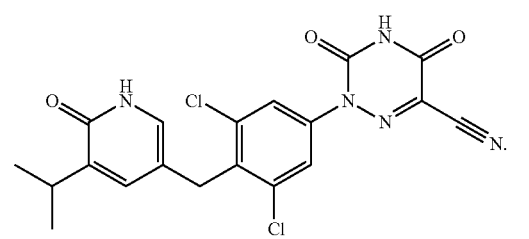

I3

A particularly preferred compound of formula (I) or (Ia), as defined above is that selected from one of the following structures:

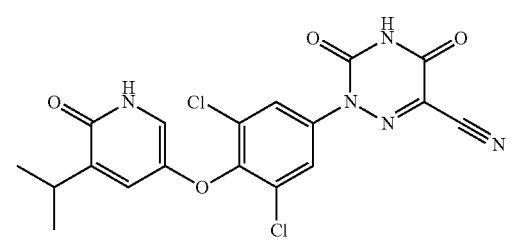

I4

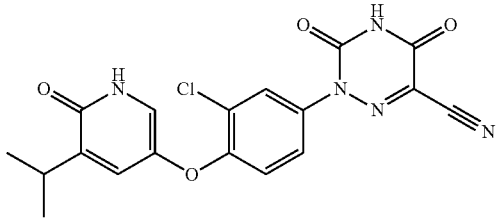
I5
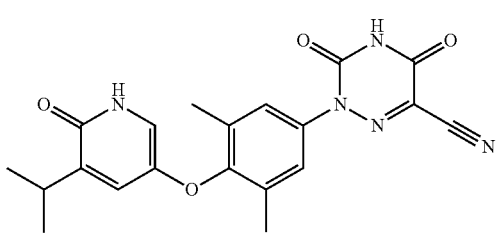
I6
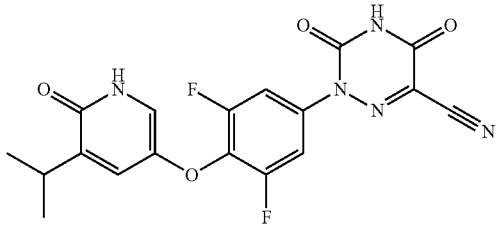
I7
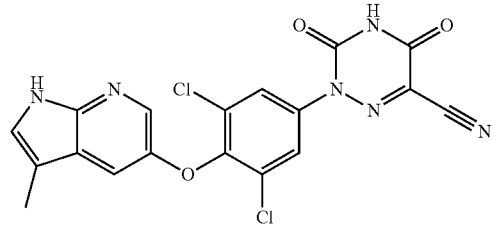
I8
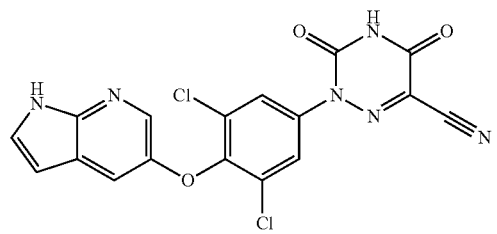
I9
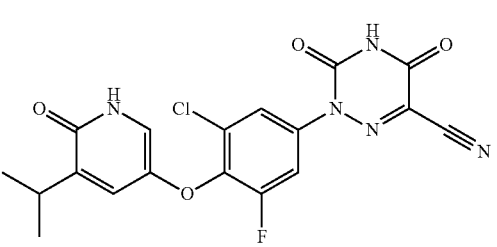
I10
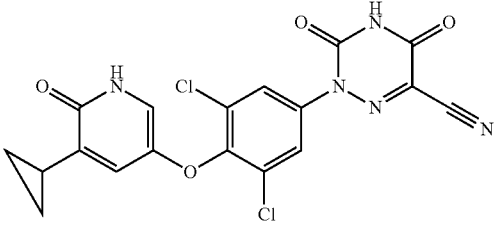
I11
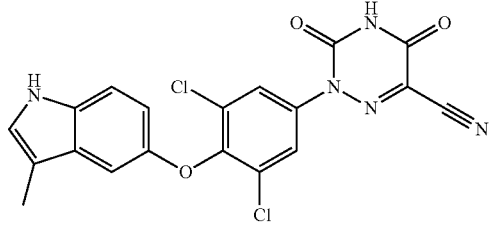
I12
or a tautomer or a pharmaceutically acceptable salt thereof.
A particularly preferred compound of formula (I) or (Ia), as defined above is that selected from one of the following structures:
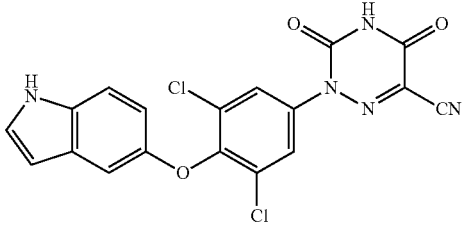
I13
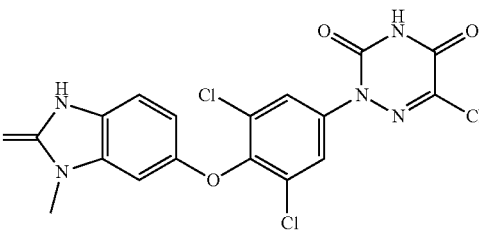
I14
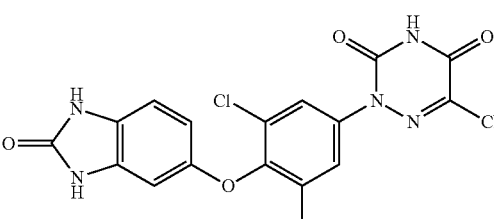
I15
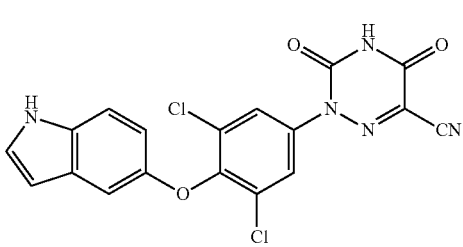
I16

I17
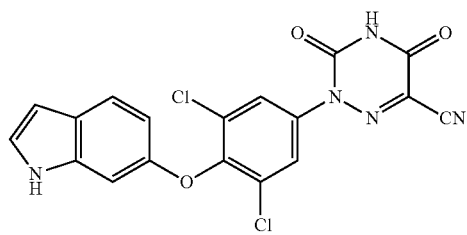

I18
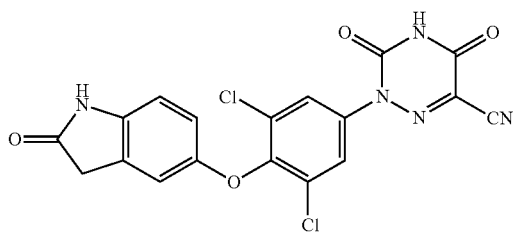

I19

I20

I21
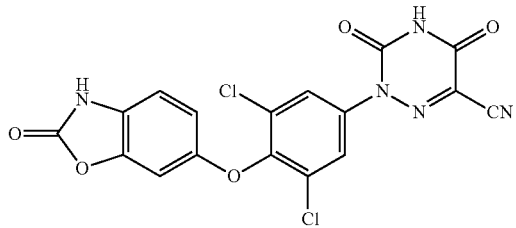

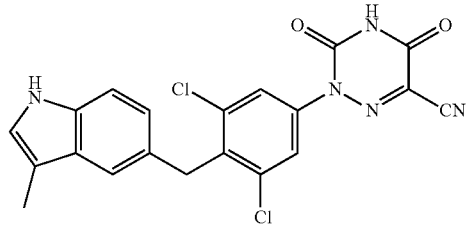

or a tautomer or a pharmaceutically acceptable salt thereof.

In another aspect, provided herein are compounds of Formula (II), or a tautomer or a pharmaceutically acceptable salt thereof, II
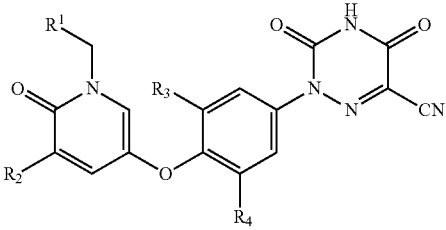

Wherein:
R¹ is OH, O-linked amino acid, OC(O)R⁹ or OP(O)(OH)₂, R⁹ is H, alkoxy or lower alkyl;
R² is H or lower alkyl;
R³ and R⁴ are independently selected from the group consisting of H, F, Cl, Br or CH₃.

A particularly preferred compound of formula (II), as defined above is that selected from one of the following structures:

I22
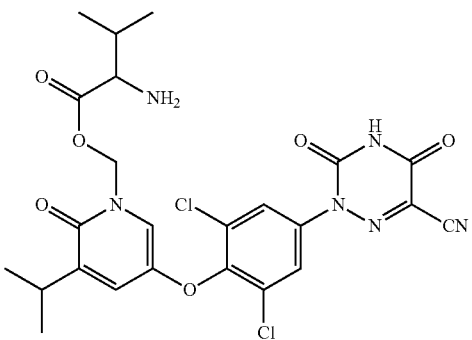

I23
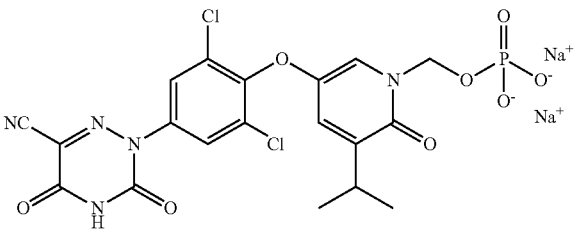

I24
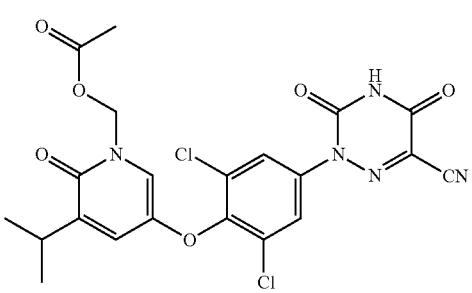

or a tautomer or a pharmaceutically acceptable salt thereof.

In another aspect, provided herein are compounds of Formula (III), or a tautomer or a pharmaceutically acceptable salt thereof,

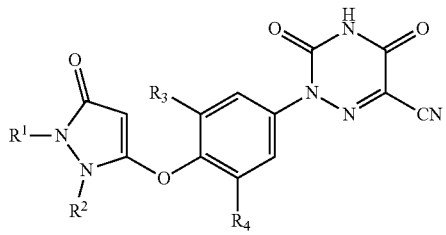

III

Wherein:
R¹ is H, CH₂OH, CH₂O-linked amino acid, CH₂OC(O)R⁹ or CH₂OP(O)(OH)₂, R⁹ is H, alkoxy or lower alkyl;
R² is H or lower alkyl;
R³ and R⁴ are independently selected from the group consisting of H, F, Cl, Br or CH₃.

A particularly preferred compound of formula (III), as defined above is that selected from one of the following structures:

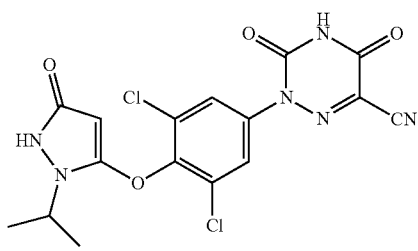

I25

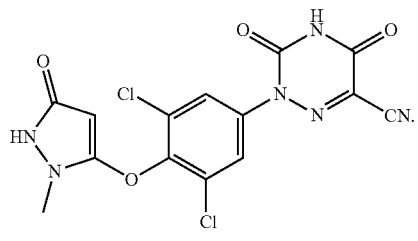

I26 or a tautomer or a pharmaceutically acceptable salt thereof.

In another aspect, provided herein are compounds of Formula (IV), or a tautomer or a pharmaceutically acceptable salt thereof,

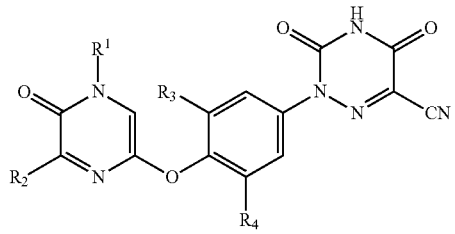

IV

Wherein:
R¹ is H, CH₂OH, CH₂O-linked amino acid, CH₂OC(O)R⁹ or CH₂OP(O)(OH)₂, R⁹ is H, alkoxy or lower alkyl;
R² is H or lower alkyl;
R³ and R⁴ are independently selected from the group consisting of H, F, Cl, Br or CH₃.

A particularly preferred compound of formula (IV), as defined above is:

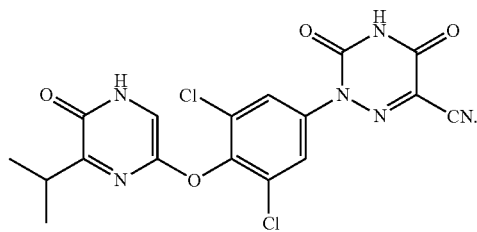

I27 or a tautomer or a pharmaceutically acceptable salt thereof.

In another aspect, provided herein are compounds of Formula (V), or a tautomer or a pharmaceutically acceptable salt thereof,

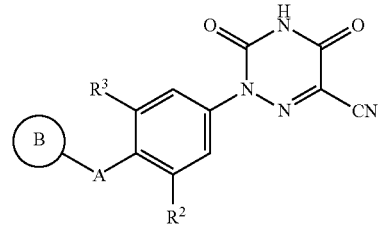

V

Wherein:
A is O, S, S(O)₂, C(O) or CH₂;
B is a substituted or no-substituted monocyclic 4-7 membered ring or a bicyclic 6-11 membered ring with one or two hetero atoms on the ring, the substituted substituents are each independently, optionally, selected from one or more of alkyl, alkenyl, alkynyl, haloalkyl, hydroxyalkyl, cycloalkyl, heterocyclyl, aryl, heteroaryl, =O, —OR¹, —C(O)R¹ or —C(O)OR¹;
R¹ is selected from hydrogen atom, C₁₋₆ alkyl or C₃₋₁₀ cycloalkyl;
R² and R³ are independently selected from the group consisting of H, F, Cl, Br or CH₃.

The compounds of Formula (V), Wherein, A is O or CH₂;
The compounds of Formula (V),
Wherein, B is selected from:

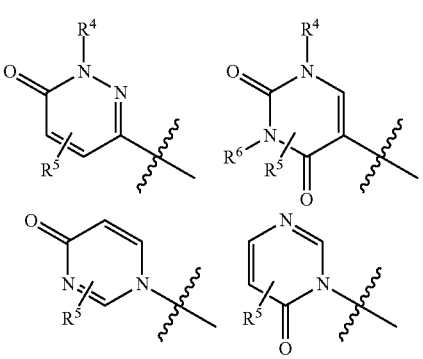

-continued

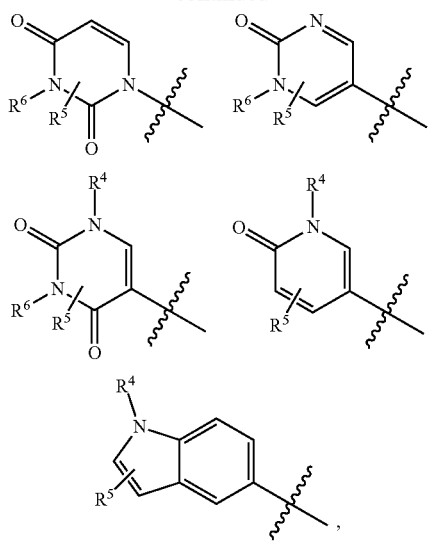

R⁴ is selected from H, alkyl, alkenyl, alkynyl, haloalkyl, hydroxyalkyl or cycloalkyl, R⁵ is selected from H, $C_{1-6}$ alkyl or $C_{3-10}$ cycloalkyl, R⁶ is selected from H, alkyl, alkenyl, alkynyl, haloalkyl, hydroxyalkyl or cycloalkyl.

More preferably, Wherein R⁴ is selected from H, CH₂OH, Me, Et, Pr, i-Pr, butyl, t-butyl, i-butyl, cyclopropyl or cyclobutyl.

A particularly preferred compound of formula (V), as defined above is that selected from one of the following structures:

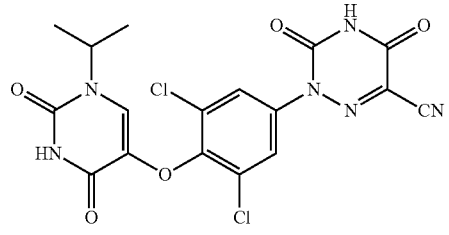

I28

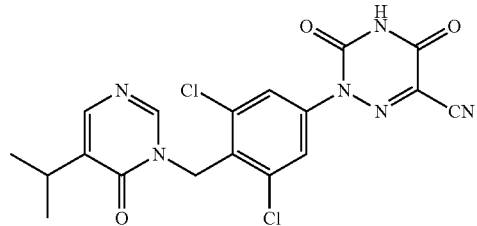

I29

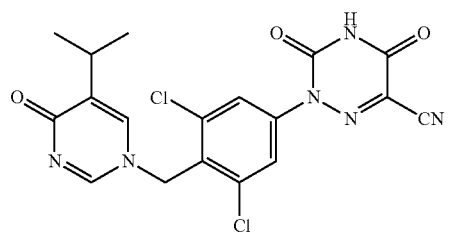

I30

-continued

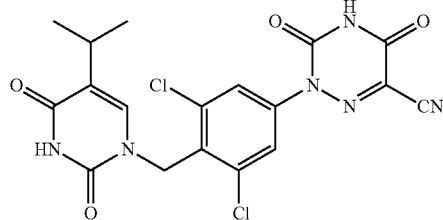

I31

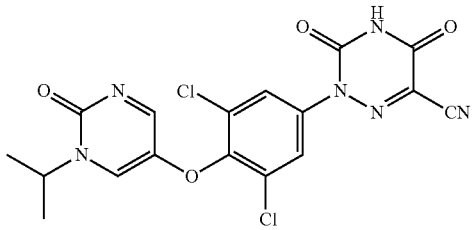

I32

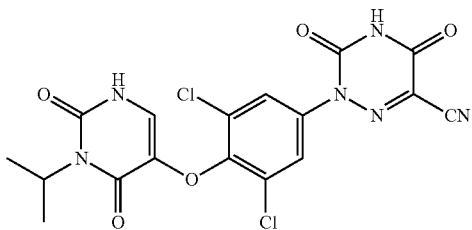

I33

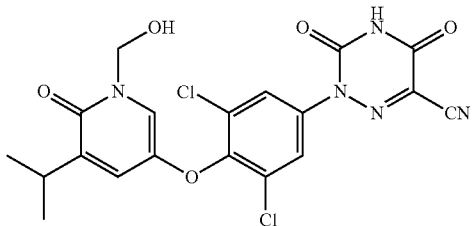

I34

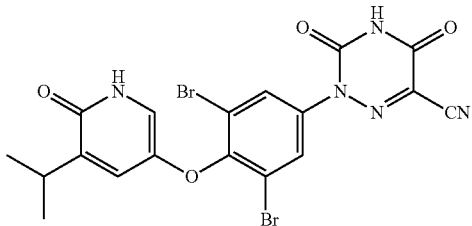

I35

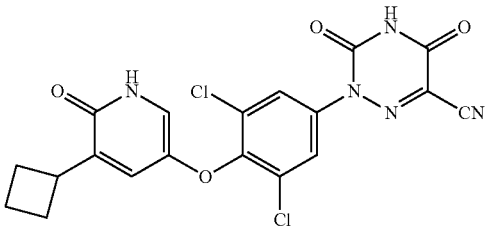

I36

-continued

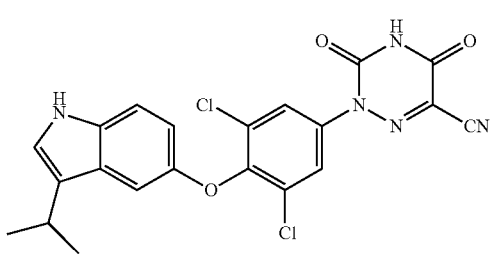

I37

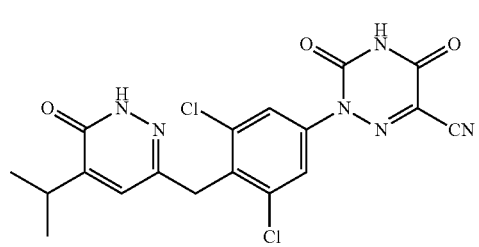

I38

It will be appreciated that the compounds of general formula (I) or (Ia) or the compounds of general formula (II)~(V) in this invention may be derivatised at functional groups to provide derivatives which are capable of conversion back to the parent compound in vivo.

As described above, the novel compounds of the present invention have been found to be thyroid hormone analogs. The compounds of the present invention can therefore be used in the treatment and/or prophylaxis of diseases which are modulated by thyroid hormone analogs, particularly metabolic diseases, such as obesity, hyperlipidemia, hypercholesterolemia and diabetes, and may be useful for other diseases such as NASH (nonalcoholic steatohepatitis), atherosclerosis, cardiovascular diseases, hypothyroidism, thyroid cancer and related disorders and diseases. An obese patient is a human with a body mass index of 25 or greater.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by thyroid hormone analogs, particularly metabolic diseases, such as obesity, hyperlipidemia, hypercholesterolemia and diabetes, and NASH (nonalcoholic steatohepatitis), atherosclerosis, cardiovascular diseases, hypothyroidism, thyroid cancer and related disorders and diseases.

In another preferred example, the invention relates to a method for the therapeutic and/or prophylactic treatment of diseases which are modulated by thyroid hormone analogs, particularly metabolic diseases, such as obesity, hyperlipidemia, hypercholesterolemia and diabetes, and NASH (nonalcoholic steatohepatitis), atherosclerosis, cardiovascular diseases, hypothyroidism, thyroid cancer and related disorders and diseases, which method comprises administering a compound as defined above to a human being or animal. Preferably, the amount of the compound administered is from about 0.01 mg/kg to about 50 mg/kg per day, more preferably from about 0.3 mg/kg to about 10 mg/kg per day, even more preferably from about 0.70 mg/kg to about 3.5 mg/kg per day.

The invention also embraces the use of compounds as defined above for the therapeutic and/or prophylactic treatment of diseases which are modulated by thyroid hormone analogs, particularly metabolic diseases, such as obesity, hyperlipidemia, hypercholesterolemia and diabetes, and NASH (nonalcoholic steatohepatitis), atherosclerosis, cardiovascular diseases, hypothyroidism, thyroid cancer and related disorders and diseases.

The invention also relates to the use of compounds as described above for the preparation of medicaments for the therapeutic and/or prophylactic treatment of diseases which are modulated by thyroid hormone analogs, particularly metabolic diseases, such as obesity, hyperlipidemia, hypercholesterolemia and diabetes, and NASH (nonalcoholic steatohepatitis), atherosclerosis, cardiovascular diseases, hypothyroidism, thyroid cancer and related disorders and diseases. Such medicaments comprise a compound as described above.

Prevention and/or treatment of metabolic diseases is the preferred indication. Diabetes is more preferred, particularly non insulin dependent diabetes (type 2). Obesity also is more preferred. Hyperlipidemia also is more preferred, particularly hypercholesterolemia.

Compounds of the present invention can be prepared beginning with commercially available starting materials and utilizing general synthetic techniques and procedures known to those skilled in the art. Outlined below are reaction schemes suitable for preparing such compounds. Further exemplification is found in the specific Examples detailed below.

When B is C, A is $CH_2$, X is O, $R^2$ is lower alkyl, $R^3$ and $R^4$ are independently selected from the group consisting of F, H, Cl, $CH_3$, $R^5$ is

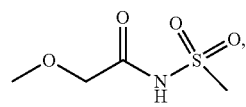

the compound of Formula (I) or (Ia) is synthesized through method A, which is a series of reactions outlined in scheme 1.

Method A

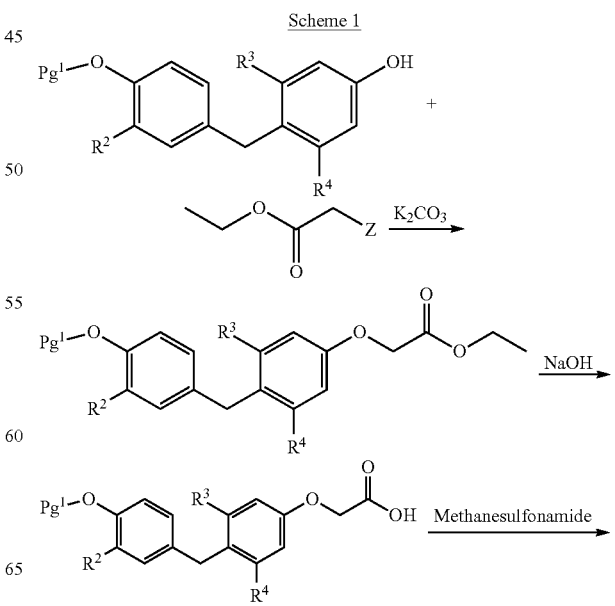

Scheme 1

-continued

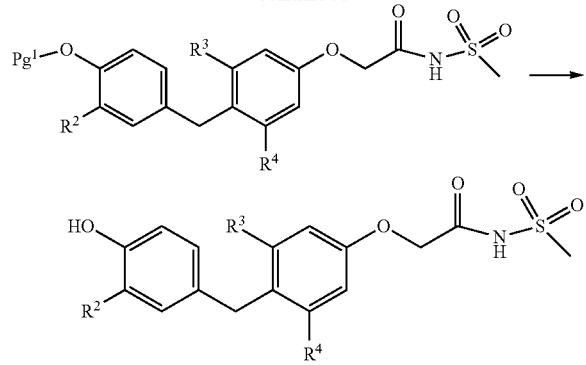

R² is lower alkyl, R³ and R⁴ are independently selected from the group consisting of F, H, Cl, CH₃; Z is Cl or Br; Pg¹ is selected from common protecting group for phenolic hydroxyl group.

When B is C, A is CH₂, X is O, R² is lower alkyl, R³ and R⁴ are independently selected from the group consisting of F, H, Cl, CH₃, R⁵ is

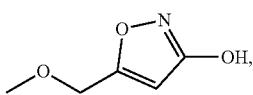

the compound of Formula (I) or (Ia) is synthesized through method B, which is a series of reactions outlined in scheme 2.

Method B

Scheme 2

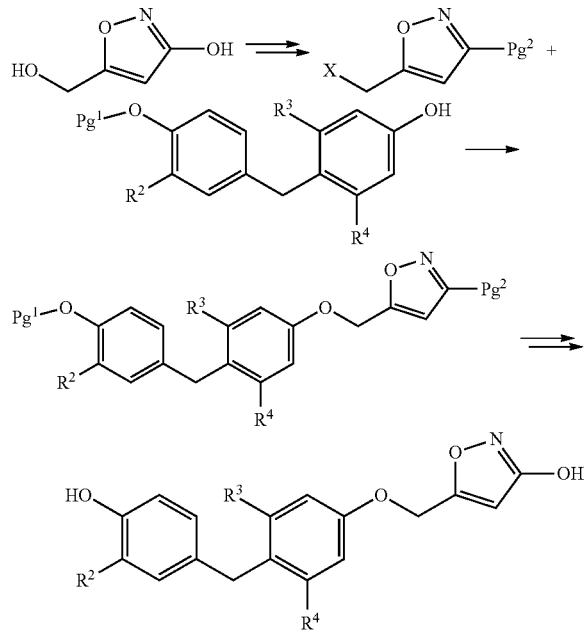

R² is lower alkyl, R³ and R⁴ are independently selected from the group consisting of F, H, Cl, CH₃; Z is F, Cl or Br; Pg¹ and Pg² are independently selected from common protecting group for phenolic hydroxyl group.

When B is N, A is CH₂, X is O, R² is lower alkyl, R³ and R⁴ are independently selected from the group consisting of F, H, Cl or CH₃, R⁵ is

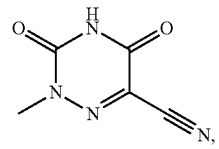

the compound of Formula (I) or (Ia) is synthesized through method C, which is a series of reactions outlined in scheme 3.

Method C

Scheme 3

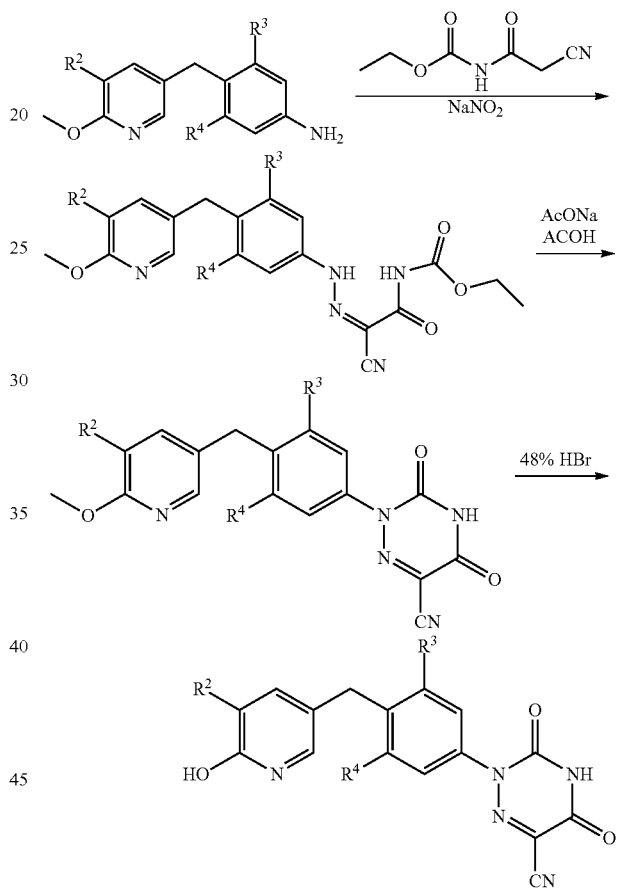

R² is lower alkyl, R³ and R⁴ are independently selected from the group consisting of F, H, Cl, CH₃.

When B is N, A is O, X is O, R² is lower alkyl, R³ and R⁴ are independently selected from the group consisting of F, H, Cl, CH₃, R⁵ is

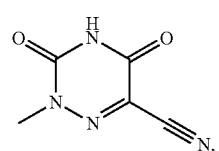

the compound of Formula (I) or (Ia) is synthesized through method D, which is a series of reactions outlined in scheme 4.

Method D

Scheme 4

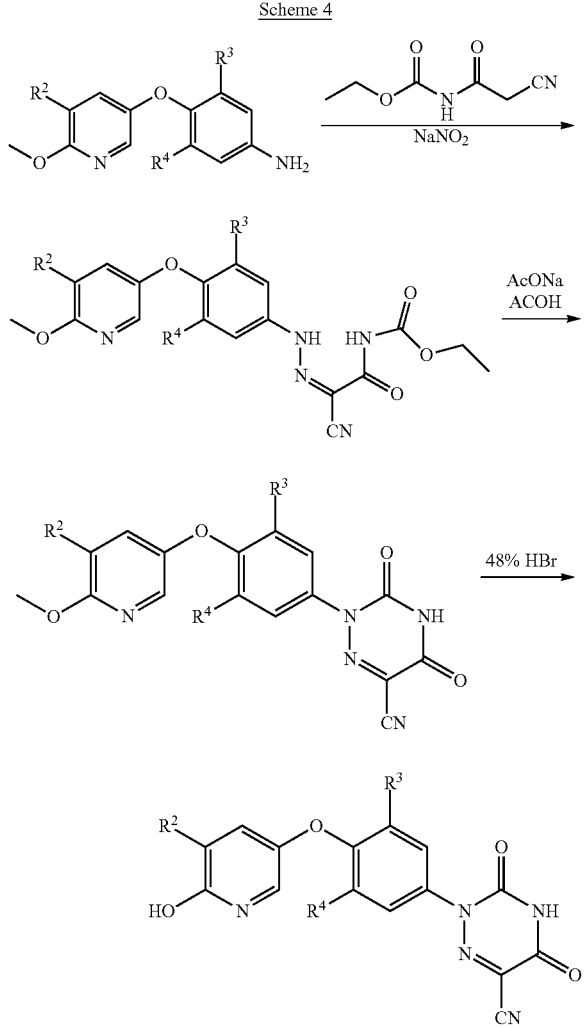

$R^2$ is lower alkyl, $R^3$ and $R^4$ are independently selected from the group consisting of F, H, Cl, CH$_3$ When B is N or C, A is O, X is NR$^1$, R$^5$ is

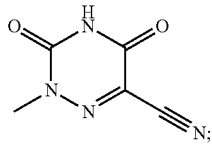

R$^1$ and R$^2$, together with the X—C=C to which they are connected, form a 5-membered hetero cycle substituted by R$^6$; R$^6$ is selected from H, Me, Et, Pr, i-Pr or cyclo-Pr; R$^3$ and R$^4$ are independently selected from the group consisting of F, H, Cl or CH$_3$, the compound of Formula (I) or (Ia) is synthesized through method E, which is a series of reactions outlined in scheme 5.

Method E

Scheme 5

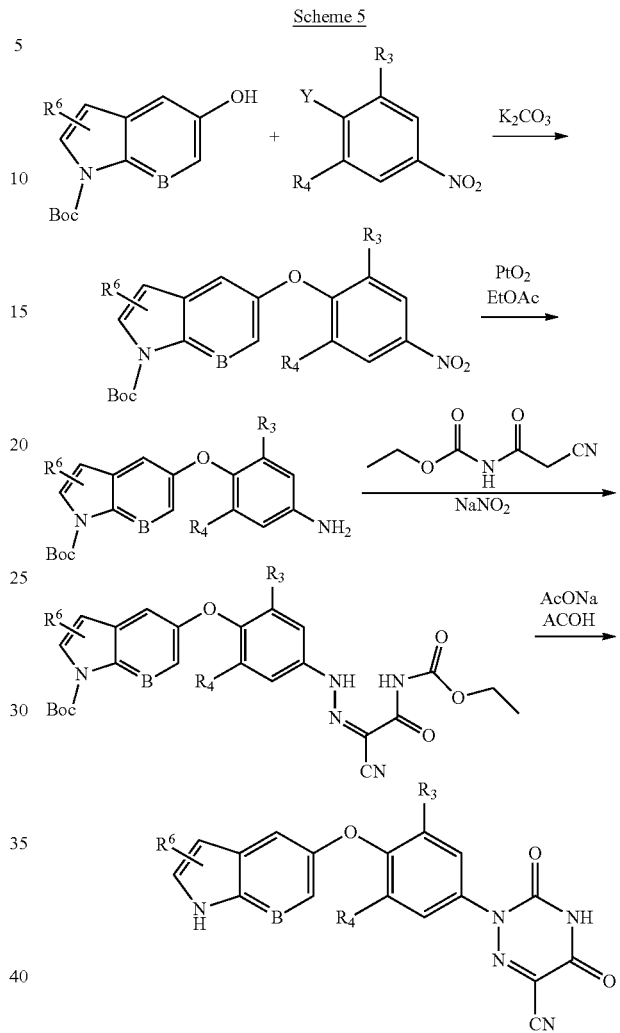

B is N or C, R$^6$ is selected from H, Me, Et, Pr, i-Pr or cyclo-Pr; R$^3$ and R$^4$ are independently selected from the group consisting of F, H, Cl, CH3.

Definitions

The compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley &Sons, New York: 2001, the entire contents of which are hereby incorporated by reference.

It is to be understood that the terminology employed herein is for the purpose of describing particular Examples, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl) hydrocarbyl group which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl orisopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched orunbranched), substituted alkynyl (branchedor unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl) hydrocarbyl group wherein said cyclic lower alkyl group is $C_5$, $C_6$ or $C_7$, and wherein said acyclic lower alkyl group is $C_1$, $C_2$, $C_3$, $C_4$, $C_5$, or $C_6$, preferably from 1 to 4 carbon atoms. Typical lower alkyl groups include methyl, ethyl, propyl (n-propyl or isopropyl), butyl (n-butyl, isobutyl or tertiary-butyl), pentyl and hexyl. It will be appreciated therefore that the term "lower alkyl" as used herein includes, for example, lower alkyl (branched or unbranched), lower alkenyl (branched or unbranched), lower alkynyl (branched or unbranched), cycloloweralkyl, cycloloweralkenyl and cycloloweralkynyl. When attached to another functional group, lower alkyl as used herein may be divalent, e.g., -lower alkyl-COOH. Acyclic, branched or unbranched lower alkyl groups are preferred.

"Pharmaceutically acceptable," such as pharmaceutically acceptable carrier, excipient, etc., means pharmacologically acceptable and substantially non-toxic to the subject to whom the particular compound is administered. "Pharmaceutically acceptable salt" refers to conventional acid-addition salts or base-addition salts that retain the biological effectiveness and properties of the compounds of formula I and are formed from suitable organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems ($6^{th}$ Ed. 1995) at pp. 196 and 1456-1457.

DETAILED DESCRIPTION OF THE INVENTION

Abbreviations: The Following Abbreviations May be Used Herein

| | |
|---|---|
| AcOH | Acetic acid |
| Aq or aq. | Aqueous |
| BOC or Boc | tert-butyloxy carbonyl |
| cpme | cyclopentyl methy 1 ether |
| DCE | 1,2-dichloroethane |
| DAB CO | 1,4 diazahicyclo[2.2.2]octane |
| DCM | Dichloromethane |
| DMA | N,N-Dimethylacetamide |
| DMAP | 4 dimethyl aminopyridine |
| DME | 1,2-dimethoxyethane |
| DMF | N,N-dimethy lformarnide |
| DMSO | dimethyl sulfoxide |
| Dppf, DPPF or dppf | 1,1'-bis(diphenylphosphino)ferrocene |
| eq or eq. or equiv. | Equivalent |
| ESI or ES | electrospray ionization |
| Et | Ethyl |
| $Et_2O$ | diethyl ether |
| EtOAc | Ethyl acetate |
| g | Grams |
| h | Hour |
| HPLC | high pressure liquid chromatography |
| i-Pr | isopropyl |
| $iPr_2NEt$ or DIPEA | N-ethyl diisopropylarnine (Hiinig's base) |
| KHMDS | potassium hexamethyldisilazide |
| KOAc | potassium acetate |
| Lawesson's reagent | 2,4-bis(4-methoxyphenyl)-2,4-dithioxo-1,3,2,4-dithiadiphcsphetane, 2,4-Bis-(4-methoxyphenyl)-1,3-dithia-2,4-diphisphetane4-diphosphetane-2,4-disulfide |
| LC MS, LCMS, LC-MS or LC/MS | liquid chromatography mass spectroscopy |
| LG | Leaving group (e.g.. halogen, mesylate, triflate) |
| LHMDS or LiHMDS | lithium hexarnethyldisilazide |
| m/z | mass divided by charge |
| Me | Methyl |
| MeCN | Acetonitrile |
| MeOH | Methanol |
| Met | Metal species for cross-coupling (e.g., MgX, ZnX, $SnR_3$, $SiR_3$, $B(OR)_2$) |

| | |
|---|---|
| mg | Milligrams |
| min | Minutes |
| mL | Milliliters |
| NaHMDS | sodium hexamethyldisilazide |
| NBS | N-bromosuccinimide |
| n-BuLi | n-butyllithium |
| NCS | N-chlorosuccinimide |
| NMR | Nuclear magnetic resonance |
| $Pd_2(dba)_3$ | tris(dibenzylideneacetone)dipalladium(O) |
| $Pd(dppf)Cl_2 \cdot DCM$ | [1,1'-Bis(diphenylphosphino)ferrocene] dichloropalladium(II), complex with dichloromethane |
| $Pd(PPh_3)_4$ | Tetrakis(triphenylphosphine)palladium(O) |
| RT r.t r.t. or rt | room temperature |
| sat. or satd. | saturated |
| SFC | supercritical fluid chromatography |
| THF | Tetrahydrofuran |
| UV | Ultraviolet |
| t-BuOH | Tert-butanol |
| Xantphos | 4,5-Bis(diphenylphosphino)-9,9-dimethylxanthene |
| $Cs_2CO_3$ | Cesium carbonate |
| PE | petroleum |
| EA | Ethyl acetetae |
| NASH | nonalcoholic steatohepatitis |
| HPT | hypothalamus/pituitar/thyroid |
| TRs | thyroid hormone receptors |
| TRH | thyrotropin releasing hormone |
| TSH | thyroid stimulating hormone |
| LDL | low density lipoprotein |
| TBDMS | tert-butyldimethylsilyl |
| MOM | methoxy methyl ether |
| TBAF | tetrabutyl ammonium fluoride |
| TEA | Triethylamine |
| TFA | trifluoroacetylacetone |
| BTC | Bis(trichloromethyl)carbonate |
| BOP | Benzoyl peroxide |
| DBU | 1,8-Diazabicyclo[5.4.0]undec-7-ene |
| PMB | p-Methoxybenzyl |
| EDCI | 1-Ethyl-3-(3-dimethylaminopropyl) carbodiimide Hydrochloride |

The present invention can be better understood according to the following examples. However, it would be easy for a person skilled in the art to understand that the contents described in the examples are merely intended to illustrate the present invention rather than limit the present invention described in detail in the claims.

Unless otherwise indicated, compounds of the present invention can be prepared beginning with commercially available starting materials and utilizing general synthetic techniques and procedures known to those skilled in the art. Chromatography supplies and equipment may be purchased from such companies as for example AnaLogix, Inc, Burlington, WI; Analytical Sales and Services, Inc., Pompton Plains, NJ; Teledyne Isco, Lincoln, NE; VWR International, Bridgeport, NJ; and Rainin Instrument Company, Woburn, MA. Chemicals may be purchased from companies such as for example Aldrich, Argonaut Technologies, VWR and Lancaster.

Substrate Preparation

1. Synthesis of 5-isopropyl-6-methoxypyridin-3-ol

The subtract 5-isopropyl-6-methoxypyridin-3-ol was prepared from commercial available reagent 2-methoxypyridineaccording to scheme 6.

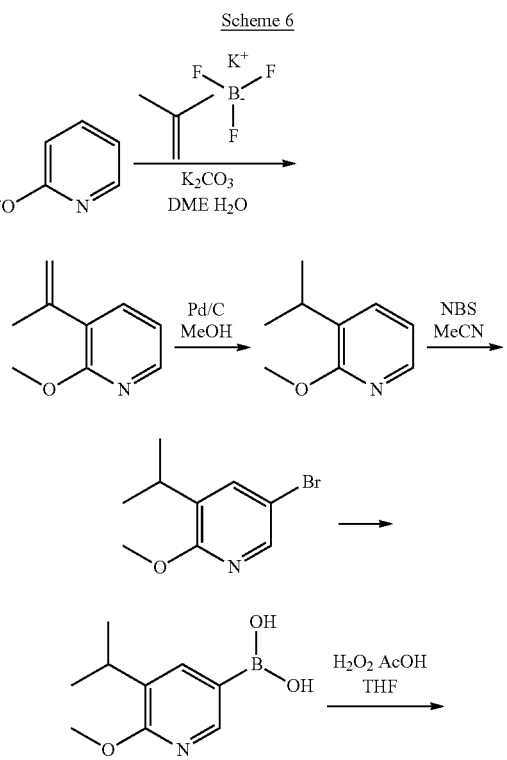

Scheme 6

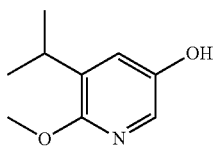

Step 1 Synthesis of 2-methoxy-3-(prop-1-en-2-yl)pyridine

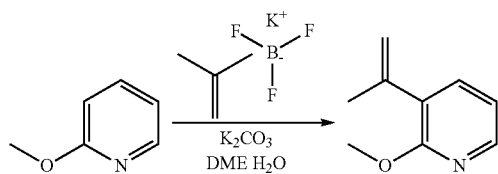

To a mixture of 2-methoxypyridine (20 g, 0.11 mmol, 1.0 eq), potassium propene-2-trifluoroborate (23.61 g, 0.16 mmol, 1.5 eq) and $K_2CO_3$ (73.51 g, 0.53 mmol, 5.0 eq) in 200 mL of mixture of DME and 40 mL of $H_2O$, Pd (dppf) $Cl_2$—$CH_2Cl_2$ (8.68 g, 0.01 mmol, 0.1 eq) was added and the mixture was stirred at 90° C. for 2 hour under nitrogen. After TLC showed the start material was disappeared, the mixture was cooled to room temperature and 100 ml of water was added. The mixture was extracted with 4×100 mL of EA, the organic layers were combined and concentrated. The residue was purified by flash chromatography (PE:EA=10:1) to give 12.5 g of desired product as brown oil, yield: 78.77%.

Step 2 Synthesis of 3-isopropyl-2-methoxypyridine

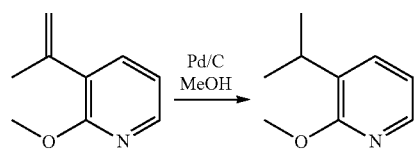

To a solution of 2-methoxy-3-(prop-1-en-2-yl)pyridine (12.5 g, 83.79 mmol, 1.0 eq) in 160 mL of MeOH, Pd/C (1.25 g, 10w/w) was added and the mixture was stirred at r.t. overnight under hydrogen. After HPLCshowed no start material, the precipitate was removed by filtration and the filtrate was concentrated to give desired product as brown oil, yield: 76.56%. $^1$HNMR (400 MHz, $CDCl_3$-$d_3$) δ ppm: 7.94-7.93 (m, 1H), 7.37 (d, J=7.2 Hz, 1H), 6.78-6.73 (m, 1H), 3.88 (s, 3H), 3.15-3.07 (m, 1H), 1.14 (d, J=6.8 Hz, 6H).

Step 3 Synthesis of 5-bromo-3-isopropyl-2-methoxypyridine

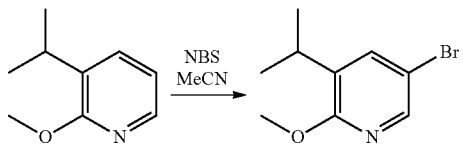

To Synthesis of 3-isopropyl-2-methoxypyridine (9.6 g, 63.49 mmol, 1.0 eq) in 200 mL of MeCN, NBS (14.69 g, 82.53 mmol, 1.3 eq) was added at room temperature, the mixture was refluxed for 3 hours. After HPLC showed no start material, MeCN was removed under vacuum and the residue was diluted with 100 ml of water, extracted with 4×100 mL of EA. the organic layers were combined and concentrated. The residue was purified with flash chromatography (PE:EA=10:1) to give 10.2 g of desired product as brown oil, yield: 69.82%. $^1$HNMR (400 MHZ, $CDCl_3$-$d_3$) δ ppm: 7.955 (d, J=1.6 Hz, 1H), 7.433 (d, J=1.6 Hz, 1H), 3.86 (s, 3H), 3.07-3.02 (m, 1H), 1.12 (d, J=6.8 Hz, 6H).

Step 4 Synthesis of (5-isopropyl-6-methoxypyridin-3-yl)boronic acid

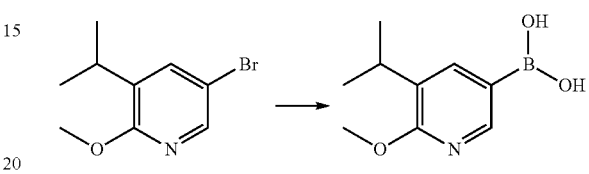

To a solution of 5-bromo-3-isopropyl-2-methoxypyridine (5 g, 21.73 mmol, 1.0 eq) in 30 mL of dry THF, n-BuLi (9.05 mL, 21.73 mmol, 2.4 mol/L, 1.0 eq) was added at −70° C., when HPLC showed no starting material was exist, B(i-PrO)$_3$ (6.13 g, 32.59 mmol, 1.5 eq) was added and stirred at −70° C. for 1 h, then the reaction mixture was stirred at room temperature. Then 50 mL of water was added and the pH value of the reaction mixture was adjusted to 3 with 2N HCl. After extracted with 3 X 80 mL of EA, the organic layers were combined and concentrated. The residue was purified with flash chromatography (DCM:MeOH=10:1) to give 1.05 g of desired product as white solid, yield: 24.78%. LCMS: [M+1]=389.2

Step 5 Synthesis of 5-isopropyl-6-methoxypyridin-3-ol

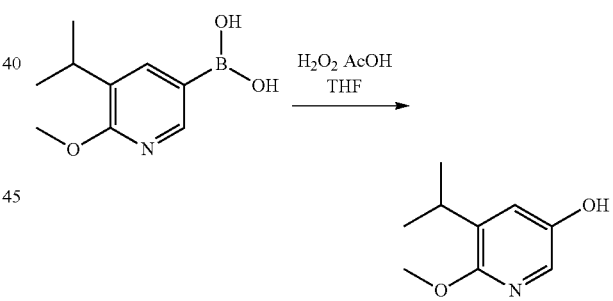

To a solution of (5-isopropyl-6-methoxypyridin-3-yl)boronic acid (4.1 g, 20 mmol, 1.0 eq) in 30 mL of THF, $H_2O_2$ (11.9 g, 105 mmol, 5.0 eq) was added at 0° C. The reaction mixture was then stirred for 10 min, then AcOH (2.52 g, 42 mmol, 2.0 eq) was added dropwise, the mixture was warmed up to room temperature and stirred for several minutes. Then 30 mL aq. solution of the mixture of $Na_2S_2O_3$ and $NaHCO_3$ was added to quench the reaction. The mixture was extracted with 4×20 mL of EA. The organic layers were combined and concentrated. The residue was purified with revered phase chromatography (water:MeOH=1:1) to give 1.1 g of desired product as brown oil, yield: 31.43%. LCMS: [M+1]=168.1

2. Synthesis of 4-(4-hydroxy-3-isopropylbenzyl)-3,5-dimethylphenol

The subtract 4-(4-hydroxy-3-isopropylbenzyl)-3,5-dimethylphenol was prepared from commercial available reagent 2-methoxypyridine according to scheme 7.

Scheme 7

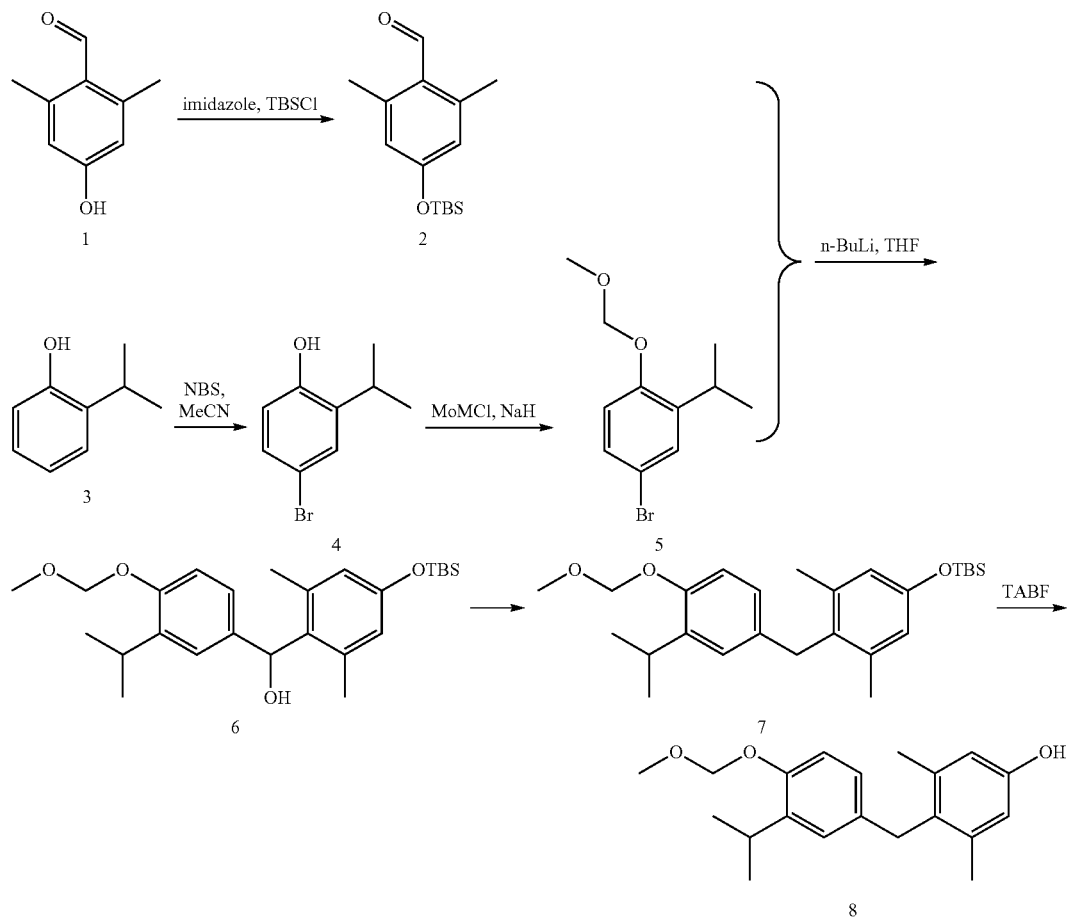

Step 1 Synthesis of Compound 2

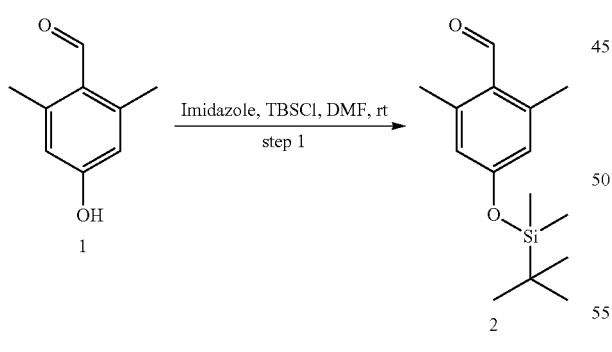

To a solution of compound 1 (20 g, 133.2 mmol, 1.0 eq) and imidazole (18.1 g, 266.4 mmol, 2.0 eq) in 200 mL of DMF at 0° C. under nitrogen atmosphere was added tert-butyldimethylsilyl chloride (24.1 g, 159.8 mmol, 1.2 eq) in portions, and the mixture was stirred at room temperature for 30 min. The mixture was cooled to 0° C., and then water was added. The mixture was extracted with methylene chloride, and the organic phase was washed with water and brine then was dried over sodium sulfate. The solvent was removed under reduced pressure, and the residue was purified by chromatography using heptane/ethyl acetate (100:1) as the mobile phase. Removal of the solvent under reduced pressure gave compound 2 (23 g, light red liquid, yield 65%). LCMS: (ESI-MS): [M+H]$^+$=265.2; $^1$H NMR (400 MHZ, CDCl$_3$) δ ppm: 10.50 (s, 1H), 6.55 (s, 2H), 2.59 (s, 6H), 0.98 (s, 9H), 0.26 (s, 6H).

Step 2 Synthesis of Compound 4

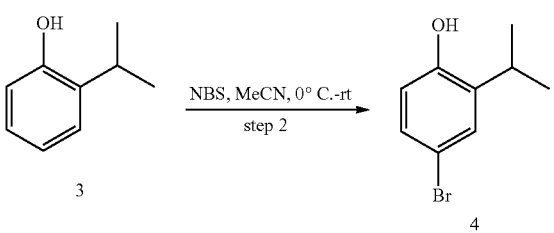

To a solution of compound 3 (20 g, 146.8 mmol, 1.0 eq) in MeCN (200 mL) at 0° C. was added NBS (28.8 g, 161.6 mmol, 1.1 eq). The reaction mixture was stirred at room temperature for 4 h. The reaction mixture was filtered, and the filter cake was washed with hexane and dried to give a crude product compound 4 (25 g), which was used directly in the next step without further purification. LCMS: (ESI-MS): [M+H]+=215.0, 217.0.

Step 3 Synthesis of Compound 5

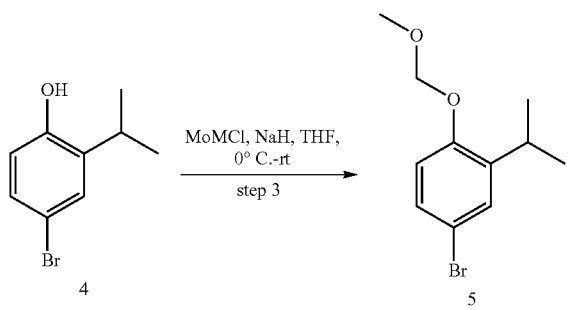

Sodium hydride (60%, 7 g, 174.4 mmol, 1.5 eq) was added in portions to anhydrous THF (200 mL) under an argon atmosphere at 0° C., then a solution of compound 4 (25 g, 116.2 mmol, 1.0 eq) in THF (100 mL) was added dropwise. After the addition, the reaction mixture was warmed up to room temperature and stirred for 30 minutes. Then MOMCl (18.7 g, 232.4 mmol, 2.0 eq) was added dropwise at 0° C. The mixture was warmed to room temperature and stirred for 15 minutes, then diluted with water at 0° C. The aqueous layer was extracted three times with hexane, dried over sodium sulfate and then distilled off the solvent. The obtained residue was purified by silica gel column chromatography (ethyl acetate: n-hexane=1:100). The desired colorless transparent oily compound 5 (20 g, 66%) was obtained.

Step 4 Synthesis of Compound 6

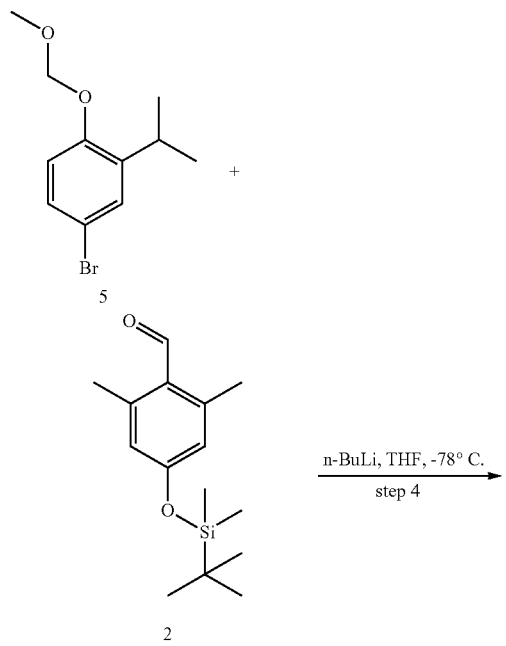

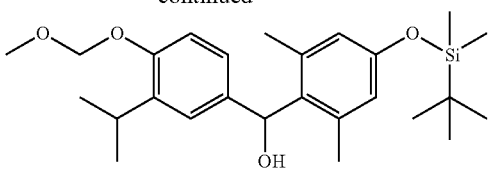

Under an argon atmosphere, to a solution of compound 5 (13 g, 50 mmol, 1.2 eq) in THF (120 mL) at −78° C. n-BuLi (2.4M, 20.8 ml, 50 mmol, 1.2 eq) was added dropwise. The solution was stirred at −78° C. for 30 minutes. A solution of compound 2 (11.1 g, 42 mmol, 1.0 eq) in THF (30 mL) was added dropwise over 30 min to the above mixture. After stirred for 1 h, the reaction was quenched with saturated aq. ammonium chloride (100 ml). After separation of layers, the aqueous phase was extracted with ethyl acetate (200 mL). The combined organic layers were washed with brine (200 mL), dried by MgSO4. The obtained residue was purified by silica gel column chromatography (ethyl acetate: n-hexane=1:100). The desired colorless transparent oily compound 6 (11.1 g, colorless liquid, yield 50%) was obtained. $^1$H NMR (400 MHZ, CDCl$_3$) δ ppm: 7.00 (s, 1H), 6.75-6.70 (m, 2H), 6.31 (s, 2H), 6.02 (s, 1H), 4.96 (s, 2H), 3.27 (s, 3H), 3.11-3.09 (m, 1H), 2.00 (s, 6H), 0.99-0.95 (m, 6H), 0.78 (s, 9H), 0.00 (s, 6H).

Step 5 Synthesis of Compound 7

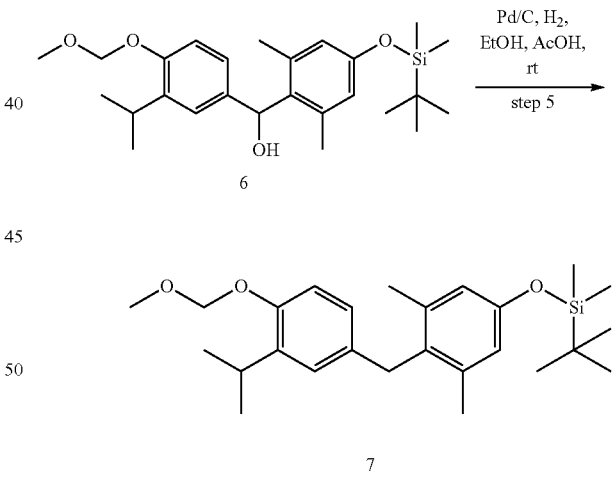

To a solution of compound 6 (11.1 g, 24.9 mmol, 1.0 eq) in EtOH/AcOH=100 (15 mL) was added 10% Pd/C (6 g), and then was treated with hydrogen. The reaction mixture was stirred at 50° C. for 5 h. The reaction mixture was filtered, and the filtrate was concentrated to give the crude product compound 7 (7.5 g, colorless oil, yield 67%) which was used directly in the next step without further purification. $^1$H NMR (400 MHz, CDCl$_3$) δ ppm: 6.93-6.88 (m, 2H), 6.68-6.66 (m, 1H), 6.56 (s, 2H), 5.15 (s, 2H), 3.91 (s, 2H), 3.48 (s, 3H), 3.30-3.27 (m, 1H), 2.18 (s, 6H), 1.18-1.16 (m, 6H), 1.00 (s, 9H), 0.21 (s, 6H).

Step 6 Synthesis of Compound 8

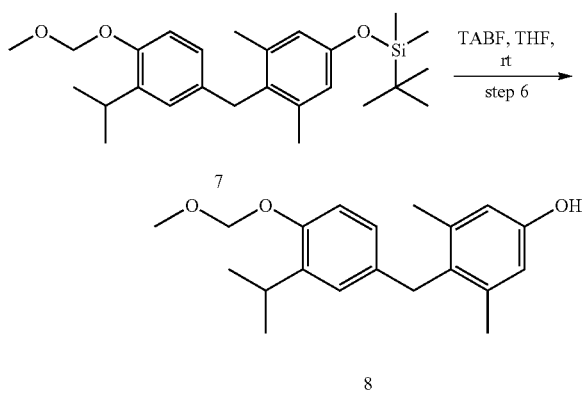

To a stirred solution of compound 7 (7.5 g, 17.5 mmol, 1.0 eq) in THF (100 mL) at 0° C. was added TBAF (6.9 g, 26.2 mmol, 1.5 eq). The reaction mixture was stirred at room temperature for 20 min, diluted with EA and washed with water (100 mL×2) and brine (100 mL×2). The solvent was removed under reduced pressure and the residue was purified by column chromatography on silica gel, eluting with EA/PE (1:4) to afford compound 8 (7.5 g, yield 75%) as an oil. LCMS: (ESI-MS): [M−H]$^+$-313.2. $^1$H NMR (400 MHZ, CDCl$_3$) δ ppm: 6.83 (s, 1H), 6.79-6.77 (m, 1H), 6.55-6.53 (m, 1H), 6.44 (s, 1H), 5.06-5.01 (m, 2H), 3.79 (s, 2H), 3.37 (s, 3H), 3.20-3.16 (m, 1H), 2.08 (s, 6H), 1.10-1.06 (m, 6H).

Example 1

2-(4-(4-hydroxy-3-isopropylbenzyl)-3,5-dimethylphenoxy)-N-(methylsulfonyl)acetamide (I1)

Step 1 Synthesis of Compound 9

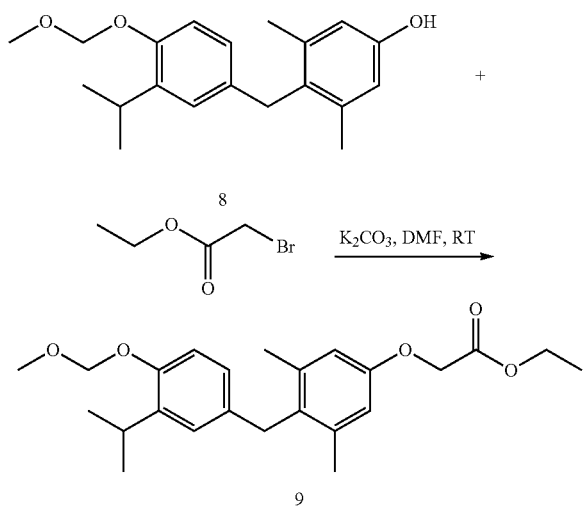

To a solution of compound 8 (630 mg, 2 mmol, 1.0 eq) and K$_2$CO$_3$ (552 mg, 4 mmol, 2.0 eq) in DMF (7 mL) at 0° C. was added ethyl bromide (368 mg, 2.2 mmol, 1.1 eq), the mixture was stirred at room temperature for 12 h. After completion of the reaction, the reaction mixture was concentrated, then diluted with water (10 mL), extracted with EA (10 mL×3). The combined organic layers were washed with brine (20 mL), dried, concentrated and purified by silica column with hexane/EA (3:1) to give the compound 9 (700 mg, oily liquid, yield 87%). $^1$H NMR (300 MHz, CDCl$_3$) δ ppm: 6.93-6.87 (m, 2H), 6.64-6.62 (m, 3H), 5.14 (s, 2H), 4.60 (s, 2H), 4.29-4.25 (m, 2H), 3.90 (s, 2H), 3.47 (s, 3H), 3.30-3.26 (m, 1H), 2.21 (s, 6H), 1.33-1.28 (m, 3H), 1.21-1.16 (m, 6H).

Step 2 Synthesis of Compound 10

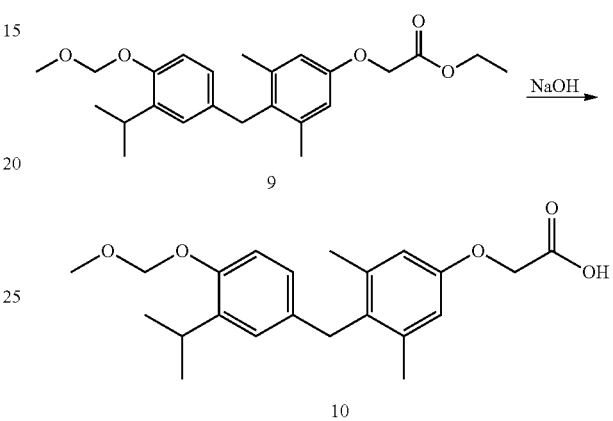

To a solution of compound 9 (700 mg, 1.75 mmol, 1.0 eq) in MeOH/THF/H$_2$O=1:1:1 (12 mL), NaOH (210 mg, 5.25 mmol, 3.0 eq) was added at rt. Themixture was stirred at room temperature for 4 h. After completion of the reaction, the reaction was acidified with 2 N HCl and a precipitate formed as the solution cooled to RT. Then the reaction was diluted with water (5 mL), extracted with EA (15 mL×2), the combined organic layers were wished with brine, dried and concentrated to give the desired product compound 10 (500 mg, white solid, yield 77%). LCMS: (ESI-MS): [M+Na]$^+$=395.1; 1H NMR (300 MHz, DMSO-d$_6$) δ ppm: 6.96 (s, 1H), 6.89-6.86 (m, 1H), 6.60 (s, 3H), 5.14 (s, 2H), 4.51 (s, 2H), 3.84 (s, 2H), 3.37 (s, 3H), 3.24-3.20 (m, 1H), 2.15 (s, 6H), 1.16-1.12 (m, 6H).

Step 3 Synthesis of Compound 11

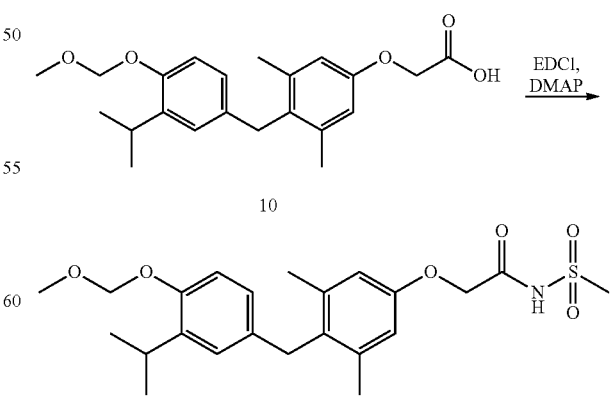

To a solution of compound 10 (500 mg, 1.34 mmol, 1.0 eq) in 20 mL of DCM, EDCI (384 mg, 2.0 mmol, 1.5 eq), Methanesulfonamide (140 mg, 1.47 mmol, 1.1 eq) and DMAP (244 mg, 2 mmol, 1.5 eq) was added at 0° C., and the resulting solution was allowed to stir for an additional 4 h at RT. After completion of the reaction, then diluted with 10% aqueous citric acid solution (20 mL), extracted with DCM (20 mL×2), and the combined organic layers were washed with brine (20 mL), dried, concentrated to give compound 11 (390 mg, Oily liquid, yield 65%). LCMS: (ESI-MS): [M+Na]$^+$=472.1; $^1$H NMR (300 MHz, CDCl$_3$) δ ppm: 6.85-6.81 (m, 2H), 6.56-6.54 (m, 2H), 5.08 (s, 2H), 4.51 (s, 2H), 3.85 (s, 2H), 3.40 (s, 3H), 3.28 (s, 2H), 3.24-3.20 (m, 1H), 2.16 (s, 6H), 1.15-1.10 (m, 6H).

Step 4 Synthesis of Compound I1

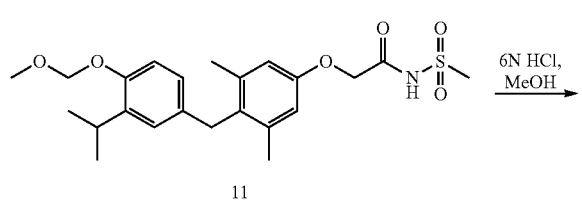

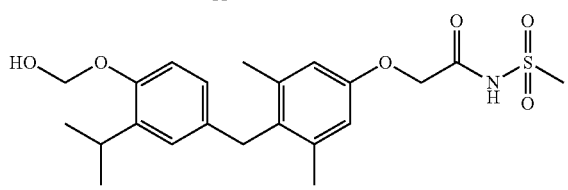

To a solution of compound 11 (390 mg, 0.87 mmol, 1.0 eq) in methanol (20 ml) was added 20 ml of 6 N HCl. The reaction mixture was stirred at room temperature overnight, diluted with water (10 ml), and extracted with ethyl acetate (2×20 ml). The combined organic extract was washed with brine (20 ml), dried over MgSO$_4$, concentrated and purified by pre-HPLC to give the compound I1 (80 mg, white solid, yield 23%). LCMS: (ESI-MS): [M−H]$^+$=404.0; $^1$H NMR (400 MHZ, DMSO-d$_6$) δ ppm: 11.97 (s, 1H), 8.97 (s, 1H), 6.85 (s, 1H), 6.62-6.60 (m, 3H), 6.47-6.45 (m, 1H), 4.64 (s, 2H), 3.80 (s, 2H), 3.28 (s, 3H), 3.15-3.11 (m, 1H), 2.17 (s, 6H), 1.11-1.10 (m, 6H).

Example 2

5-((4-(4-hydroxy-3-isopropylbenzyl)-3,5-dimethylphenoxy)methyl) isoxazol-3-ol (I2)

Step 1 Synthesis of Compound 14

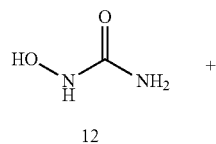

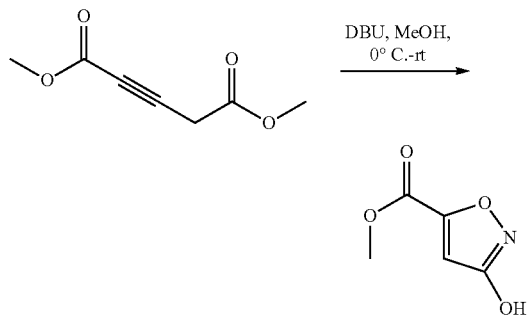

To a solution of compound 12 (3.8 g, 49.3 mmol, 1.0 eq) and DBU (9 g, 59.1 mmol, 1.2 eq) in MeOH (75 mL) at 0° C. was added compound 13 (7 g, 49.3 mmol, 1.0 eq), the mixture was stirred at 0° C. for 30 min. Then the reaction mixture was stirred at room temperature for 12 h. After completion of the reaction, the reaction mixture was diluted with water (50 mL), extracted with EA (100 mL×3). The combined organic layers were wished with brine (100 mL), dried, concentrated and purified by silica column with heptanes/EA (3:1) to give compound 14 (3 g, white solid, yield 42%). LCMS: (ESI-MS): [M+H]$^+$=144.1; $^1$H NMR (400 MHZ, DMSO-d$_6$) δ ppm: 11.92 (s, 1H), 6.76 (s, 1H), 3.87 (s, 3H).

Step 2 Synthesis of Compound 15

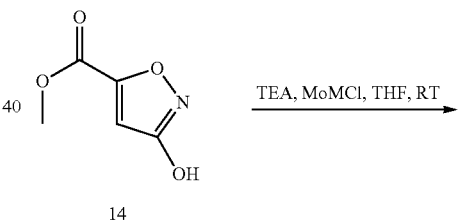

To a solution of compound 14 (1 g, 6.99 mmol, 1.0 eq) in 25 mL of THF, TEA (2.91 ml, 14 mmol, 2.0 eq), MOMCl (0.69 ml, 14 mmol, 2.0 eq) was added at 0° C., and the resulting solution was allowed to stir for an additional 2 h at RT. The reaction mixture was diluted with water (30 mL), extracted with EA (50 mL×2), and the combined organic layers were wished with brine (50 mL), dried, concentrated and purified by silica column with heptanes/EA (10:1) to give compound 15 (1 g, Oily liquid, yield 76%). LCMS: (ESI-MS): [M+H]$^+$=188.1; $^1$H NMR (300 MHz, CDCl$_3$) δ ppm: 6.57 (s, 1H), 5.29 (s, 2H), 3.87 (s, 3H), 3.49 (s, 3H).

Step 3 Synthesis of Compound 16

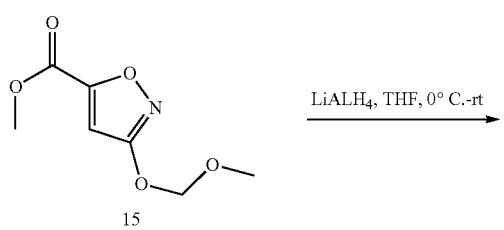

To a solution of compound 15 (1.0 g, 5.34 mmol, 1.0 eq) in THF (15 mL), LiAlH$_4$ (305 mg, 8.01 mmol, 1.5 eq) was slowly added at 0° C., and the resulting solution was allowed to stir for an additional 1 h at RT. The reaction mixture was carefully quenched with water (40 mL), extracted with EA (30 mL×2), and the combined organic layers were washed with brine (50 mL), dried, concentrated and purified by silica column with heptanes/EA (5:1) to give compound 16 (380 mg, Oily liquid, yield 45%). LCMS:(ESI-MS): [M+H]$^+$=160.1; $^1$HNMR (300 MHz, CDCl$_3$) δ ppm: 5.97 (s, 1H), 5.29 (s, 2H), 4.65 (s, 2H), 3.53 (s, 3H).

Step 4 Synthesis of Compound 17

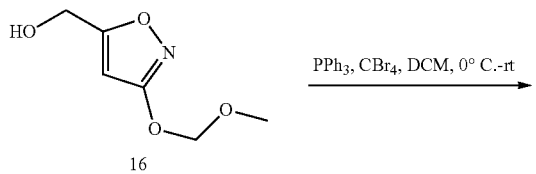

To a solution of compound 16 (380 mg, 2.4 mmol, 1.0 eq) and PPh$_3$ (940 mg, 3.6 mmol, 1.5 eq) in 10 mL of DCM at 0° C. was added CBr$_4$ (1.2 g, 3.6 mmol, 1.5 eq), then the reaction mixture was stirred at room temperature for 12 h. After completion of the reaction, the reaction mixture was concentrated and purified by silica column with heptanes/EA (3:1) to give compound 17 (120 mg crude). LCMS:(ESI-MS): [M+H]$^+$=222.0, 224.0; $^1$H NMR (400 MHZ, CDCl$_3$) δ ppm: 5.76 (s, 1H), 5.11 (s, 2H), 4.13 (s, 2H), 3.36 (s, 3H).

Step 5 Synthesis of Compound 18

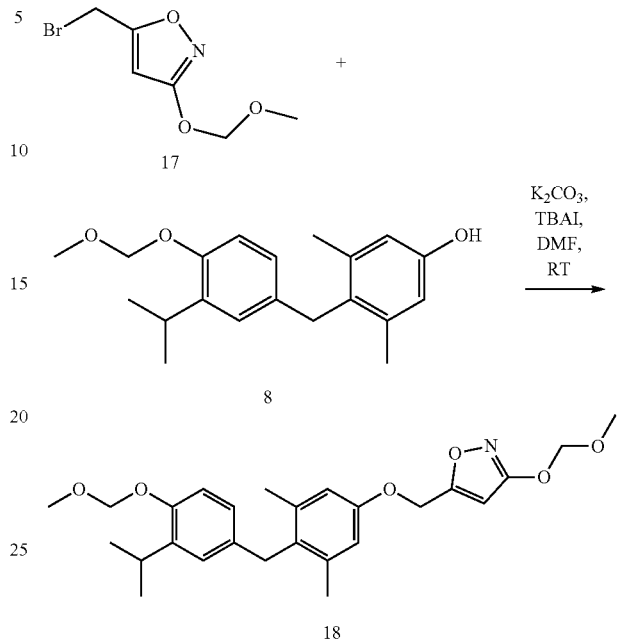

To a solution of compound 17 (120 mg, 0.54 mmol, 1.5 eq) and compound 8 (114 mg, 0.36 mmol, 1.0 eq) in toluene (3 mL) were added K$_2$CO$_3$ (110 mg, 0.79 mmol, 2.2 eq) and TBAI (8 mg, 0.02 mmol, 0.06 eq). Then the reaction mixture was stirred at room temperature for 12 h. The reaction mixture was diluted with water (10 mL), extracted with EA (10 mL×2). The combined organic layers were washed with brine (15 mL), dried, concentrated and purified by silica column with hexane/EA (1:1) to give compound 18 (80 mg, Oily liquid, yield 32%). LCMS: (ESI-MS): [M+H]$^+$=456.2; $^1$H NMR (400 MHZ, CDCl$_3$) δ ppm: 6.86-6.81 (m, 2H), 6.58-6.52 (m, 3H), 5.77 (s, 1H), 5.12-5.08 (m, 4H), 4.85 (s, 2H), 3.85 (s, 2H), 3.42-3.35 (m, 6H), 3.23-3.20 (m, 1H), 2.15 (s, 6H), 1.52 (s, 6H), 1.12-1.10 (m, 6H).

Step 6 Synthesis of Compound I2

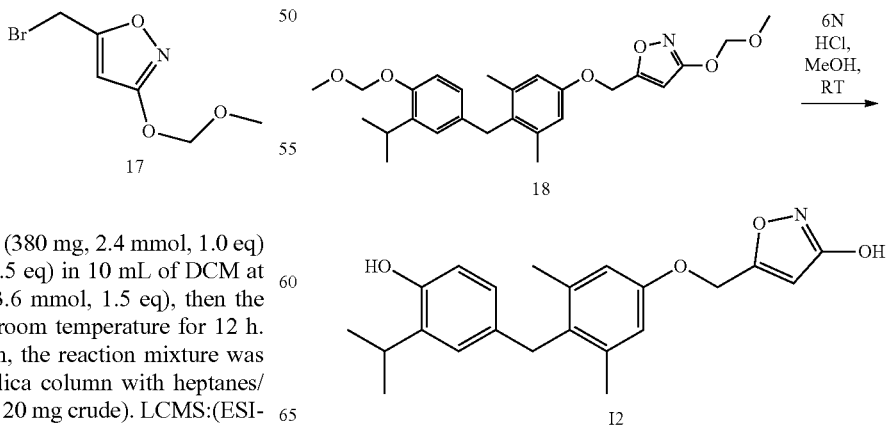

To a solution of compound 18 (80 mg, 0.17 mmol, 1.0 eq) in methanol (2 mL) was added 6 N HCl (2 mL). The reaction mixture was stirred at room temperature overnight, diluted with water (2 mL), and extracted with ethyl acetate (2×5 mL). The combined organic extracts were washed with brine (5 mL), dried over MgSO$_4$, concentrated and purified by pre-HPLC to give compound I$_2$ (24 mg, white solid, yield 40%). LCMS:(ESI-MS): [M+H]$^+$=368.2; $^1$H NMR (400 MHz, DMSO-d$_6$) δ ppm: 11.31 (s, 1H), 8.97 (s, 1H), 6.84 (s, 1H), 6.72 (s, 1H), 6.61 (d, J=8.0 Hz, 1H), 6.45 (d, J=8.4 Hz, 1H), 6.12 (s, 1H), 5.07 (s, 2H), 3.80 (s, 2H), 3.14-3.11 (m, 1H), 2.16 (s, 6H), 1.10-1.09 (m, 6H).

Example 3

2-(3,5-dichloro-4-((5-isopropyl-6-oxo-1,6-dihydropyridin-3-yl)methyl)phenyl)-3,5-dioxo-2, 3,4,5-tetrahydro-1,2,4-triazine-6-carbonitrile (13)

Step 1 Synthesis of 4-bromo-3,5-dichloroaniline (20)

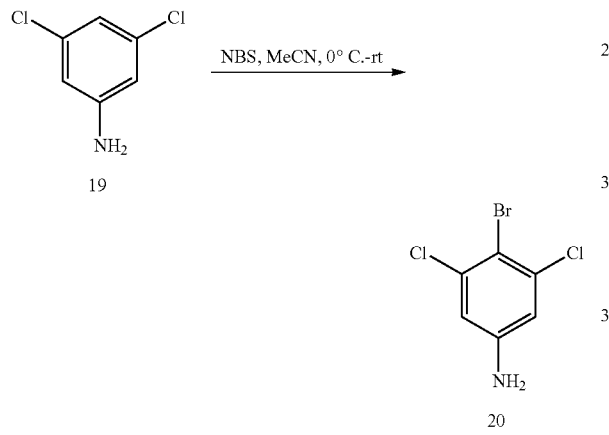

A solution of N-Bromosuccinimide (14 g, 247 mmol) in MeCN (100 mL) was added dropwise to a solution of 3,5-dichloroaniline (40 g, 247 mmol) in MeCN (300 mL) at 0° C. Then the mixture was warmed to room temperature and stirred for 3 h. After completion of the reaction, NaHCO$_3$ aq. (100 mL) was added and stirred for 15 min, then concentrated. The residue was extracted with EA (3×100 mL), the organic layers were combined and concentrated. The residue was purified by silica gel column with PE to give the desired product compound 20 (45 g, white solid, yield 76%). LCMS: (ESI-MS): [M+H]$^+$=239.9.

Step 2 Synthesis of Compound 21

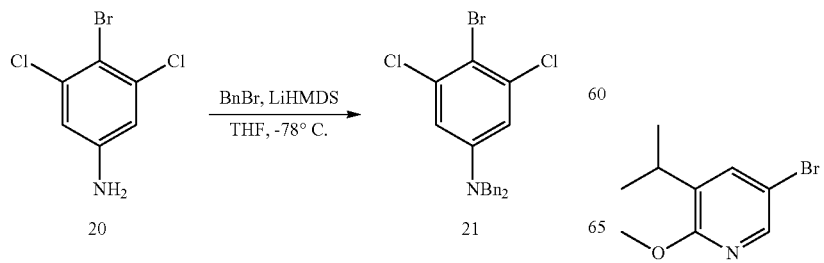

LiHMDS (55 mL, 134 mmol, 2.4 M) was added dropwise to a solution of 4-bromo-3,5-dichloroaniline (29 g, 87 mmol) in THF (300 mL) at −78° C. and stirred for 0.5 h. Then BnBr (30 g, 175 mmol) was added dropwise to the above solution. The mixture was warmed to room temperature and stirred for 2 h. After completion of the reaction, aq. NH$_4$Cl (100 mL) was added and stirred for 15 min. Then extracted with EA (3×100 mL), the organic layers were combined and concentrated. The residue was purified by silica column with PE/EA=30/1 to give the desired product 21 (25.7 g, white solid, yield 51%). $^1$H NMR (400 MHZ, DMSO-d$_6$) δ ppm 10.13 (s, 1H), 7.38 (t, J=7.3 Hz, 4H), 7.28 (dd, J=15.0, 7.3 Hz, 6H), 6.79 (s, 2H), 4.88 (s, 4H).LCMS: (ESI-MS): [M+H]$^+$=420.0.

Step 3 Synthesis of Compound 22

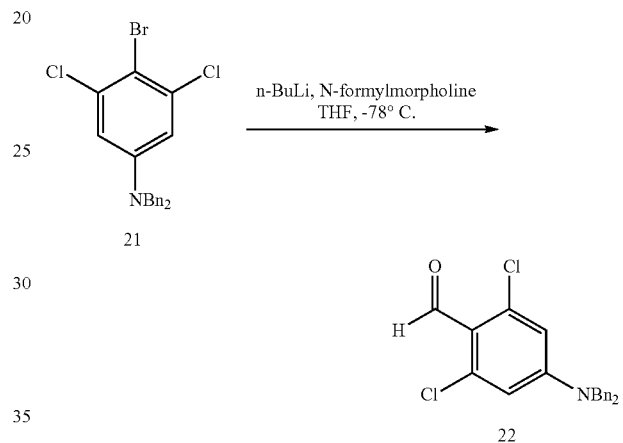

To a solution of 21 (20 g, 47 mmol, 1.0 eq) in dry THF (200 mL) was added n-BuLi (30 mL, 70 mmol, 2.4 mol/L, 1.5 eq) at −78° C. and stirred for 0.5h. Then N-formylmorpholine (10.9 g, 95 mmol, 2.0 eq) in THF (30 mL) was added at −78° C. and stirred for 1 h. Then the mixture was warmed to room temperature and stirred for overnight. After completion of the reaction, 100 mL of water was added. The mixture was extracted with EA (3×100 mL), the organic layers were combined and concentrated. The residue was purified with flash chromatography (PE:EA=10:1) to give the desired product 22 (10.2 g, white solid, yield 51%). $^1$H NMR (400 MHZ, CDCl$_3$) δ ppm 10.25 (s, 1H), 7.27 (dq, J=14.3, 7.1 Hz, 6H), 7.11 (d, J=7.2 Hz, 4H), 6.62 (s, 2H), 4.60 (s, 4H).

Step 4 Synthesis of Compound 23

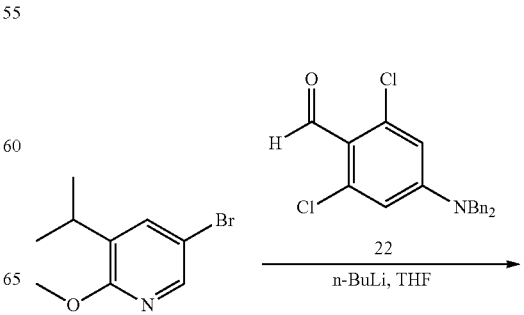

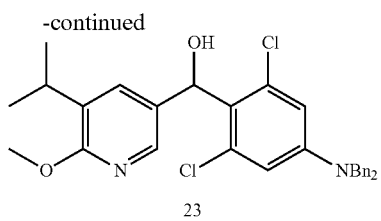

To a solution of 5-bromo-3-isopropyl-2-methoxypyridine (6.2 g, 25 mmol, 1.0 eq) in dry THF (95 mL) was added n-BuLi (12.8 mL, 30 mmol, 2.4 mol/L, 1.2 eq) at −78° C. and stirred for 0.5 h. Then compound 22 (9.5 g, 25 mmol, 1.0 eq) in THF (20 mL) was added and stirred at −78° C. for 1 h. Then the mixture was warmed to room temperature and stirred for overnight. After completion of the reaction, 100 ml of water was added and extracted with EA (3×100 mL), the organic layers were combined and concentrated. The residue was purified with flash chromatography (PE/EA=5/1) to give the desired product (5 g, white solid, yield 35%). $^1$H NMR (400 MHZ, CDCl$_3$) δ ppm 7.63 (d, J=1.3 Hz, 1H), 7.52 (d, J=1.9 Hz, 1H), 7.29 (t, J=7.3 Hz, 4H), 7.22 (t, J=7.2 Hz, 2H), 7.12 (d, J=7.3 Hz, 4H), 6.61 (s, 2H), 6.34 (d, J=10.5 Hz, 1H), 4.54 (s, 4H), 3.86 (s, 3H), 3.10-3.02 (m, 1H), 1.13 (dd, J=6.8, 4.3 Hz, 6H). LCMS:(ESI-MS): [M+H]$^+$=523.1.

Step 5 Synthesis of Compound 24

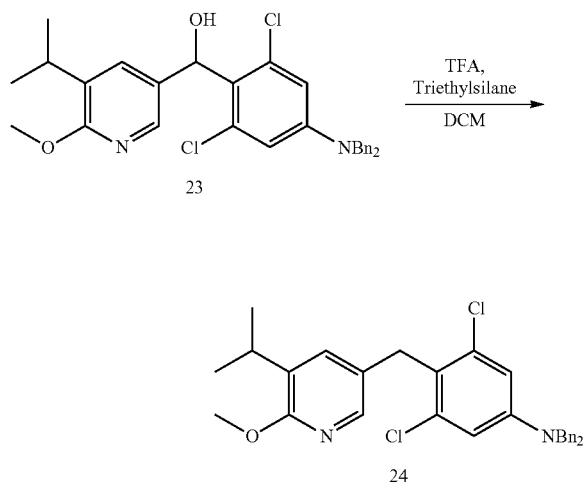

To a solution of compound 23 (1 g, 1.92 mmol, 1.0 eq) in dry THF (10 mL) was added TFA (1.1 g, 9.6 mmol, 5 eq) and triethylsilane (1.1 g, 9.6 mmol, 5 eq) at 0° C. and stirred for 0.5 h. Then the mixture was warmed to room temperature and stirred for overnight. After completion of the reaction, the reaction mixture was concentrated. The resulting residue was extracted with EA (3×50 mL), the organic layers were combined and concentrated. The residue was purified by silica column with PE/EA=1/5 to give the desired product 24 (720 mg, white solid, yield 74%). $^1$H NMR (300 MHZ, CDCl$_3$) δ ppm 7.83 (s, 1H), 7.41-7.27 (m, 7H), 7.19 (d, J=6.9 Hz, 4H), 6.70 (s, 2H), 4.59 (s, 4H), 4.12 (s, 2H), 3.92 (s, 3H), 3.14-3.09 (m, 1H), 1.19 (d, J=6.9 Hz, 6H). LCMS:(ESI-MS): [M+H]$^+$=507.1.

Step 6 Synthesis of Compound 25

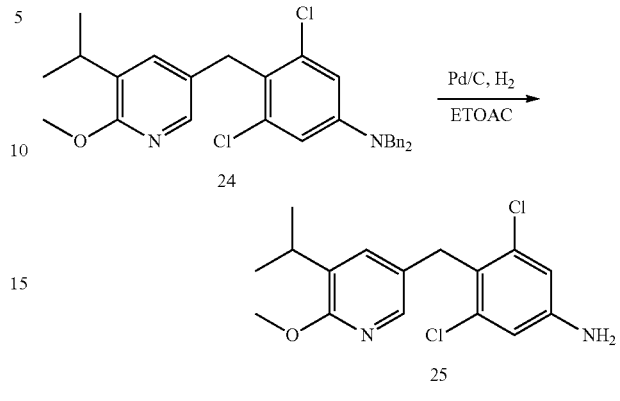

To a solution of compound 24 (1.0 g, 1.98 mmol, 1 eq.) in 10 mL of EtOAc, Pd/C (0.2 g, 20% w/w) was added and the mixture was stirred at room temperature under hydrogen. After HPLC shows the starting material was disappeared, the solid was removed by filtration and the filtrate was concentrated. The residue was purified by silica column with PE/EA=1/1 to give the desired product 25 (350 mg, white solid, yield: 54.3%). $^1$H NMR (300 MHz, CDCl$_3$) δ ppm 8.11 (s, 1H), 7.38 (s, 1H), 6.65 (s, 2H), 4.07 (s, 2H), 3.78 (s, 3H), 3.15-3.06 (m, 1H), 1.24 (d, J=9.3, 6H). LCMS:(ESI-MS): [M+H]$^+$=327.0.

Step 7 Synthesis of Compound 26

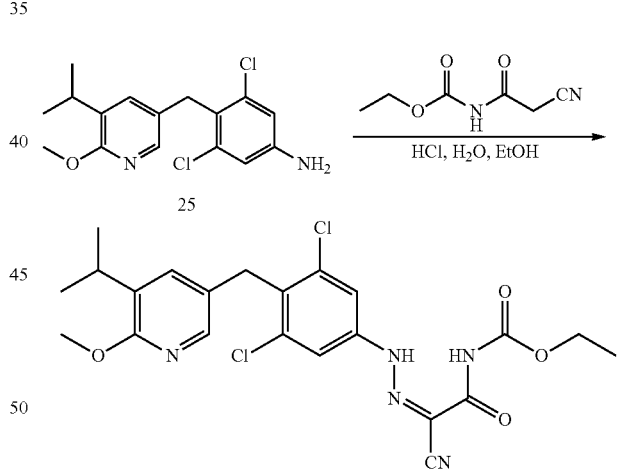

To a solution of compound 25 (350 mg, 1.07 mmol, 1.0 eq) in 4 N HCl (5 mL) was added a solution of NaNO$_2$ (104 mg, 1.5 mmol, 1.4 eq) in 1.0 mL of water dropwise at 0° C. The mixture was stirred for 30 min and a mixture of ethyl (2-cyanoacetyl) carbamate (210 mg 1.34 mmol, 1.125 eq) and NaOAc (298 mg, 3.63 mmol, 3.375 eq) in 3 mL of EtOH was added. After stirred for 40 mins, EtOH was removed under vacuum, 10 mL of water and 20 mL of DCM was added, the organic layer was concentrated to give the desired product (190 mg, yellow solid, yield: 35.8%). $^1$H NMR (400 MHz, CDCl$_3$) δ ppm 13.80 (s, 1H), 8.58 (s, 1H), 7.75 (s, 1H), 7.29 (d, J=1.5 Hz, 1H), 7.19 (s, 1H), 4.19 (dd, J=14.3, 7.2 Hz, 2H), 4.09 (d, J=11.7 Hz, 2H), 3.84 (d, J=2.2 Hz, 3H), 3.02 (dd, J=13.7, 6.9 Hz, 1H), 1.28-1.16 (m, 3H), 1.16-1.02 (m, 6H).LCMS: (ESI-MS): [M+H]$^+$=492.1.

Step 8 Synthesis of Compound 27

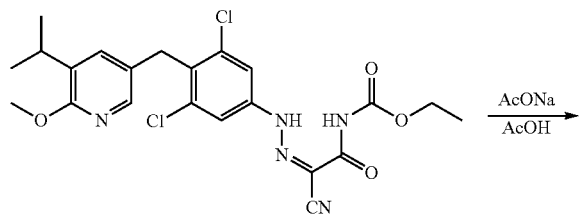

26

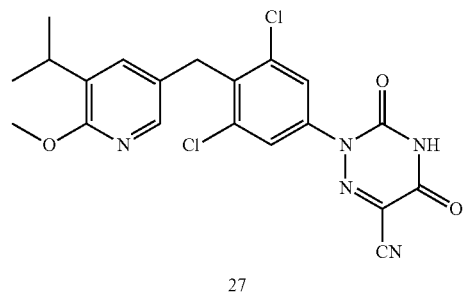

27

To a solution of compound 26 (190 mg, 0.386 mmol, 1.0 eq) in 2 mL of AcOH was added AcONa (158 mg, 1.93 mmol, 5.0 eq) and the mixture was heated to 120° C. After 1.5 h, the mixture was cooled to 0° C. and diluted with 10 mL of water. The precipitate was collected by filtration to give the desired product 27 (160 mg, white solid, yield 92.9%.) $^1$H NMR (400 MHZ, DMSO-d$_6$) δ ppm 7.77 (d, J=3.2 Hz, 1H), 7.70 (s, 2H), 7.47 (d, J=2.2 Hz, 1H), 4.24 (s, 2H), 3.84 (s, 4H), 3.06 (dp, J=13.7, 6.6 Hz, 1H), 1.14 (d, J=6.9 Hz, 6H). LCMS:(ESI-MS): [M+H]$^+$=446.3.

Step 9 Synthesis of Compound 13

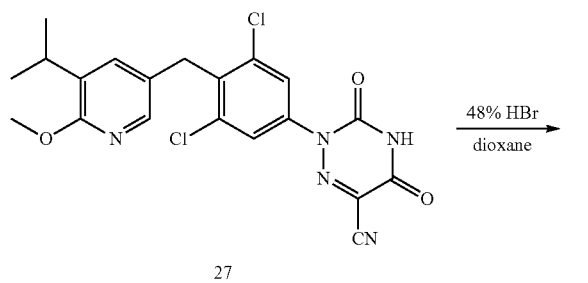

27

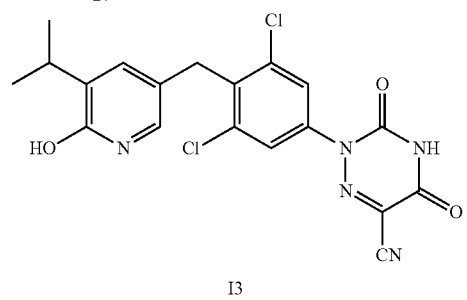

I3

To A solution of 27 (160 mg, 0.36 mmol, 1.0 eq) in 2 mL of dioxane, HBr (319 mg, 1.79 mmol, 5.0 eq, 48% aq.) was added and heated to 60° C. and stirred for 3 hours. When HPLC showed no starting material, 10 mL of water was added and the mixture was extracted with 3×10 mL of DCM. The organic layers were combined and concentrated. The residue was purified by Prep-HPLC (60% ACN in water-0.1% TFA as additive) to give desired product 13 (44 mg, white solid, yield: 28.4%). $^1$H NMR (400 MHZ, MeOD): δ ppm 7.72 (s, 2H), 7.44 (d, J=2.4 Hz, 1H), 6.96 (d, J=2.3 Hz, 1H), 4.17 (s, 3H), 3.16-3.02 (m, 1H), 1.16 (d, J=6.9 Hz, 6H).LCMS: (ESI-MS): [M+H]$^+$=432.1.

Example 4

2-(3,5-dichloro-4-((5-isopropyl-6-oxo-1,6-dihydro-pyridin-3-yl)oxy)phenyl)-3,5-dioxo-2,3,4,5-tetra-hydro-1,2,4-triazine-6-carbonitrile (I4)

Step 1 Synthesis of Compound 29

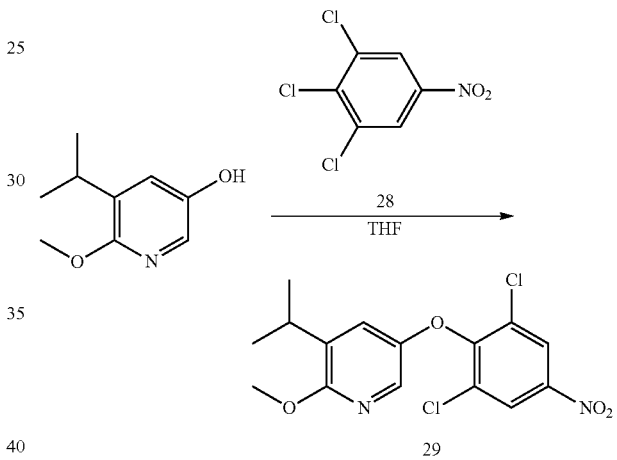

29

To a mixture of 5-isopropyl-6-methoxypyridin-3-ol (1.0 g, 5.98 mmol, 1.0 eq) and 28 (1.35 g, 5.98 mmol, 1.0 eq) in 20 mL of THF, t-BuOK (1.34 g, 11.96 mmol, 2.0 eq) was added. The mixture was stirred at 50° C. overnight under nitrogen. When HPLC showed no start material, 50 mL of water was added and extracted with 3×50 mL of EA. The organic layers were combined and concentrated. The residue was purified by slurring with MeOH to give 1.5 g of desired product 29 as yellow solid, yield: 70%. $^1$HNMR (300 MHz, CDCl$_3$-d$_3$) δ ppm: (s, 2H), 7.46 (d, J=2.4 Hz, 1H), 7.17 (d, J=2.4 Hz, 1H), 3.94 (s, 3H), 3.20-3.15 (m, 1H), 1.12 (d, J=6.8 Hz, 6H).

Step 2 Synthesis of Compound 30

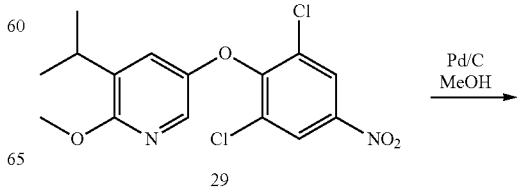

29

43

-continued

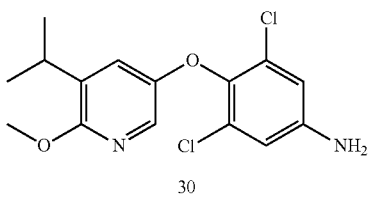

30

To a solution of 29 (1.5 g, 4.2 mmol, 1 eq.) in 15 mL of MeOH, Pd/C (0.3 g, 20% w/w) was added and the mixture was stirred at room temperature under hydrogen. After HPLC showed the start material was disappeared, the solid was removed by filtration and the filtrate was concentrated. The residue was purified with Flash chromatography (PE: EA=1:1) to give 500 mg of desired product 30 as white solid, yield: 36.3%.

Step 3 Synthesis of Compound 31

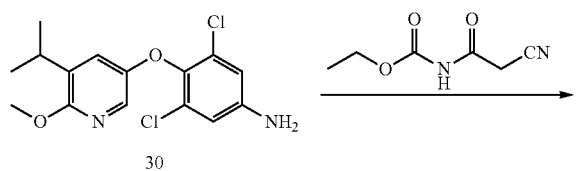

30

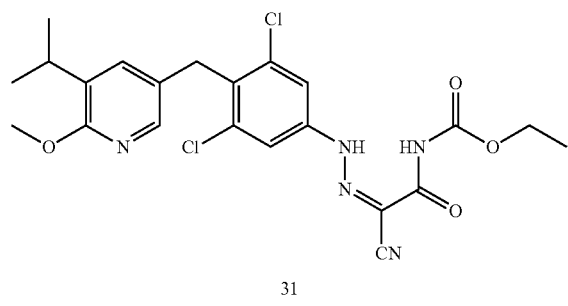

31

To a solution of 30 (480 mg, 1.47 mmol, 1.0 eq) in con. HCl (0.84 mL) and water (2.16 mL), a solution of NaNO$_2$ (141.45 mg, 2.02 mmol, 1.4 eq) in 1.08 mL of water was added by dropwise at 0° C. The mixture was stirred for 30 min and a mixture of ethyl (2-cyanoacetyl) carbamate (257.63 mg 1.65 mmol, 1.125 eq) and NaOAc (405.99 mg, 4.95 mmol, 3.375 eq) in 7.2 mL of EtOH was added. After stirred for 40 mins, EtOH was removed under vacuum, 10 mL of water and 40 mL of DCM was added, the organic layer was concentrated to give 600 mg of crude product 31, which can be used in next step without purification. $^1$HNMR (400 MHZ, CDCl$_3$-d$_3$) δ ppm: (s, 1H), 8.42 (s, 1H), 7.38-7.33 (m, 1H), 7.14 (s, 2H), 7.08 (s, 1H), 4.28 (q, J=6.8 Hz, 2H), 3.85 (s, 3H), 3.08 (s, 3H), 1.29 (t, J=6.8 Hz, 3H), 1.12 (d, J=6.8 Hz, 6H).

Step 4 Synthesis of Compound 32

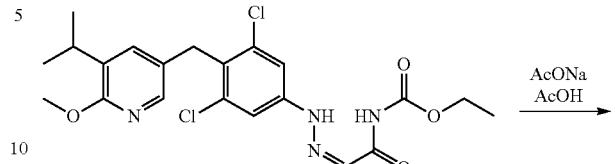

31

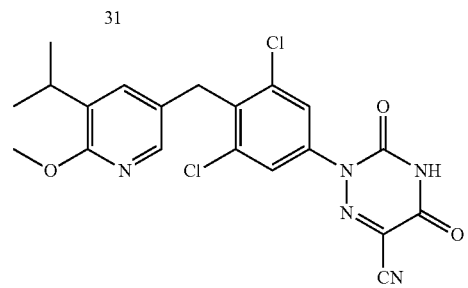

32

To a solution of 31 (600 mg, 1.2 mmol, 1.0 eq) in 12 mL of AcOH, AcONa (497.76 mg, 6.07 mmol, 5.0 eq) was added and the mixture was heated to 120° C. After 1.5h, the mixture was cooled to 0° C. and diluted with 36 mL of water. The precipitate was collected by filtration to give 430 mg of desired product 32 as white solid, two-steps yield from 30:65.3%. LCMS: [M−1]=448.0. $^1$HNMR (400 MHZ, CDCl3-d$_3$) δ ppm: 7.58 (s, 2H), 7.39 (s, 1H), 7.20 (s, 1H), 3.90 (s, 3H), 3.10-3.07 (m, 1H), 1.13 (d, J=6.8 Hz, 6H).

Step 5 Synthesis of Compound 14

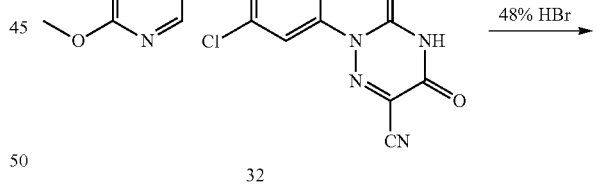

32

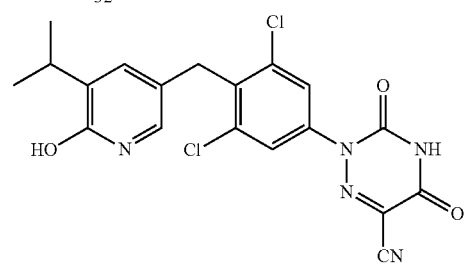

I4

To a solution of 32 (170 mg, 0.38 mmol, 1.0 eq) in 6 mL of dioxane, HBr (319 mg, 1.89 mmol, 5.0 eq, 60% aq.) was added and heated to 60° C. and stirred for 3 hours. When HPLC showed no start material, 10 mL of water was added and extracted with 3×10 mL of DCM. The organic layers were combined and concentrated. The residue was purified by Prep-HPLC (0.1% TFA and MeCN as eluent) to give 62 mg of desired product 14 as white solid, yield: 37.6%. LCMS: [M−1]=434.0. ¹HNMR (300 MHz, DMSO-d₆) δ ppm: (br, 1H), 7.78 (s, 2H), 7.71 (s, 1H), 7.27 (d, J=3 Hz, 1H), 6.70 (d, J=3 Hz, 1H), 3.02-2.97 (m, 1H), 1.13 (d, J=6.9 Hz, 6H).

Example 5

2-(3-chloro-4-((5-isopropyl-6-oxo-1,6-dihydropyridin-3-yl)oxy)phenyl)-3,5-dioxo-2,3,4,5-tetrahydro-1,2,4-triazine-6-carbonitrile (I5)

Step 1 Synthesis of Compound 33

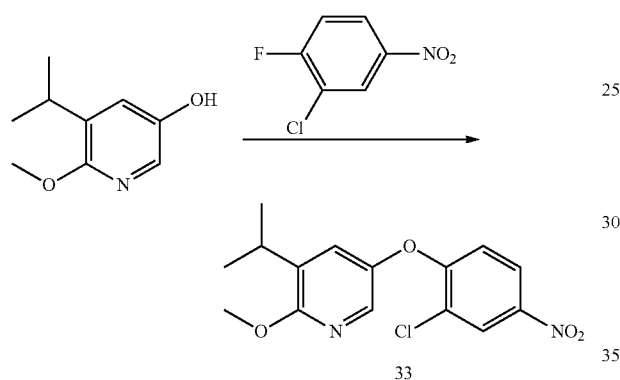

To a mixture of 5-isopropyl-6-methoxypyridin-3-ol (1.0 g, 5.95 mmol, 1.0 eq) and 2-chloro-1-fluoro-4-nitrobenzene (1.05 g, 5.95 mmol, 1.0 eq) in 20 mL of THF, was added t-BuOK (1.33 g, 11.90 mmol, 2.0 eq) at room temperature. The mixture was stirred at 50° C. overnight. When HPLC showed no start material existed, the mixture was cooled to room temperature, 50 mL of water was added and extracted with 3×50 mL of EtOAc. The organic layers were combined and concentrated. The residue was purified by silica column with PE/EA=100/1 to give the desired product 33 (890 mg, yellow solid, yield: 47%). ¹H NMR (400 MHZ, CDCl₃) δ ppm 8.31 (d, J=2.7 Hz, 1H), 7.98 (dd, J=9.1, 2.7 Hz, 1H), 7.77 (d, J=2.8 Hz, 1H), 7.17 (d, J=2.7 Hz, 1H), 6.73 (d, J=9.1 Hz, 1H), 3.92 (s, 3H), 3.14-3.11 (m, 1H), 1.14 (d, J=6.9 Hz, 6H). LCMS:(ESI-MS): [M+H]⁺=322.8.

Step 2 Synthesis of Compound 34

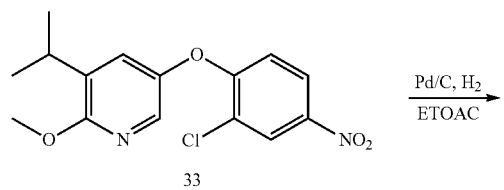

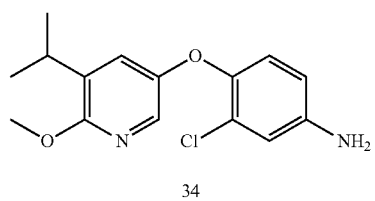

To a solution of 33 (890 mg, 2.81 mmol, 1 eq.) in EtOAc (10 mL), Pd/C (0.2 g, 20% w/w) was added and the mixture was stirred at room temperature under hydrogen. After HPLC showed the starting material was disappeared, the solid was removed by filtration and the filtrate was concentrated to give the desired product 34 (745 mg, black oil, yield: 86%). ¹H NMR (400 MHZ, CDCl₃) δ ppm 7.53 (d, J=2.9 Hz, 1H), 7.08 (d, J=2.8 Hz, 1H), 6.74-6.64 (m, 2H), 6.46 (dd, J=8.7, 2.7 Hz, 1H), 3.84 (d, J=6.0 Hz, 3H), 3.11-3.01 (m, 1H), 1.11 (d, J=6.9 Hz, 6H). LCMS:(ESI-MS): [M+H]⁺=292.9.

Step 3 Synthesis of Compound 35

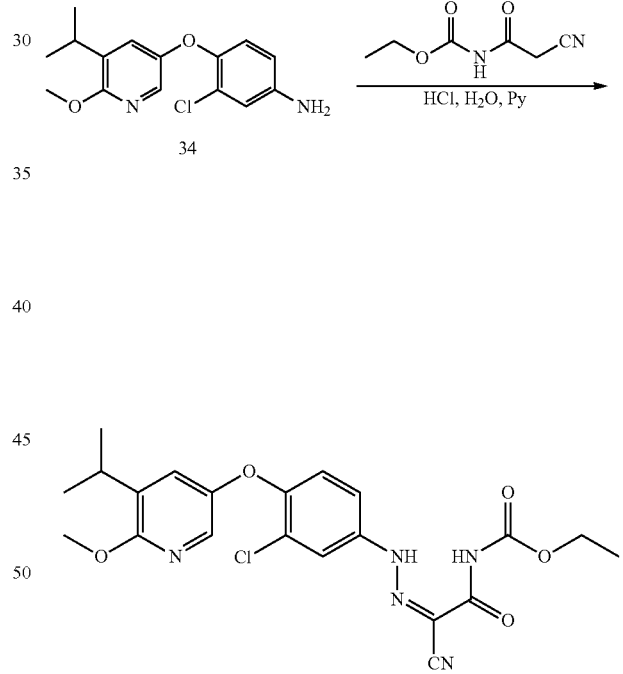

To a solution of 34 (745 mg, 2.55 mmol, 1.0 eq) in 4 N HCl (10 mL) was added a solution of NaNO₂ (246.5 mg, 3.57 mmol, 1.4 eq) in 2.0 mL of water dropwise at 0° C. The mixture was stirred for 30 min and a mixture of ethyl (2-cyanoacetyl) carbamate (448.5 mg, 2.87 mmol, 1.125 eq) in 5 mL of pyridine was added. After stirred for 40 mins, 10 mL of water and 20 mL of EtOAc was added. The organic layer was dried and concentrated to give the desired product 35 (780 mg, crude), used directly for next step. LCMS: (ESI-MS): [M+H]⁺=459.8.

Step 4 Synthesis of Compound 36

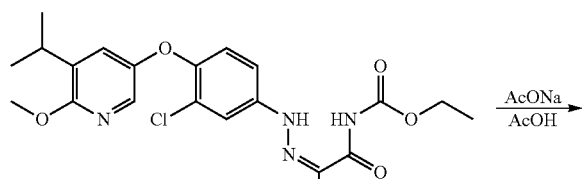

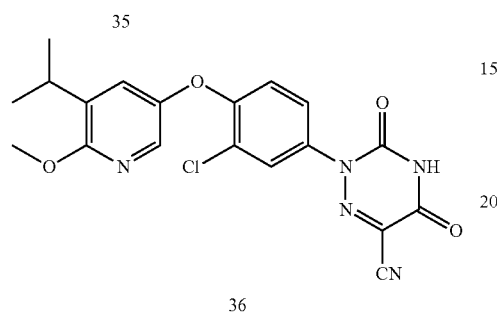

To a solution of 35 (780 mg, 1.7 mmol, 1.0 eq) in 10 mL of AcOH was added AcONa (697 mg, 8.49 mmol, 5.0 eq) and the mixture was heated to 120° C. After 1.5 h, the mixture was cooled to 0° C. and diluted with 10 ml of water, the precipitate was collected by filtration to give the desired product 36 (530 mg, crude), used directly for next step without purification. LCMS: (ESI-MS): [M+H]⁺=413.8.

Step 5 Synthesis of Compound 15

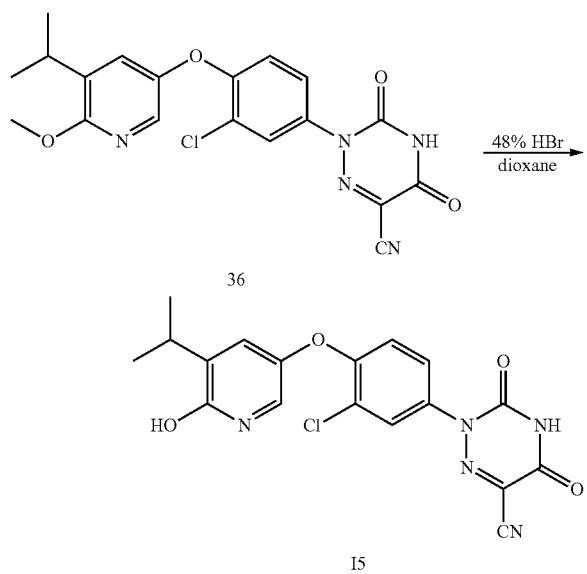

To A solution of 36 (530 mg, 1.28 mmol, 1.0 eq) in 8 mL of dioxane, HBr (2 ml, 48% aq.) was added and heated to 60° C. and stirred for 3 hours. When HPLC showed no starting material, 10 mL of water was added and to the mixture, and the mixture was extracted with 3×10 mL of EA. The organic layers were combined and concentrated. The residue was purified by Prep-HPLC (40% ACN in water- 0.1% TFA as additive) to give desired product I5 (23.8 mg, red solid, yield of 3 step: 2.3%). ¹H NMR (400 MHZ, MeOD₄) δ ppm 7.74 (d, J=2.5 Hz, 1H), 7.47 (dd, J=8.9, 2.5 Hz, 1H), 7.35 (d, J=2.9 Hz, 1H), 7.20 (d, J=3.0 Hz, 1H), 7.07 (d, J=8.9 Hz, 1H), 3.15 (dt, J=13.7, 6.8 Hz, 1H), 1.20 (t, J=8.2 Hz, 6H). LCMS: (ESI-MS): [M+H]⁺=399.8

Example 6

2-(4-((5-isopropyl-6-oxo-1,6-dihydropyridin-3-yl)oxy)-3,5-dimethylphenyl)-3,5-dioxo-2,3,4,5-tetrahydro-1,2,4-triazine-6-carbonitrile (I6)

Step 1 Synthesis of Compound 37

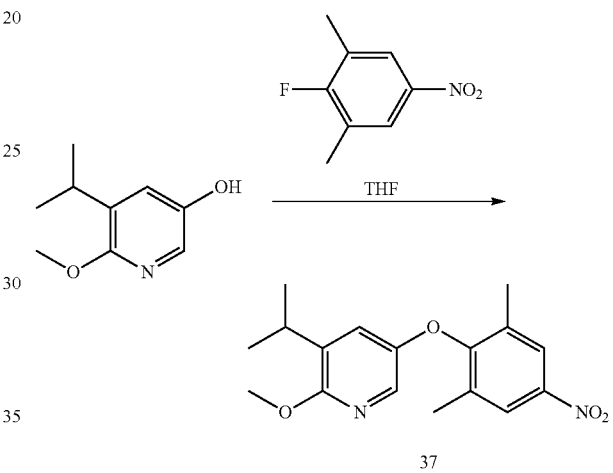

To a mixture of 5-isopropyl-6-methoxypyridin-3-ol (1.0 g, 5.98 mmol, 1.0 eq) and 2-fluoro-1,3-dimethyl-5-nitrobenzene (1.0 g, 5.98 mmol, 1.0 eq) in 20 mL of THF, t-BuOK (1.33 g, 11.90 mmol, 2.0 eq) was added. The mixture was stirred at 50° C. overnight under nitrogen. When HPLC showed no start material, water (50 mL) was added to the mixture and the mixture was extracted with EtOAc (3×50 mL). The organic layers were combined and concentrated. The residue was purified by silica column (PE/EA=100/1) to give the desired product 37 (670 mg, yield: 36%) as yellow solid. ¹H NMR (400 MHZ, CDCl₃) δ ppm 7.94 (s, 2H), 7.25 (d, J=2.9 Hz, 1H), 7.01 (d, J=2.9 Hz, 1H), 3.87 (d, J=4.2 Hz, 3H), 3.18-2.97 (m, 1H), 2.16 (d, J=4.0 Hz, 6H), 1.13 (dd, J=6.8, 4.2 Hz, 6H).LCMS: (ESI-MS): [M+H]⁺=316.9.

Step 2 Synthesis of Compound 38

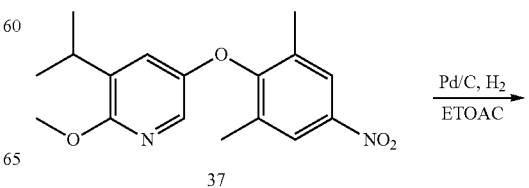

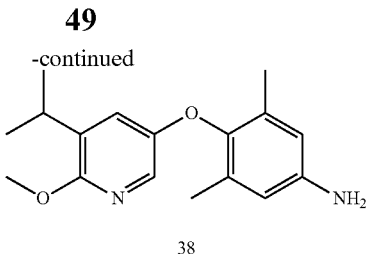

38

To a solution of 37 (890 mg, 2.81 mmol, 1 eq.) in EtOAc (10 mL), Pd/C (0.2 g, 20% w/w) was added and the mixture was stirred at room temperature under hydrogen. After HPLC showed the starting material was disappeared, the solid was removed by filtration and the filtrate was concentrated to give the desired product 38 (560 mg, yield: 69.5%) as a white solid. $^1$H NMR (400 MHz, CDCl$_3$) δ ppm 7.31 (d, J=2.9 Hz, 1H), 6.95 (d, J=2.8 Hz, 1H), 6.57 (s, 2H), 3.82 (s, 3H), 3.04 (d, J=6.9 Hz, 1H), 2.02 (d, J=10.0 Hz, 6H), 1.11 (dd, J=6.8, 2.3 Hz, 6H). LCMS:(ESI-MS): [M+H]$^+$=287.0.

Step 3 Synthesis of Compound 39

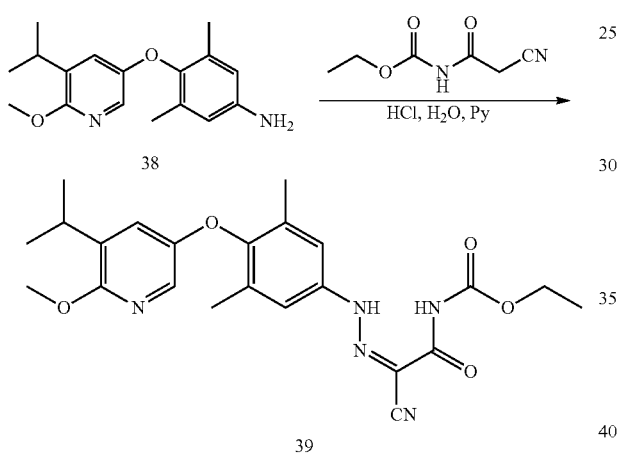

39

To a solution of 38 (550 mg, 1.92 mmol, 1.0 eq) in 4 N HCl (5 mL) was added a solution of NaNO$_2$ (185 mg, 2.69 mmol, 1.4 eq) in water (1 mL) dropwise at 0° C. The mixture was stirred for 30 min and a mixture of ethyl (2-cyanoacetyl) carbamate (338 mg, 2.16 mmol, 1.125 eq) in pyridine (3 mL) was added. After stirred for 40 mins, 10 mL of water and 20 mL of EtOAc was added. The organic layer was dried and concentrated to give the desired product 39 (810 mg, crude), which was used directly for next step without purification. LCMS:(ESI-MS): [M+H]$^+$=453.9.

Step 4 Synthesis of Compound 40

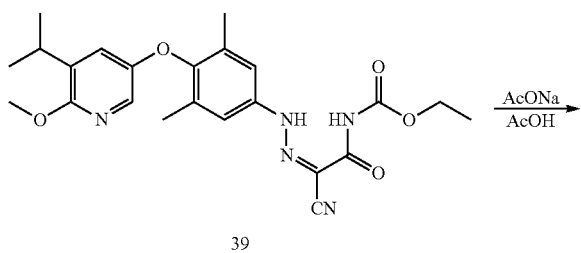

39

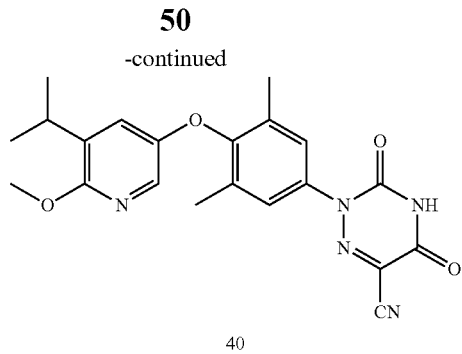

40

To a solution of 39 (810 mg, 1.79 mmol, 1.0 eq) in 10 mL of AcOH was added AcONa (733 mg, 8.93 mmol, 5.0 eq) and the mixture was heated to 120° C. After 1.5 h, the mixture was cooled to 0° C. and diluted with 10 mL of water. The precipitate was collected by filtration to give the desired product 40 (610 mg, crude), used directly for next step without purification. LCMS:(ESI-MS): [M+H]$^+$=408.0.

Step 5 Synthesis of Compound I6

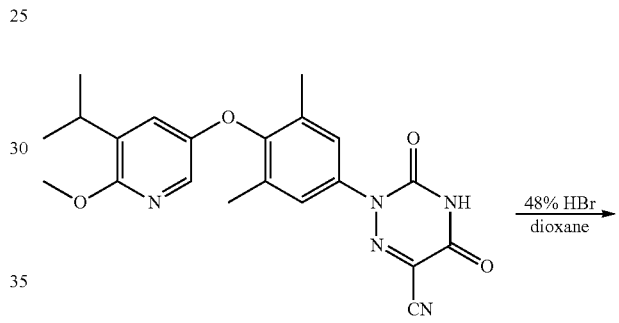

40

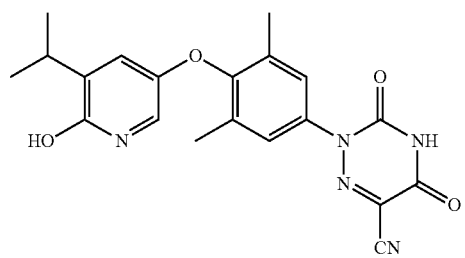

I6

To a solution of 40 (610 mg, 1.49 mmol, 1.0 eq) in 8 mL of dioxane, HBr (48% aq., 2 mL) was added and heated to 60° C. and stirred for 3h. When HPLC showed no starting material, 10 mL of water was added and extracted with 3×10 mL of EA. The organic layers were combined and concentrated. The residue was purified by Prep-HPLC (40% ACN in water-0.1% TFA as additive) to give desired product I6 (62 mg, 8.2% for 3 steps) as a white solid. $^1$H NMR (400 MHZ, DMSO) δ ppm 13.03 (s, 1H), 11.10 (brs, 1H), 7.40-7.12 (m, 3H), 6.30 (d, J=2.0 Hz, 1H), 3.08-2.89 (m, 1H), 2.16 (s, 6H), 1.13 (d, J=6.9 Hz, 6H). LCMS:(ESI-MS): [M+H]$^+$=393.8

Example 7

2-(3,5-difluoro-4-((5-isopropyl-6-oxo-1,6-dihydropyridin-3-yl)oxy)phenyl)-3,5-dioxo-2,3,4,5-tetrahydro-1,2,4-triazine-6-carbonitrile (17)

Step 1 Synthesis of Compound 41

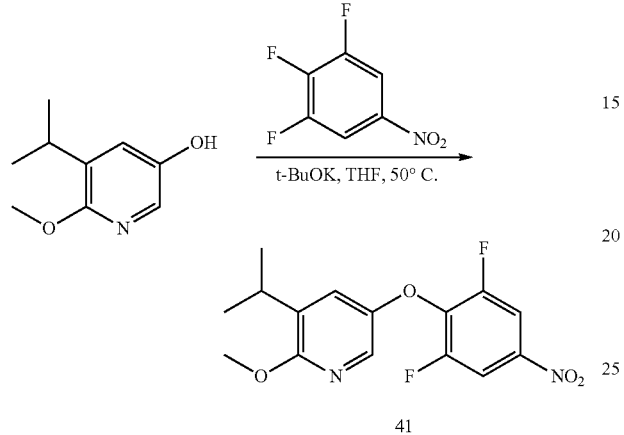

To a mixture of 5-isopropyl-6-methoxypyridin-3-ol (500 mg, 2.99 mmol, 1.0 eq) and 1,2,3-trifluoro-5-nitrobenzene (529 mg, 2.99 mmol, 1.0 eq) in THF (20 mL), t-BuOK (0.77 g, 5.98 mmol, 2.0 eq) was added, the mixture was stirred at 50° C. overnight under nitrogen. When HPLC showed no start material, water (50 mL) was added and extracted with EtOAc (3×50 mL). The organic layers were combined and concentrated. The residue was purificated by slurring with MeOH to give desired prodct41 (350 mg, yield: 36%) as a yellow solid. LCMS:(ESI-MS): [M+H]$^+$=324.8.

Step 2 Synthesis of Compound 42

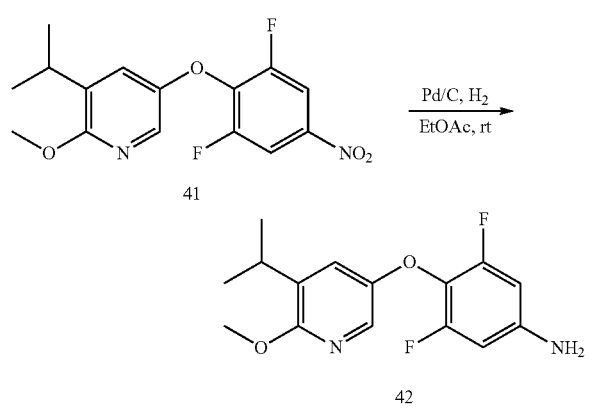

To a solution of 41 (200 mg, 0.617 mmol, 1 eq.) in EtOAc (10 mL), Pd/C (30 mg, 20% w/w) was added and the mixture was stirred at room temperature under hydrogen. After HPLC showed the starting material was disappeared, the solid was removed by filtration and the filtrate was concentrated. The residue was purified by silica column with PE/EA=1/1 to give the desired product 42 (130 mg, white solid, yield: 71%). LCMS:(ESI-MS): [M+H]$^+$=294.9.

Step 3 Synthesis of Compound 43

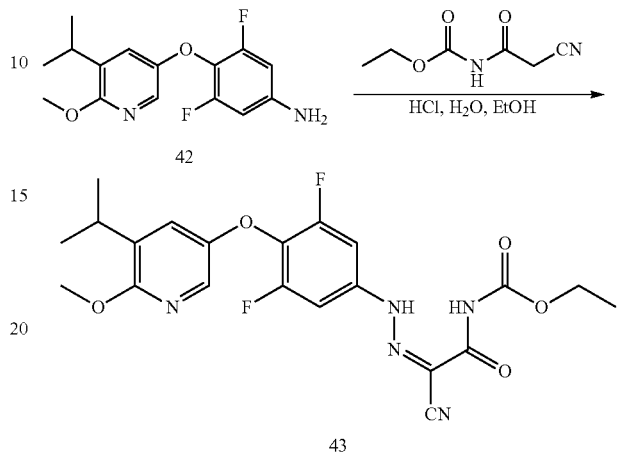

To a solution of 42 (70 mg, 0.238 mmol, 1.0 eq) in 4 N HCl (3 mL) was added a solution of NaNO$_2$ (23 mg, 0.333 mmol, 1.4 eq) in 1.0 mL of water dropwise at 0° C. The mixture was stirred for 30 min and a mixture of ethyl (2-cyanoacetyl) carbamate (41.8 mg 0.268 mmol, 1.125 eq) and NaOAc (65.88 mg, 0.80 mmol, 3.375 eq) in 2 mL of EtOH was added. After stirred for 40 mins, EtOH was removed under vacuum, 10 mL of water and 20 mL of DCM was added, the organic layer was concentrated to give the desired product 43 (39 mg, yellow solid, yield: 35.8%).

Step 4 Synthesis of Compound 44

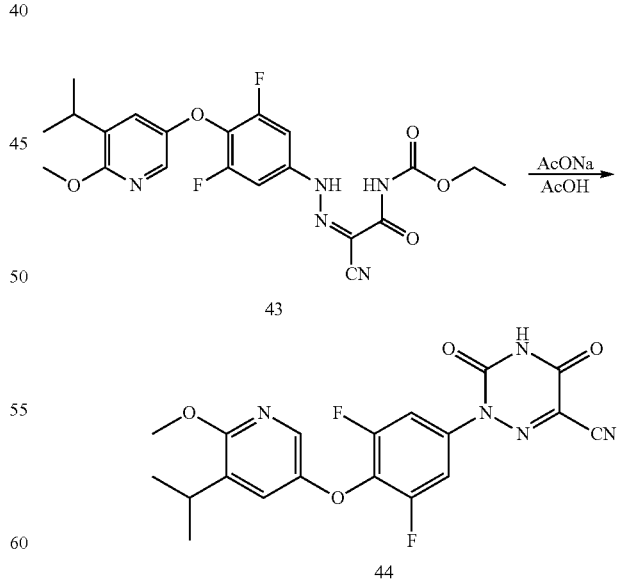

To a solution of 43 (70 mg, 0.152 mmol, 1.0 eq) in 2 mL of AcOH was added AcONa (62.32 mg, 0.76 mmol, 5.0 eq) and the mixture was heated to 120° C. After 1.5 h, the mixture was cooled to 0° C. and diluted with 10 mL of water, the precipitate was collected by filtration to give the desired product 44 (60 mg, white solid, yield 95%.). LCMS:(ESI-MS): [M+H]⁺=415.8.

Step 5 Synthesis of Compound 17

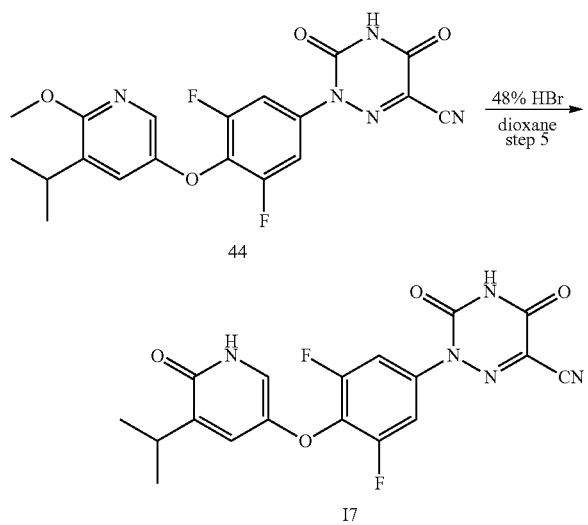

To a solution of 44 (60 mg, 0.144 mmol, 1.0 eq) in 2 mL of dioxane, HBr (1.2 ml, 0.72 mmol, 5.0 eq, 48% aq.) was added and heated to 60° C. and stirred for 3 hours. When HPLC showed no starting material, 10 mL of water was added and extracted with DCM (3×10 mL). The organic layers were combined and concentrated. The residue was purified by Prep-HPLC (40% ACN in water-0.1% TFA as additive) to give desired product I7 (3.3 mg, white solid, yield: 6.5%). ¹H NMR (400 MHZ, MeOD) δ ppm 7.45 (d, J=8.7 Hz, 2H), 7.42 (d, J=3.1 Hz, 1H), 6.99 (d, J=3.2 Hz, 1H), 3.12 (dt, J=13.7, 6.8 Hz, 1H), 1.20 (d, J=6.9 Hz, 6H). LCMS:(ESI-MS): [M+H]⁺=402.1.

Example 8

2-(3,5-dichloro-4-((3-methyl-1H-pyrrolo[2,3-b]pyridin-5-yl)oxy)phenyl)-3,5-dioxo-2,3,4,5-tetrahydro-1,2,4-triazine-6-carbonitrile (I8)

Step 1 Synthesis of Compound 46

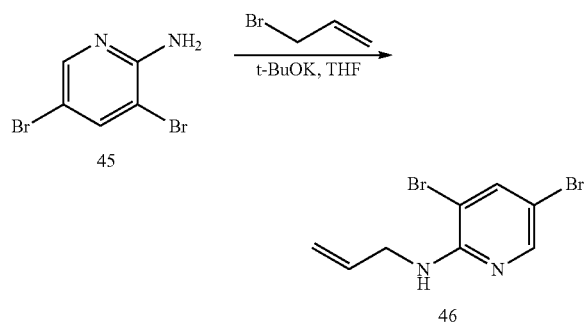

A suspension of 45 (40 g, 160 mmol, 1 eq) and t-BuOK (26.88 g, 240 mmol, 1.5 eq) in THF (400 mL) was stirred at room temperature for 1 h, then allyl bromide (21.13 g, 174.67 mmol, 1.1 eq) was dropwised. The mixture was stirred overnight at room temperature. When LCMS showed no start material, water (500 mL) was added and extracted with EtOAc (3×500 mL). The organic layers were combined and concentrated. The crude produt was chromatographed on silica gel (PE/EA=20/1) to give the compound 46 (24 g, 52%) as a colorless liquid. ¹H NMR (400 MHZ, CDCl₃) δ ppm 8.00 (d, J=2.1 Hz, 1H), 7.64 (d, J=2.1 Hz, 1H), 5.89 (m, 1H), 5.11 (m, 2H), 5.04 (s, 1H), 4.02-3.97 (m, 2H).LCMS:(ESI-MS): [M+H]⁺=292.7.

Step 2 Synthesis of Compound 47

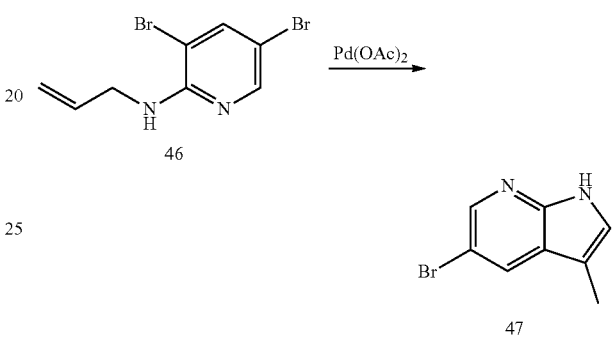

To a mixture of 46 (13 g, 44.8 mmol, 1 eq) in MeCN (200 ml) was added Pd(OAc)₂ (542 mg, 2.24 mmol, 0.05 eq), tris(2-methylphenyl)phosphine (1.64 g, 5.38 mmol, 0.12 eq) and TEA (13.6 g, 134.4 mmol, 3 eq), then the mixture was heated to reflux and stirred for 5 h. When LCMS showed no starting material, the mixture was filtered through a celite pad, and the filtrate was concentrated to give the crude product, which was purified by silica gel chromatography (PE/EA=15/1) to give 47 (4 g, 42%) as a white solid. LCMS:(ESI-MS): [M+H]⁺-212.8;

Step 3 Synthesis of Compound 48

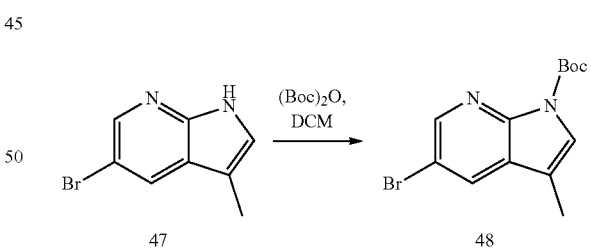

To a solution of 47 (1.4 g, 6.67 mmol, 1 eq), DMAP (81.4 mg, 0.67 mmol, 0.1 eq) and TEA (1.35 g, 13.34 mmol, 2 eq) in dichloromethane (20 mL) was added (Boc)₂O (1.74 g, 8 mmol, 1.2 eq) at room temperature. The mixture was stirred at room temperature for 2 h. The reaction mixture was poured into water and partitioned between DCM (50 mL) and water (50 mL). The organic layer was washed with brine (50 mL), dried (MgSO₄) and evaporated to dryness to afford 48 (1.2 g, 58%) as a white solid. ¹H NMR (400 MHZ, CDCl₃) δ ppm 8.44 (d, J=2.2 Hz, 1H), 7.86 (d, J=2.2 Hz, 1H), 7.34 (d, J=1.1 Hz, 1H), 2.16 (d, J=1.2 Hz, 3H), 1.58 (s, 9H). LCMS:(ESI-MS): [M+H]⁺=313.0.

Step 4 Synthesis of Compound 49

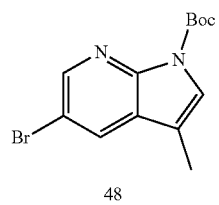

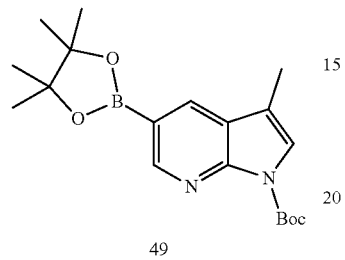

To a solution of 48 (3.5 g, 11.3 mmol, 1 eq) in dioxane (40 mL) were added KOAc (3.32 mg, 33.8 mmol, 3 eq), bis(pinacolato)diboron (8.6 g, 33.8 mmol, 3 eq) and Pd(dppf)Cl$_2$ (461 mg, 5.65 mmol, 0.05 eq). The mixture was charged with N$_2$ three times and stirred at 80° C. overnight. Then the reaction was allowed to cool to temperature and filtered through acelite pad, and the filtrate was concentrated to give the crude product 49 (5.5 g, crude) without further purification. LCMS: (ESI-MS): [M+H]$^+$=276.1.

Step 5 Synthesis of Compound 50

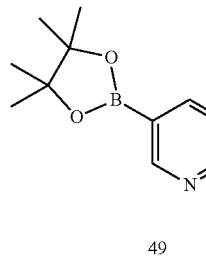

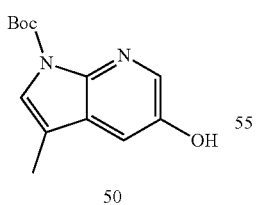

A suspension of sodium perborate tetrahydrate (8.33 g, 54.2 mmol, 3 eq) in H$_2$O (100 mL) was cooled to 0° C. and was added dropwised to a solution of 49 in THF (10 mL). After 2 h, the reaction was completed and filtered through a celite pad. The filtrate was extracted with EtOAc (3×100 mL). The organic phase was concentrated to give the crude product 50. LCMS:(ESI-MS): [M+H]$^+$=248.9.

Step 6 Synthesis of Compound 51

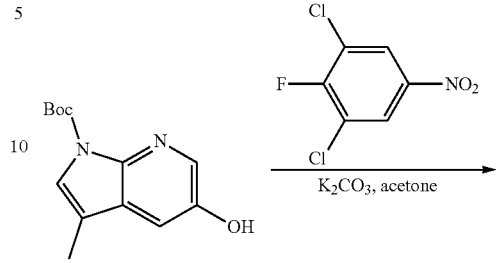

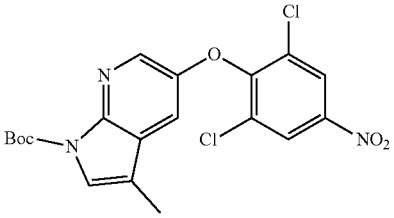

To a mixture of 50 (1.7 g, 6.88 mmol, 1.0 eq) and 1,3-dichloro-2-fluoro-5-nitrobenzene (1.45 g, 6.88 mmol, 1.0 eq) in acetone (20 mL), K$_2$CO$_3$ (1.89 g, 13.76 mmol, 2.0 eq) was added. The mixture was stirred at 50° C. for 4 h under nitrogen. When HPLC showed no start material, water (50 mL) was added to the reaction and the mixture was extracted with EtOAc (3×50 mL). The organic layers were combined and concentrated. The crude produt was chromatographed on silica gel (PE/EA=3/1) to give desired prodct 51 (2.2 g, yield: 73%) as a yellow solid. $^1$H NMR (400 MHZ, CDCl3) δ ppm 8.26 (s, 2H), 8.15 (d, J=2.6 Hz, 1H), 7.38 (s, 1H), 7.11 (d, J=2.7 Hz, 1H), 2.12 (s, 3H), 1.58 (s, 9H). LCMS:(ESI-MS): [M+H]$^+$=439.7.

Step 7 Synthesis of Compound 52

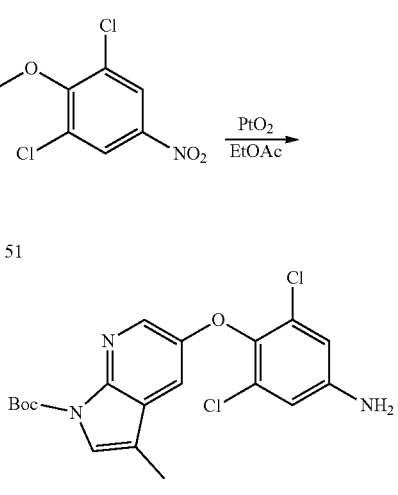

To a solution of 51 (1 g, 2.29 mmol, 1 eq) in EtOAc (15 mL), PtO$_2$ (0.1 g) was added and the mixture was stirred at room temperature under hydrogen. After HPLC shows the starting material was disappeared, the solid was removed by filtration and the filtrate was concentrated to give the desired product 52 (900 mg, yield: 95%) as a white solid. LCMS: (ESI-MS): [M+H]$^+$=409.8;

Step 8 Synthesis of Compound 53

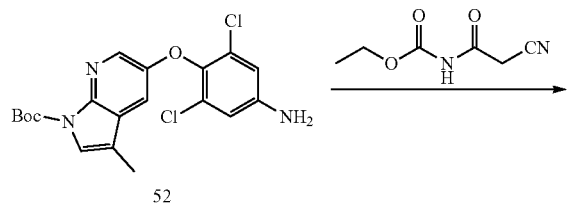

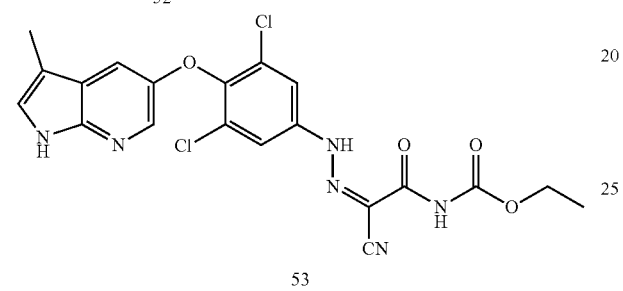

To a solution of 52 (400 mg, 0.98 mmol, 1.0 eq) in 4 N HCl (10 mL) was added dropwise a solution of NaNO$_2$ (94.7 mg, 1.37 mmol, 1.4 eq) in water (1.0 mL) at 0° C. The mixture was stirred for 30 min and a mixture of ethyl (2-cyanoacetyl) carbamate (172 mg, 1.103 mmol, 1.125 eq) in pyridine (2.0 mL) was added. After stirred for overnight, water (10 mL) and EtOAc (20 mL) was added. The organic layer was dried and concentrated to give the desired product 53 (400 mg, crude), which was used directly for next step. LCMS:(ESI-MS): [M+H]$^+$=476.7;

Step 9 Synthesis of Compound I8

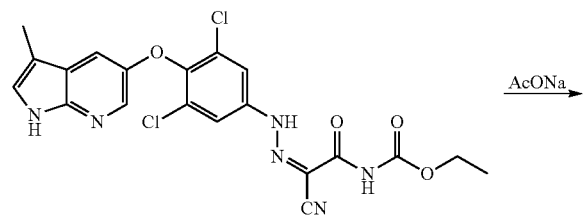

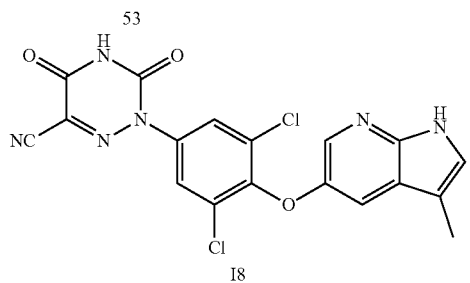

To a solution of 53 (400 mg, 0.842 mmol, 1.0 eq) in AcOH (10 mL) was added NaOAc (345 mg, 4.20 mmol, 5.0 eq) and the mixture was heated to 120° C. After 1.5 h, the mixture was cooled to 0° C. and diluted with water (10 mL), the precipitate was collected by filtration to give the crude product (380 mg, crude) which was purified by Prep-HPLC (35% ACN in water-0.1% TFA as additive) to give desired product I8 (91 mg, yield: 25%) as white a solid. $^1$H NMR (400 MHZ, DMSO) δ ppm 13.30 (s, 1H), 11.38 (s, 1H), 8.02 (t, J=12.3 Hz, 1H), 7.82 (s, 2H), 7.41-7.21 (m, 2H), 2.17 (s, 3H). LCMS:(ESI-MS): [M+H]$^+$=428.9.

Example 9

2-(4-((1H-pyrrolo[2,3-b]pyridin-5-yl)oxy)-3,5-dichlorophenyl)-3,5-dioxo-2,3,4,5-tetrahydro-1,2,4-triazine-6-carbonitrile (I9)

Step 1 Synthesis of Compound 55

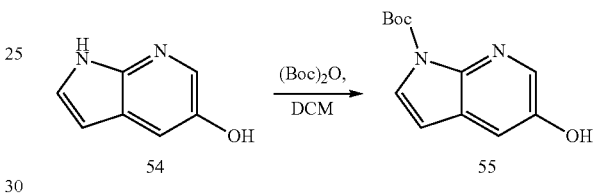

To a solution of 54 (4.8 g, 35.5 mmol, 1 eq) and DMAP (433 mg, 3.55 mmol, 0.1 eq) in DCM (50.0 mL) was added (Boc)$_2$O (23.25 g, 106.7 mmol, 3 eq), which was followed by stirring at room temperature for 4 h. Then the reaction mixture was concentrated under reduced pressure. The residue was dissolved in methanol (150 mL) and was added with potassium carbonate (24.5 g, 177.5 mmol, 5 eq), followed by stirring at room temperature for 4 h. The mixture was added with acetic acid (9.0 mL) to neutralize, and then was added with water, followed by extracting with ethyl acetate. The organic layers were combined and washed with saturated brine and dried over anhydrous sodium sulfate. The solvent was evaporated under reduced pressure. The residue was purified by flashcolumn chromatography (PE/EA=1/1) to give 55 (4 g, 47%). $^1$H NMR (400 MHZ, DMSO) δ ppm 11.29 (s, 1H), 7.83 (d, J=2.5 Hz, 1H), 7.34 (t, J=2.9 Hz, 1H), 6.26 (d, J=2.2 Hz, 1H), 1.89 (s, 9H). LCMS:(ESI-MS): [M+H]$^+$=235.1.

Step 2 Synthesis of Compound 56

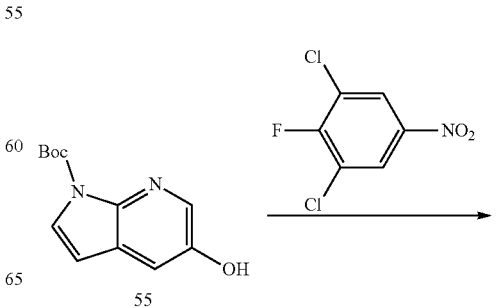

59

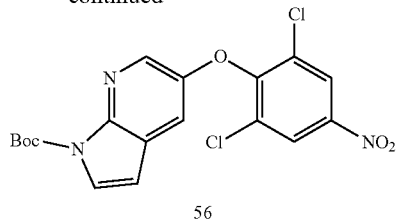

56

To a mixture of 55 (2.0 g, 8.5 mmol, 1.0 eq) and 1,3-dichloro-2-fluoro-5-nitrobenzene (1.79 g, 8.5 mmol, 1.0 eq) in THF (40 mL) was added t-BuOK (1.91 g, 17 mmol, 2.0 eq). The mixture was stirred at 50° C. overnight under nitrogen. When HPLC showed no starting material, to the mixture water (50 mL) was added and then was extracted with EtOAc (3×50 mL). The organic layers were combined and concentrated. The residue was purified by silica column (PE/EA=100/1) to give the desired product 56 (1.3 g, yellow solid, yield: 36%). LCMS:(ESI-MS): [M+H]$^+$=425.6.

Step 3 Synthesis of Compound 57

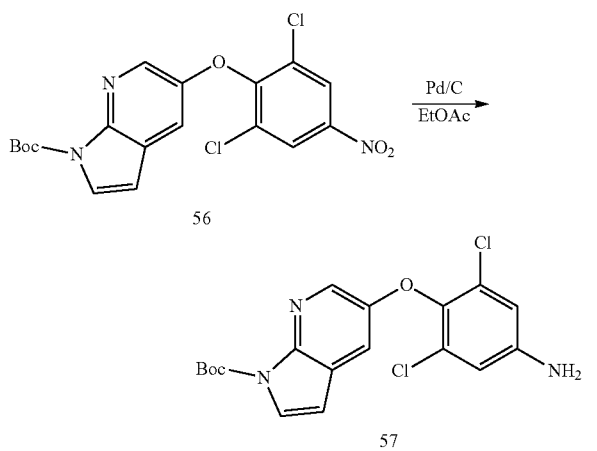

To a solution of 56 (1.2 g, 2.83 mmol, 1 eq.) in EtOAc (25 mL), Pd/C (0.2 g, 20% w/w) was added and the mixture was stirred at room temperature under hydrogen. After HPLC showed the starting material was disappeared, the precipitate was removed by filtration and the filtrate was concentrated. The residue was purified by silica gel chromatography to give the desired product 57 (180 mg, white solid, yield: 16%). LCMS:(ESI-MS): [M+H]$^+$=395.8.

Step 4 Synthesis of Compound 58

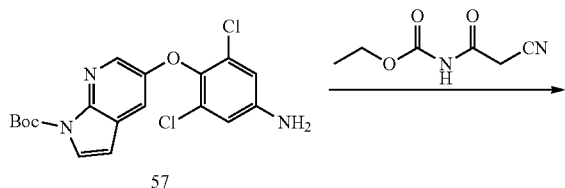

60

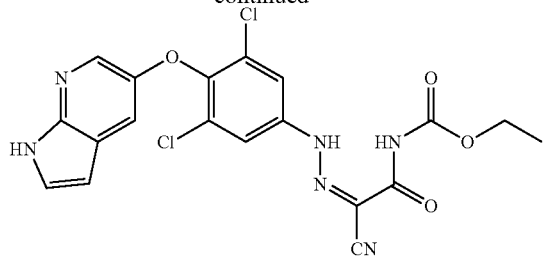

58

To a solution of 57 (180 mg, 0.456 mmol, 1.0 eq) in 4 N HCl (5 mL) was added a solution of NaNO$_2$ (46 mg, 0.667 mmol, 1.4 eq) in 1.0 mL of water dropwise at 0° C. The mixture was stirred for 30 min and a mixture of ethyl (2-cyanoacetyl) carbamate (83.67 mg, 0.536 mmol, 1.125 eq) in pyridine (1.5 mL) was added. After stirred for 40 mins, water (10 mL) and EtOAc (20 mL) was added. The organic layer was dried and concentrated to give the desired product (100 mg, crude) 58, which was used directly for next step. LCMS: (ESI-MS): [M+H]$^+$=462.9.

Step 5 Synthesis of Compound I9

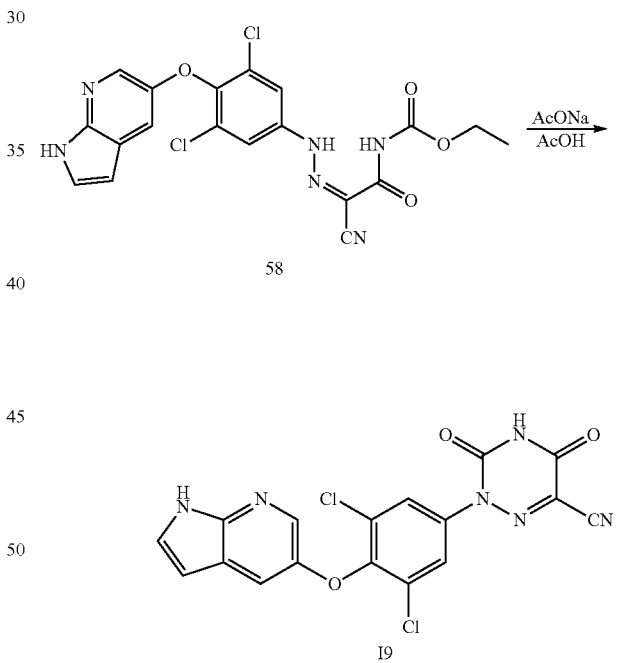

To a solution of 58 (100 mg, 0.218 mmol, 1.0 eq) in AcOH (10 mL) was added NaOAc (89.13 mg, 1.08 mmol, 5.0 eq) and the mixture was heated to 120° C. After 1.5 h, the reaction mixture was cooled to 0° C. and diluted with water (30 mL) and extracted with EtOAc (3×30 mL). The organic layer was dried and concentrated to give the crude product (30 mg), which was purified by Prep-HPLC (35% ACN in water-0.1% TFA as additive) to give the desired product I9 (1.9 mg, white solid, yield: 2.1%). $^1$H NMR (400 MHZ, MeOD) δ ppm 8.03 (s, 1H), 7.80 (s, 2H), 7.43-7.40 (m, 2H), 6.43 (d, J=3.4 Hz, 1H). LCMS:(ESI-MS): [M+H]$^+$=414.7.

Example 10

2-(3-chloro-5-fluoro-4-((5-isopropyl-6-oxo-1,6-dihydropyridin-3-yl)oxy)phenyl)-3,5-dioxo-2,3,4,5-tetrahydro-1,2,4-triazine-6-carbonitrile (I10)

Step 1 Synthesis of Compound 59

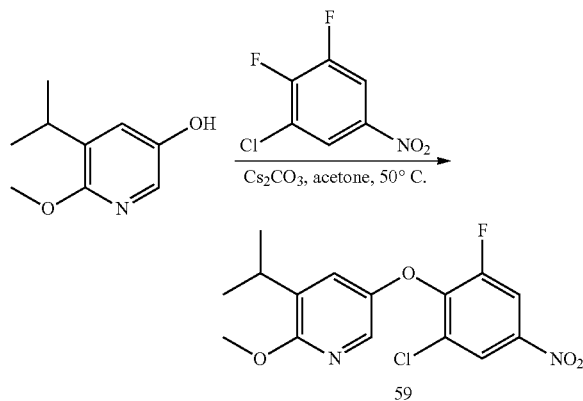

To a mixture of 5-isopropyl-6-methoxypyridin-3-ol (500 mg, 2.97 mmol, 1.0 eq) and 1-chloro-2,3-difluoro-5-nitrobenzene (574 mg, 2.97 mmol, 1.0 eq) in acetone (10 mL) was added $K_2CO_3$ (821 mg, 5.95 mmol, 2.0 eq) at room temperature. The mixture was stirred at 50° C. for 2 h. When LCMS showed no starting material, 50 mL of water was added and extracted with EtOAc (3×50 mL). The organic layers were combined and concentrated. The residue was purified by silica column with PE/EA=100/1 to give the desired product 59 (830 mg, yellow solid, yield: 82%). $^1$H NMR (400 MHZ, CDCl$_3$) δ ppm 8.22-8.11 (m, 1H), 7.93 (dd, J=9.6, 2.6 Hz, 1H), 7.52 (d, J=2.9 Hz, 1H), 7.13 (d, J=2.8 Hz, 1H), 3.86 (s, 3H), 3.09 (dt, J=13.8, 6.9 Hz, 1H), 1.13 (d, J=6.9 Hz, 6H). LCMS:(ESI-MS): [M+H]$^+$=340.8.

Step 2 Synthesis of Compound 60

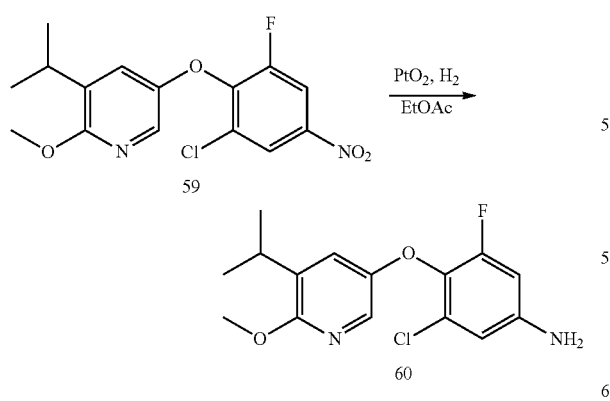

To a solution of 59 (830 mg, 2.44 mmol, 1 eq.) in EtOAc (10 mL), PtO$_2$ (0.16 g, 20% w/w) was added and the mixture was stirred at room temperature under hydrogen. After LCMS showed the starting material was disappeared, the solid was removed by filtration and the filtrate was concentrated to give the desired product 60 (640 mg, black oil, yield: 84%). $^1$H NMR (400 MHZ, CDCl$_3$) δ ppm 7.47 (d, J=2.9 Hz, 1H), 7.10 (d, J=2.9 Hz, 1H), 6.52-6.43 (m, 1H), 6.33 (dd, J=11.4, 2.6 Hz, 1H), 3.83 (s, 3H), 3.13-2.98 (m, 1H), 1.12 (d, J=6.9 Hz, 6H). LCMS: (ESI-MS): [M+H]$^+$=311.0.

Step 3 Synthesis of Compound 61

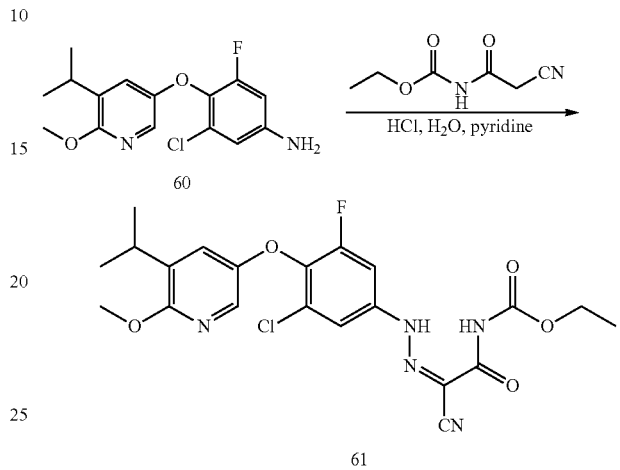

To a solution of 60 (350 mg, 1.13 mmol, 1.0 eq) in 4 N HCl (5 mL) a solution of NaNO$_2$ (109 mg, 1.58 mmol, 1.4 eq) in 2.0 mL of water was added dropwise at 0° C. The mixture was stirred for 30 min and was added a mixture of ethyl (2-cyanoacetyl) carbamate (198.4 mg, 1.27 mmol, 1.125 eq) in pyridine (2 mL). After stirred for 40 min, LCMS showed the starting material was disappeared. The mixture was diluted with water (10 mL) and EtOAc (20 mL). The organic layer was dried and concentrated to give the desired product 61 (430 mg, crude), used directly for next step. LCMS: (ESI-MS): [M+H]$^+$=478.0.

Step 4 Synthesis of Compound 62

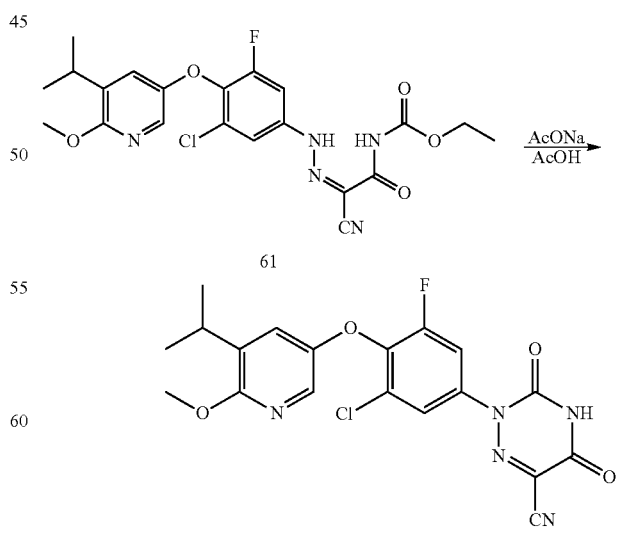

To a solution of 61 (430 mg, 0.9 mmol, 1.0 eq) in 5 mL of AcOH was added AcONa (369.6 mg, 4.5 mmol, 5.0 eq) and the mixture was heated to 120° C. After 1.5 h, LCMS showed the starting material was disappeared. The mixture was cooled to 0° C. and diluted with water (10 mL), the precipitate was collected by filtration to give the desired product 62 (460 mg, crude), which was used directly for next step without purification. LCMS:(ESI-MS): [M+H]⁺=431.8

Step 5 Synthesis of Compound I10

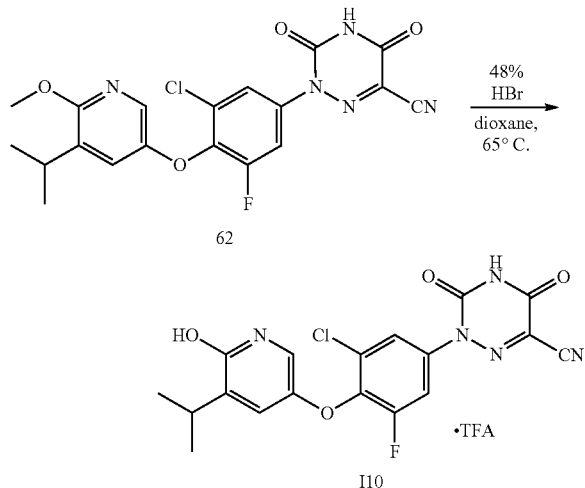

To a solution of 62 (460 mg, 1.06 mmol, 1.0 eq) in dioxane (8 mL), was added HBr (2 mL, 48% aq.) The reaction mixture was heated to 60° C. and stirred for 5 hours. When HPLC showed no starting material existed, the mixture was diluted with water (10 mL) and extracted with EtOAc (3×10 mL). The organic layers were combined and concentrated. The residue was purified by Prep-HPLC (40% ACN in water-0.1% TFA as additive) to give desired product I10 (81 mg, red solid, 17% for 3 steps). $^1$H NMR (400 MHZ, DMSO) δ ppm 13.24 (s, 1H), 7.64-7.60 (m, 2H), 7.29 (d, J=3.1 Hz, 1H), 6.93 (d, J=2.8 Hz, 1H), 3.04-2.94 (m, 1H), 1.12 (d, J=6.9 Hz, 6H). LCMS:(ESI-MS): [M+H]⁺=417.9.

Example 11

2-(3,5-dichloro-4-((5-cyclopropyl-6-oxo-1,6-dihydropyridin-3-yl)oxy)phenyl)-3,5-dioxo-2,3,4,5-tetrahydro-1,2,4-triazine-6-carbonitrile (I11)

Step 1 Synthesis of Compound 63

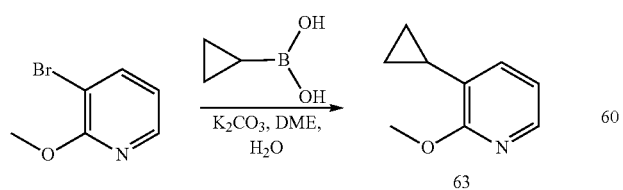

To a mixture of 3-bromo-2-methoxypyridine (20 g, 0.11 mmol, 1.0 eq), cyclopropylboronic acid (13.7 g, 0.16 mmol, 1.5 eq) and K₂CO₃ (73.4 g, 0.53 mmol, 5.0 eq) in DME (200 mL) and H₂O (40 mL) was added Pd(dppf)Cl₂—CH₂Cl₂ (8.68 g, 0.01 mmol, 0.1 eq) and the mixture was charged with N₂ three times and stirred at 80° cover night under nitrogen. After TLC showed the start material was disappeared, the mixture was cooled to room temperature and water (100 ml) was added. The mixture was extracted with EtOAc (4×100 mL), the organic layers were combined and concentrated. The residue was purificated by silica gel column chromatography (PE) to give the desired product 63 (11.8 g, yield: 74%) as brown oil. $^1$HNMR (400 MHZ, CDCl₃) δ ppm 7.89 (dd, J=4.9, 1.4 Hz, 1H), 7.03 (dd, J=7.3, 1.1 Hz, 1H), 6.71 (dd, J=7.2, 5.0 Hz, 1H), 3.92 (s, 3H), 1.99 (ddd, J=8.4, 5.1, 3.2 Hz, 1H), 0.92-0.82 (m, 2H), 0.63-0.48 (m, 2H). LCMS: [M+1]=149.9.

Step 2 Synthesis of Compound 64

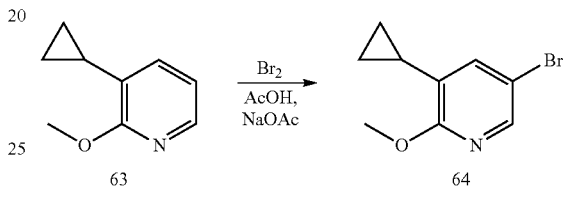

To a solution of 63 (6.5 g, 43.6 mmol, 1.0 eq) and NaOAc (7.87 g, 95.97 mmol in AcOH (70 mL, 2.2 eq) was added Br₂ (6.28 g, 39.26 mmol, 0.9 eq) at room temperature, the mixture was stirred for 30 min. After HPLC showed no start material, water (300 mL) was added, the mixture was extracted with EtOAc (4×100 mL), washed by sodium bicarbonate solution. The organic layers were combined and concentrated. The residue was purificated by silica gel column chromatography (PE) to give 3.9 g of desired product 64 as oil, yield: 39%. $^1$HNMR (400 MHZ, CDCl₃) δ ppm 8.00 (d, J=2.3 Hz, 1H), 7.18 (d, J=2.3 Hz, 1H), 3.97 (s, 3H), 2.08-2.01 (m, 1H), 1.09-0.90 (m, 2H), 0.75-0.59 (m, 2H).LCMS: [M+1]=227.8.

Step 3 Synthesis of Compound 65

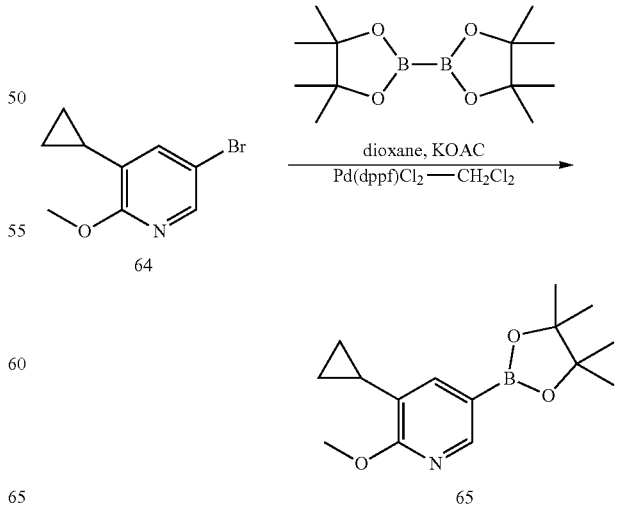

To a solution of 64 (2 g, 8.7 mmol, 1.0 eq), KOAc (2.58 mL, 26.3 mmol, 3.0 eq) and bis(pinacolato)diboron (6.68 g, 26.3 mmol, 3.0 eq) in dry dioxane (20 mL) was added Pd(dppf) Cl2-CH$_2$Cl$_2$ (358 mg, 0.44 mmol, 0.05 eq). The mixture was stirred at 80° C. overnight under N$_2$. After LCMS showed no start material, the solid was removed by filtration and washed with EtOAc (3×20 mL), the organic layers were combined and concentrated to give the desired product 65 (2.4 g, crude), which was used directly for next step. LCMS: [M+1]=276.1.

Step 4 Synthesis of Compound 66

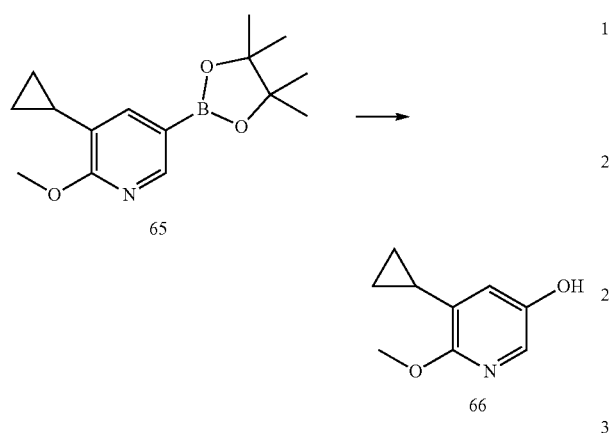

To a solution of sodium perborate tetrahydrate (4.1 g, 26.64 mmol, 3.0 eq) in water (40 mL) was added dropwise a solution of 65 (2.4 g, crude) in THF (30 mL) at 0° C. The mixture was then stirred at room temperature for 3 h. After LCMS showed no starting material, the solid was removed by filtration and the filtrate was extracted with EtOAc (4×30 mL). The organic layers were combined and concentrated. The residue was purificated by flash chromatography (C18 column, 5% to 90% ACN in water) to give the desired product 66 (1.0 g, brown gum, 69% yield for 2 steps). $^1$H NMR (400 MHZ, CDCl$_3$) δ ppm 7.52 (d, J=2.4 Hz, 1H), 6.66 (d, J=2.4 Hz, 1H), 3.88 (s, 3H), 2.06-1.87 (m, 1H), 0.96-0.81 (m, 2H), 0.64-0.48 (m, 2H).LCMS: [M+1]=165.9.

Step 5 Synthesis of Compound 67

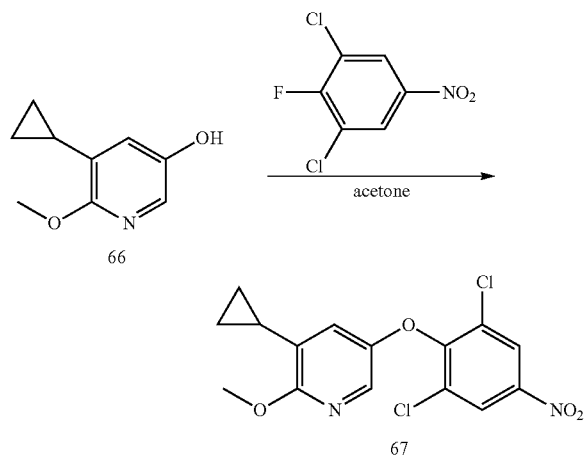

To a mixture of 66 (1.0 g, 6.06 mmol, 1.0 eq) and 1,3-dichloro-2-fluoro-5-nitrobenzene (1.27 g, 6.06 mmol, 1.0 eq) in acetone (20 mL) was added K$_2$CO$_3$ (1.67 g, 12.12 mmol, 2.0 eq) at room temperature. The mixture was stirred at 50° C. overnight under nitrogen. When LCMS showed no starting material, water (50 mL) was added and extracted with EtOAc (3×50 mL). The organic layers were combined and concentrated. The residue was purified by silica column (PE/EA=50/1) to give the desired product 67 (1.3 g, yellow solid, yield: 61%). $^1$H NMR (400 MHZ, DMSO) δ ppm 8.52 (s, 2H), 7.51 (d, J=2.9 Hz, 1H), 7.04 (d, J=2.9 Hz, 1H), 3.86 (s, 3H), 2.12-1.90 (m, 1H), 1.08-0.85 (m, 2H), 0.79-0.58 (m, 2H). LCMS:(ESI-MS): [M+H]$^+$=356.7.

Step 6 Synthesis of Compound 68

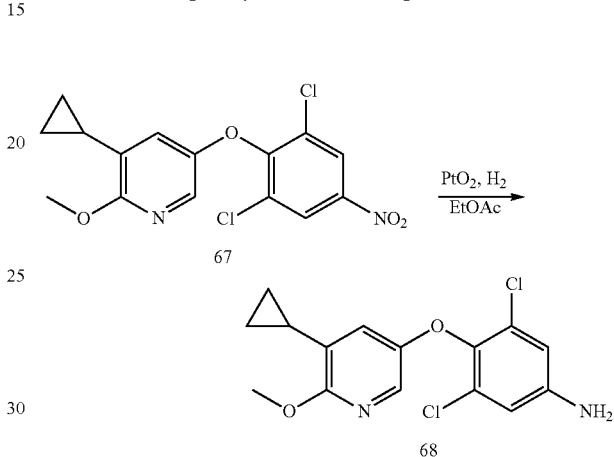

To a solution of 67 (620 mg, 1.75 mmol, 1 eq) in EtOAc (10 mL) was added PtO$_2$ (0.12 g, 20% w/w) and the mixture was stirred at room temperature under hydrogen. After LCMS showed the starting material was disappeared, the solid was removed by filtration and the filtrate was concentrated to give the desired product 68 (530 mg crude, yellow solid). $^1$H NMR (400 MHZ, DMSO) δ ppm 7.37 (d, J=2.9 Hz, 1H), 6.92 (d, J=2.8 Hz, 1H), 6.75 (s, 2H), 5.71 (s, 2H), 3.89 (s, 3H), 2.04 (dd, J=9.4, 4.0 Hz, 1H), 1.05-0.88 (m, 2H), 0.78-0.61 (m, 2H).LCMS: (ESI-MS): [M+H]$^+$=327.0.

Step 7 Synthesis of Compound 69

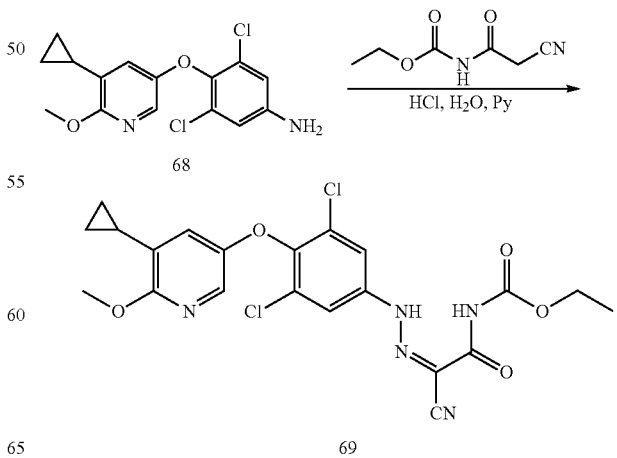

To a solution of 68 (530 mg, 1.63 mmol, 1.0 eq) in 4 N HCl (10 mL) at 0° C. was added a solution of NaNO₂ (158 mg, 2.29 mmol, 1.4 eq) in 1.0 mL of water dropwise. The mixture was stirred for 30 min and was added dropwise a solution of ethyl (2-cyanoacetyl) carbamate (287.5 mg, 1.84 mmol, 1.125 eq) in pyridine (3 mL). After stirred for 40 min, LCMS showed the starting material was disappeared; the mixture was diluted with water (10 mL) and EtOAc (20 mL). The organic layer was dried and concentrated to give the desired product 69 (340 mg, crude), which was used directly for next step without purification. LCMS: (ESI-MS): [M+H]⁺=493.7.

Step 8 Synthesis of Compound 70

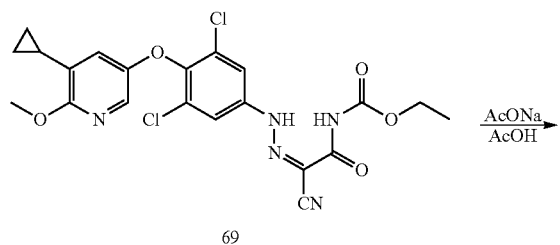

To a solution of 69 (340 mg, 0.691 mmol, 1.0 eq) in AcOH (5 mL) was added AcONa (283 mg, 3.45 mmol, 5.0 eq). The mixture was heated to 120° C. After 1.5 h, LCMS showed the starting material was disappeared, the mixture was cooled to 0° C. and diluted with water (10 mL), the precipitate was collected by filtration to give the desired product 70 (400 mg, crude), used directly for next step without purification. LCMS:(ESI-MS): [M+H]⁺=447.7

Step 9 Synthesis of Compound I11

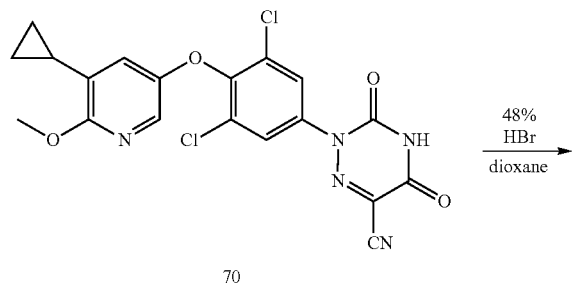

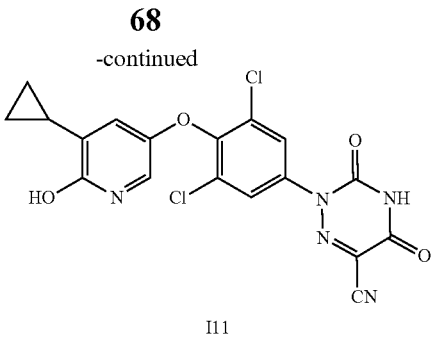

To A solution of 70 (400 mg, 0.928 mmol, 1.0 eq) in 8 mL of dioxane, was added HBr (2 mL, 48% aq) and heated to 60° C. and stirred for 3 hours. When HPLC showed no starting material, water (10 mL) was added and extracted with EtOAc (3×10 mL). The organic layers were combined and concentrated. The residue was purified by Prep-HPLC (60% ACN in water-0.1% TFA as additive) to give desired product 111 (47 mg, yellow white solid, 6.6% for 3 step). ¹H NMR (400 MHZ, DMSO-d₆) δ ppm 13.26 (s, 1H), 11.27 (s, 1H), 7.77 (s, 2H), 7.02 (d, J=3.1 Hz, 1H), 6.64 (s, 1H), 1.99 (dd, J=9.4, 4.2 Hz, 1H), 0.96-0.78 (m, 2H), 0.72 (q, J=6.0 Hz, 2H). LCMS:(ESI-MS): [M+H]⁺=433.7

Example 12

2-(3,5-dichloro-4-((3-methyl-1H-indol-5-yl)oxy) phenyl)-3,5-dioxo-2,3,4,5-tetrahydro-1,2,4-triazine-6-carbonitrile (112)

Step 1 Synthesis of Compound 72

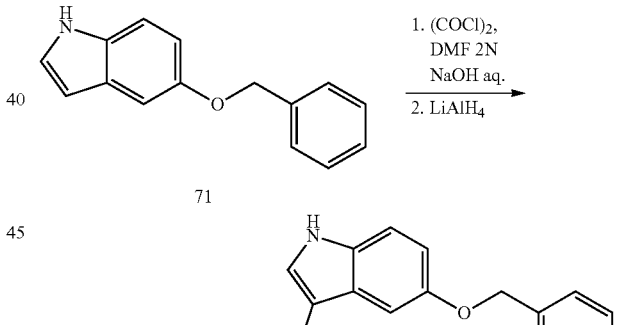

Oxalyl chloride (12.12 g, 95.5 mmol, 0.71 eq) was added in a dropwise manner to DMF (200 mL) under stirring at 0° C. The mixture was allowed to warm up to room temperature and stirred for 1 h. After cooling down to 0° C., a solution of 71 (30 g, 134.5 mmol, 1 eq) in DMF (150 mL) was added dropwise. The resulting reaction mixture was stirred at room temperature for 5h, and then sodium hydroxide solution (25 mL) was added. The reaction mixture was stirred at 100° C. for 10 min. After cooling to room temperature, the mixture was extracted with ethyl acetate. The combined organic layer was washed with brine, dried over anhydrous Na₂SO₄, and concentrated under reduced pressure. The residue was purified by recrystallization (using petroleum ether and ethyl acetate as the extractant) to give an aldehyde product (12 g, crude).A solution of the resulting aldehyde product (12 g, crude) in THF (60 mL) was added dropwise to amixture of LiAlH$_4$ (3.8 g, 10 mmol) in redistilled dry THF (150 mL) in a dried round flask. After the mixture was stirred at room temperature overnight, water (3.8 mL) was added carefully and the reaction mixture was stirred for 5 min. The resulting solid was removed by filtration and washed with ethyl acetate. The combined organic layers were washed with brine, dried over anhydrous Na$_2$SO$_4$ and concentrated under reduced pressure. The residue was purified by silica gel flash chromatography (PE:EA=3:1) to afford the 72 (5.2 g, 16.3%). $^1$H NMR (400 MHZ, CDCl$_3$) δ ppm 7.71 (s, 1H), 7.42 (d, J=7.4 Hz, 2H), 7.32 (t, J=7.4 Hz, 2H), 7.25 (t, J=7.2 Hz, 1H), 7.18 (s, 1H), 7.04 (d, J=2.3 Hz, 1H), 6.86 (dd, J=10.2, 3.7 Hz, 2H), 5.04 (d, J=7.6 Hz, 2H), 2.22 (s, 3H).LCMS: (ESI-MS): [M+H]$^+$=238.2.

Step 2 Synthesis of Compound 73

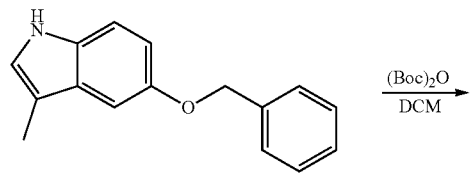

72

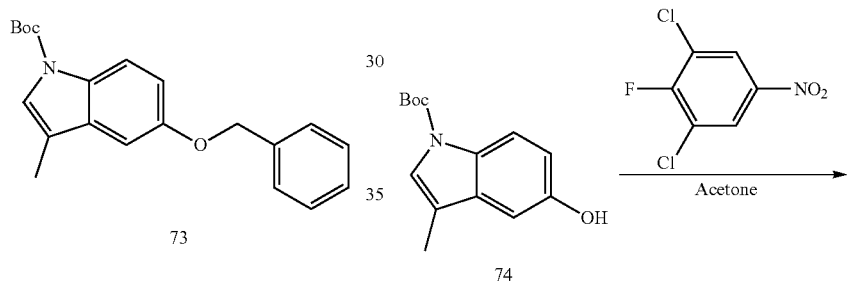

73

To a solution of 72 (5.2 g, 21.9 mmol, 1 eq), DMAP (267 mg, 2.19 mmol, 0.1 eq) and TEA (4.43 g, 43.88 mmol, 2 eq) in dichloromethane (50 ml) was added (Boc)$_2$O (5.73 g, 26.28 mmol, 1.2 eq) at room temperature. The mixture was stirred at room temperature for 2 h. The reaction solution was poured into water and partitioned between DCM (100 ml) and water (50 ml). The organic layer was washed with brine (50 ml), dried (MgSO$_4$) and evaporated. The residue was purified by silica gel flash chromatography (PE:EA=5:1) to afford 73 (5.6 g, 75.7%) as a yellow solid. $^1$H NMR (400 MHz, CDCl$_3$) δ ppm 7.92 (s, 1H), 7.39 (d, J=7.3 Hz, 2H), 7.31 (t, J=7.4 Hz, 2H), 7.24 (t, J=6.5 Hz, 2H), 6.98-6.81 (m, 2H), 5.04 (d, J=5.9 Hz, 2H), 2.14 (s, 3H), 1.57 (s, 9H). LCMS:(ESI-MS): [M+H]$^+$=338.1.

Step 3 Synthesis of Compound 74

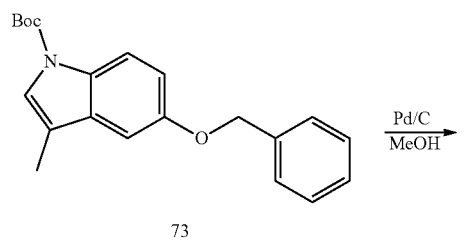

73

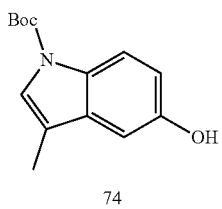

74

To a solution of 73 (5 g, 14.8 mmol, 1.0 eq) in MeOH (50 mL), Pd/C (0.5 g) was added and the mixture was stirred at room temperature overnight under hydrogen. After HPLC showed no start material existed, the solid was removed by filtration and the filterate was concentrated and the residue was purified by silica gel flash chromatography (PE:EA=1:1) to afford the desired product 74 (2 g, 54.5%) as graysolid. $^1$H NMR (400 MHz, CDCl$_3$) δ ppm 7.88 (s, 1H), 7.25 (s, 1H), 6.83 (d, J=2.4 Hz, 1H), 6.75 (dd, J=8.8, 2.5 Hz, 1H), 2.12 (d, J=1.2 Hz, 3H), 1.57 (s, 9H).LCMS: (ESI-MS): [M+H]$^+$=248.1.

Step 4 Synthesis of Compound 75

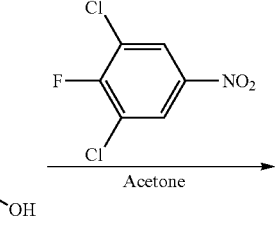

74

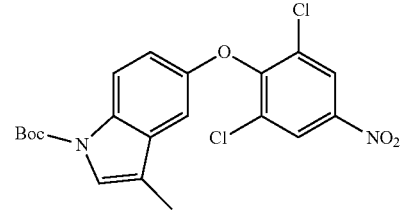

75

To a mixture of 74 (1.0 g, 4 mmol, 1.0 eq) and 1,3-dichloro-2-fluoro-5-nitrobenzene (850 mg, 4.04 mmol, 1.0 eq) in acetone (20 mL), K$_2$CO$_3$ (1.12 g, 8.1 mmol, 2.0 eq) was added. The mixture was stirred at 50° C. for 4 h under nitrogen. When HPLC showed no start material, water (50 mL) was added and the mixture was extracted with EtOAc (3×50 mL). The organic layers were combined and concentrated. The residue was purified by silica gel flash chromatography (PE:EA=10:1) to give the desired prodct 75 (1.4 g, yield: 79.1%) as a yellow solid. $^1$H NMR (400 MHZ, CDCl$_3$) δ ppm 8.25 (s, 2H), 8.05-7.89 (m, 1H), 7.30 (s, 1H), 6.77 (dt, J=8.8, 2.2 Hz, 2H), 2.11 (d, J=1.1 Hz, 3H), 1.58 (d, J=6.7 Hz, 9H).

Step 5 Synthesis of Compound 76

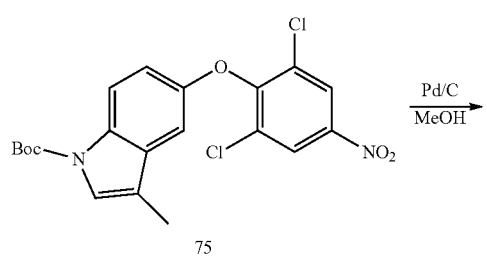

To a solution of 75 (700 mg, 1.6 mmol, 1 eq.) inEtOAc (10 mL), PtO₂ (70 mg) was added and the mixture was stirred at room temperature under hydrogen. After HPLC shows the starting material was disappeared, the solid was removed by filtration and the filtrate was concentrated to give the desired product 76 (550 mg, white solid, yield: 84%). $^1$H NMR (400 MHZ, CDCl₃) δ ppm 7.93 (d, J=13.8 Hz, 1H), 7.26 (s, 1H), 6.86-6.73 (m, 2H), 6.70 (s, 2H), 2.12 (t, J=4.5 Hz, 3H), 1.57 (d, J=7.1 Hz, 9H).LCMS: (ESI-MS): [M+H]⁺=407.0.

Step 6 Synthesis of Compound 77

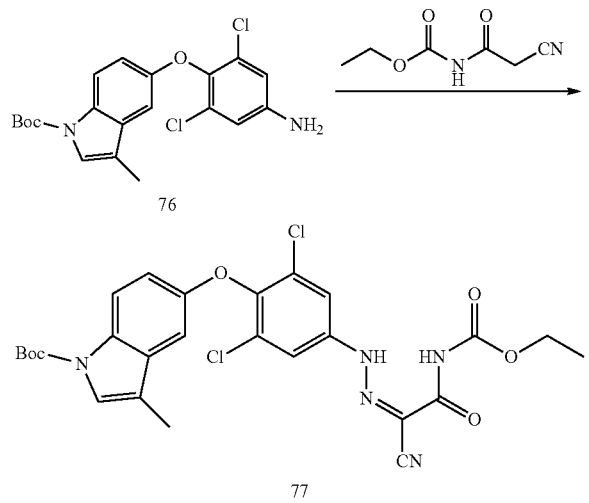

To a solution of 76 (670 mg, 1.64 mmol, 1.0 eq) in 4 N HCl (10 mL) was added a solution of NaNO₂ (159 mg, 2.3 mmol, 1.4 eq) in 1.0 mL of water dropwise at 0° C. The mixture was stirred for 30 min and a mixture of ethyl (ethyl (2-cyanoacetyl) carbamate (289.3 mg, 1.85 mmol, 1.125 eq) in pyridine (2 mL) was added. After stirred for overnight, water (10 mL) and EtOAc (20 mL) was added. The organic layer was dried and concentrated to give the desired product 77 (550 mg, crude), which was used directly for next step without further purification. $^1$H NMR (400 MHZ, CDCl₃) δ ppm 7.93 (d, J=13.8 Hz, 1H), 7.26 (s, 1H), 6.86-6.73 (m, 2H), 6.70 (s, 2H), 2.12 (t, J=4.5 Hz, 3H), 1.57 (d, J=7.1 Hz, 9H).LCMS: (ESI-MS): [M+H]⁺=571.7.

Step 7 Synthesis of Compound I12

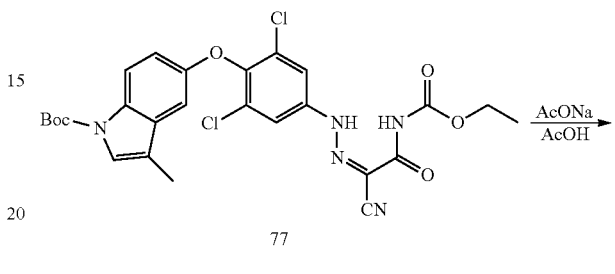

To a solution of 77 (550 mg, 0.96 mmol, 1.0 eq) in AcOH (10 mL) was added NaOAc (394 mg, 4.8 mmol, 5.0 eq) and the mixture was heated to 120° C. After 1.5 h, the mixture was cooled to 0° C. and diluted with water (10 mL), the precipitate was collected by filtration to give the crude product (780 mg), which was purified by Prep-HPLC (30% ACN in water-0.1% TFA as additive) to give desired product 112 (35 mg, red solid, yield: 5%). $^1$H NMR (400 MHZ, MeOD) δ ppm 7.78 (s, 2H), 7.28 (d, J=9.6 Hz, 1H), 7.02 (s, 1H), 6.83-6.73 (m, 2H), 2.21 (s, 3H).LCMS: (ESI-MS): [M+H]⁺=427.7.

Example 13

2-(4-((1H-benzo[d]imidazol-5-yl)oxy)-3,5-dichlorophenyl)-3,5-dioxo-2,3,4,5-tetrahydro-1,2, 4-triazine-6-carbonitrile (I13)

Compound I13 was synthesized through a method similar to that of compound 112.

Example 14

2-(3,5-dichloro-4-((3-methyl-2-oxo-2,3-dihydro-1H-benzo[d]imidazol-5-yl)oxy)phenyl)-3,5-dioxo-2,3,4, 5-tetrahydro-1,2,4-triazine-6-carbonitrile (I14)

Compound I14 was synthesized through a method similar to that of compound I12.

Example 15

2-(3,5-dichloro-4-((2-oxo-2,3-dihydro-1H-benzo[d]imidazol-5-yl)oxy)phenyl)-3,5-dioxo-2,3,4,5-tetrahydro-1,2,4-triazine-6-carbonitrile (I15)

Step 1: Synthesis of I15-2

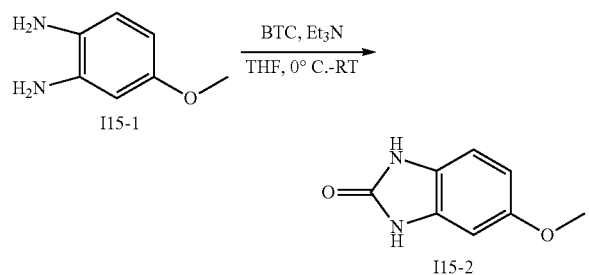

To a solution of compound (3 g, 21.74 mmol) and Et$_3$N (3.3 g, 32.67 mmol) in DCM (30 mL) was added BTC (6.5 g, 21.90 mmol) at 0° C. The resulting mixture was stirred at rt for 6 hours, then diluted with water, adjusted pH to 8 with Na$_2$CO$_3$, extracted with EA (30 mL×2), concentrated. The residue was purified by flash chromatography on silica gel (DCM/MeOH=10/1) to afford compound I15-2 (2 g, 56% yield) as a yellow solid. MS Calcd.: 164; MS Found: 165 [M+H]$^+$.

Step 2: Synthesis of I15-3

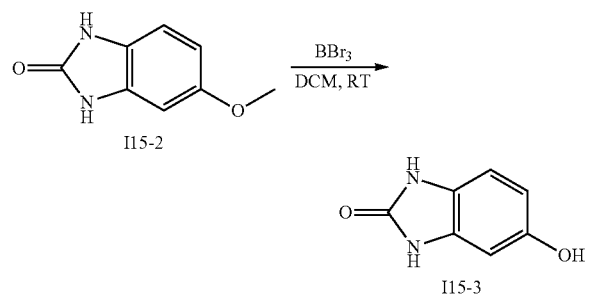

To a solution of compound I15-2 (2 g, 12.20 mmol) in DCM (40 mL) was added BBr$_3$ (15 g, 59.88 mmol) dropwise at 0° C. The reaction mixture was stirred at 40° C. for 8 hours, adjusted pH to 8 with Na$_2$CO$_3$ and concentrated. The product was dissolved out by THF, filtered and concentrated to afford compound I15-3 (1.7 g, 94% yield) as a brown solid. MS Calcd.: 150; MS Found: 151 [M+H]$^+$.

Step 3: Synthesis of I15-4

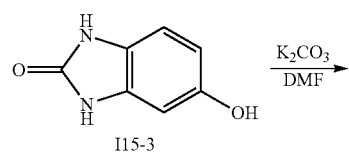

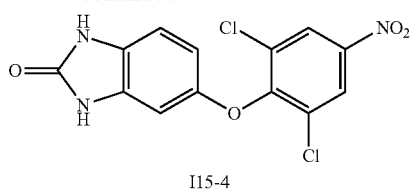

To a solution of compound I15-3 (1.8 g, 12 mmol) in DMF (20 mL) was added 1,3-dichloro-2-fluoro-5-nitrobenzene (2.5 g, 11.90 mmol) and K$_2$CO$_3$ (2.5 mg, 18.12 mmol). The resulting mixture was stirred at 50° C. for 1 hour. The reaction was diluted with H$_2$O (20 mL) and extracted with EA (30 mL×2). The combined organic layers were washed with brine (50 mL), dried over Na$_2$SO$_4$, filtered and concentrated. The residue was purified by flash chromatography on silica gel (DCM/MeOH=10/1) to afford compound I15-4 (2.1 g, 52% yield) as a yellow solid. MS Calcd.: 339; MS Found: 340 [M+H]$^+$.

Step 4: Synthesis of I15-5

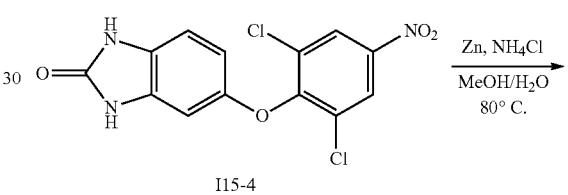

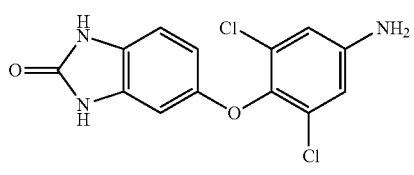

To a solution of compound I15-4 (1.8 g, 5.3 mmol) in MeOH (40 mL) and water (5 mL) was added Zn (3.5 g, 53.85 mmol) and NH$_4$Cl (2.8 g, 52.83 mmol). The reaction mixture was stirred at 80° C. for 3 hours, then filtered and concentrated. The residue was purified by flash chromatography on silica gel (DCM/MeOH=15/1) to afford compound I15-5 (1.5 g, 91% yield) as a yellow solid. MS Calcd.: 309; MS Found: 310 [M+H]$^+$.

Step 5: Synthesis of I15-6

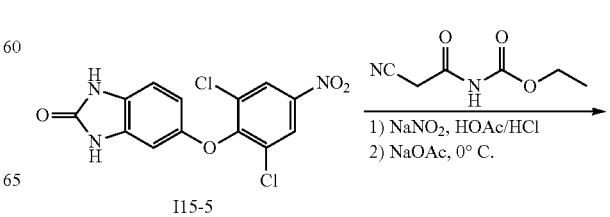

-continued

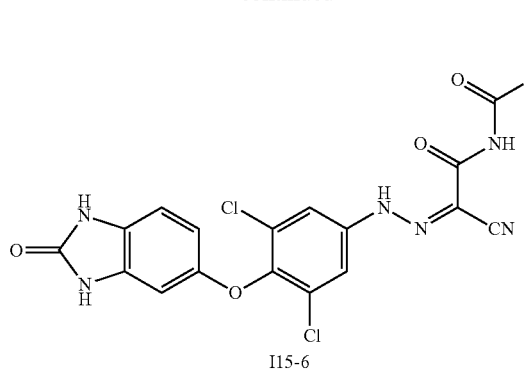

I15-6

To a solution of compound I15-5 (500 mg, 1.62 mmol) in HOAc/HCl=18 mL/3 mL was added NaNO₂ (167 mg, 2.42 mmol) at 5-10° C. The reaction mixture was stirred at 5-10° C. for 30 minutes. Then ethyl (2-cyanoacetyl) carbamate (379 mg, 2.42 mmol) was added followed by a solution of NaOAc (398 mg, 4.85 mmol) in H₂O. The reaction mixture was stirred at 5-10° C. for 3 hours. The reaction was diluted with H₂O (20 mL), stand for 2 days, precipitated solids, filtered, concentrated to afford compound 115-6 (380 mg, 49% yield) as a yellow solid. MS Calcd.: 476; MS Found: 477 [M+H]⁺.

Step 6: Synthesis of I15

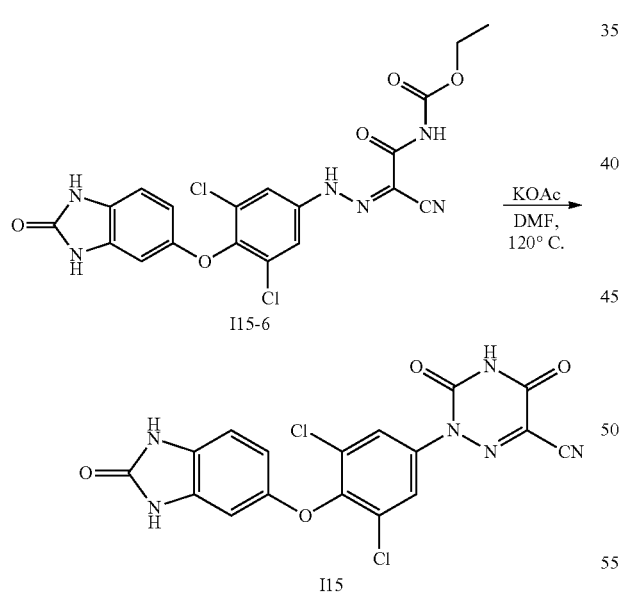

To a solution of compound I15-6 (300 mg, 0.63 mmol) in DMF (15 mL) was added KOAc (185 mg, 1.89 mmol). The reaction mixture was stirred at 120° C. for 3 hours, then filtered and concentrated. The residue was purified by prep-HPLC to afford I15 (59.9 mg, 22% yield) as a white solid. ¹H NMR (400 MHZ, DMSO-d₆) δ: 13.27 (s, 1H), 10.56 (s, 1H), 10.50 (s, 1H), 7.81 (s, 2H), 6.88 (d, J=8.4 Hz, 1H), 6.47-6.45 (m, 1H), 6.42 (d, J=2.0 Hz, 1H), MS Calcd.: 430; MS Found: 431 [M+H]⁺.

Example 16

2-(4-((1H-indol-5-yl)oxy)-3,5-dichlorophenyl)-3,5-dioxo-2,3,4,5-tetrahydro-1,2,4-triazine-6-carbonitrile (I16)

Compound 116 was synthesized through a method similar to that of compound 112.

Example 17

2-(4-((1H-indol-6-yl)oxy)-3,5-dichlorophenyl)-3,5-dioxo-2,3,4,5-tetrahydro-1,2,4-triazine-6-arbonitrile (I17)

Compound I17 was synthesized through a method similar to that of compound I12.

Example 18

2-(3,5-dichloro-4-((2-oxoindolin-5-yl)oxy)phenyl)-3,5-dioxo-2,3,4,5-tetrahydro-1,2,4-triazi ne-6-carbonitrile (I18)

Compound 118 was synthesized through a method similar to that of compound 112.

Example 19

2-(3,5-dichloro-4-((3,3-dimethyl-2-oxoindolin-5-yl)oxy)phenyl)-3,5-dioxo-2,3,4,5-tetrahydr 0-1,2,4-triazine-6-carbonitrile (I19)

Compound 119 was synthesized through a method similar to that of compound I12.

Example 20

2-(3,5-dichloro-4-((2-oxo-2,3-dihydrobenzo[d]oxazol-6-yl)oxy)phenyl)-3,5-dioxo-2,3,4,5-tetrahydro-1,2,4-triazine-6-carbonitrile (I20)

Step 1: Synthesis of I20-2

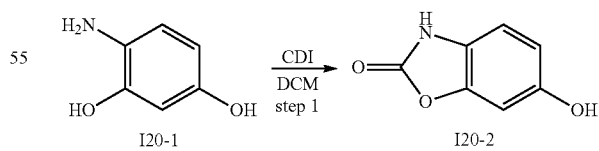

To a solution of compound I20-1 (0.50 g, 3.10 mmol) in THF (10 mL) was added CDI (0.993 g, 6.2 mmol) and Et₃N (0.626 g, 6.2 mmol). The resulting mixture was stirred at r.t for 5 hours. The reaction was concentrated and purified by flash chromatography on silica gel (PE/EA=1/2) to afford compound I20-2 (350 mg, 76% yield) as a white solid. LC-MS (ESI-MS): [M–H]+=149.9.

Step 2: Synthesis of I20-3

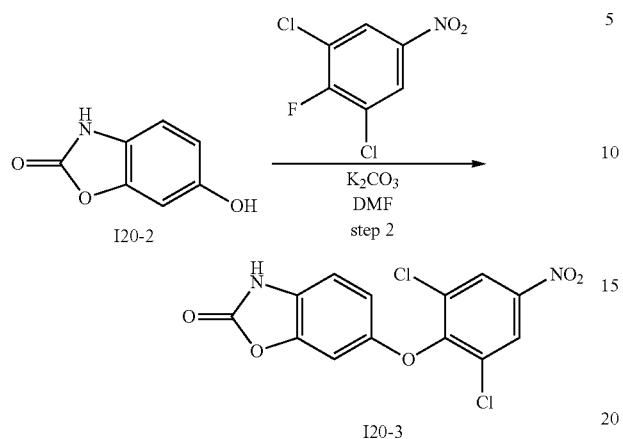

To a solution of compound 120-2 (0.50 g, 3.31 mmol) in DMF (10 mL) was added 1,3-dichloro-2-fluoro-5-nitrobenzene (0.695 g, 3.31 mmol) and $K_2CO_3$ (0.913 g, 6.62 mmol). The reaction mixture was stirred at r.t. overnight. The reaction was diluted with $H_2O$ (200 mL) and extracted with EA (200 mL×3). The combined organic layers were washed with brine (50 mL), dried over $Na_2SO_4$, filtered and concentrated. The residue was purified by flash chromatography on silica gel (PE/EA=1/1) to afford compound I20-3 (700 mg, 62% yield) as a white solid. LC-MS (ESI-MS): $[M-H]^+=339.0$.

Step3: Synthesis of I20-4

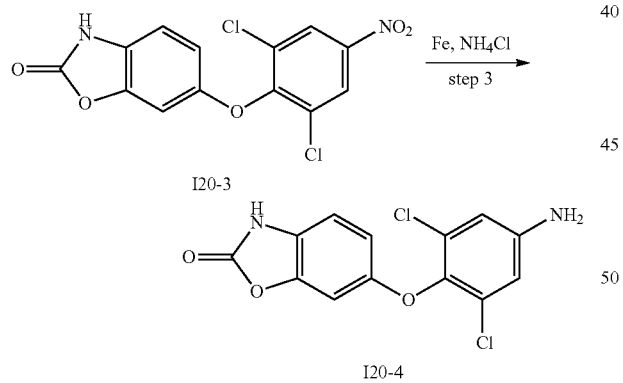

To a solution of compound 120-3 (100 mg, 0.29 mmol) in EtOH (2 mL) and water (1 mL) was added Fe (164 mg, 2.9 mmol) and $NH_4Cl$ (160 mg, 2.9 mmol). The reaction mixture was stirred at reflux for 1.5 hours. The reaction was cooled to r.t, diluted with $H_2O$ (100 mL) and extracted with EA (100 mL×2). The combined organic layers were washed with brine (50 mL×2), dried over $Na_2SO_4$, filtered and concentrated. The residue was purified by flash chromatography on silica gel (PE/EA=1/1) to afford compound I20-4 (70 mg, 78% yield) as a white solid. LC-MS (ESI-MS): $[M-H]^+=309$.

Step 4: Synthesis of I20

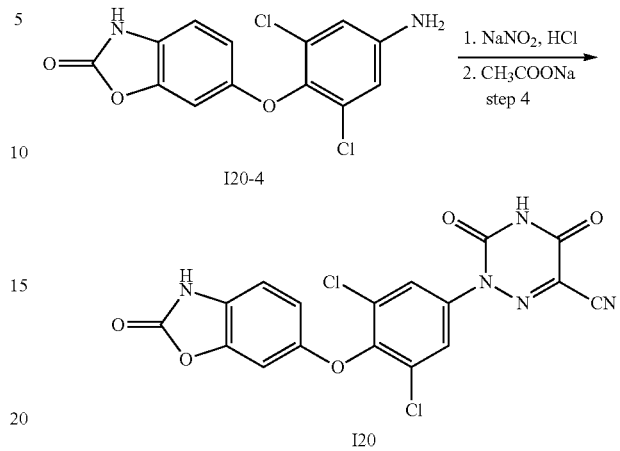

To a solution of compound I20-4 (40 mg, 0.129 mmol) in water (5 mL) was added HCl (0.3 mL, 5%) and $NaNO_2$ (27 mg, 0.387 mmol) at 0° C. The reaction mixture was stirred at rt for 1 hour, ethyl (2-cyanoacetyl) carbamate (50 mg) was added and the resulting mixture was stirred at rt for 2 hours. The reaction was diluted with $H_2O$ (100 mL) and extracted with EA (130 mL×2). The combined organic layers were washed with brine (100 mL×2), dried over $Na_2SO_4$, filtered and concentrated. The residue was dissolved in $CH_3COOH$ (2 mL), $CH_3COONa$ (100 mg) was added. The resulting mixture was stirred at reflux for 2 hours. The reaction was cooled to r.t, diluted with $H_2O$ (50 mL) and extracted with EA (150 mL×3). The combined organic layers were washed with brine (50 mL×2), dried over $Na_2SO_4$, filtered and concentrated. The residue was purified by pre-HPLC to afford compound I20 (7.0 mg, 12.7% yield) as a white solid. LC-MS (ESI-MS): [M–H]+=429.9.1H NMR (400 MHZ, MeOH-$d_4$) δ ppm: 7.87 (s, 1H), 7.12 (d, J=8.4 Hz, 1H), 6.96 (d, J=2.0 Hz, 2H), 6.77-6.74 (m, 1H).

Example 21

2-(3,5-dichloro-4-((3-methyl-1H-indol-5-yl)methyl) phenyl)-3,5-dioxo-2,3,4,5-tetrahydro-1, 2,4-triazine-6-carbonitrile (I21)

Step 1: Synthesis of I21-2

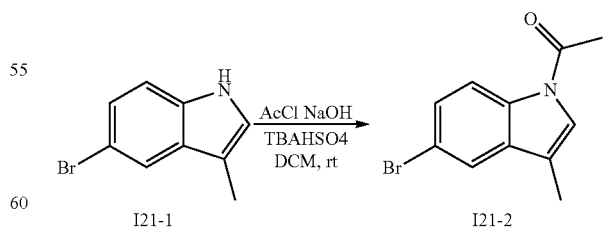

To a solution of I21-1 (1.00 g, 4.79 mmol) in dry dichloromethane (20 mL) were successively added tetrabutylammonium hydrogen sulfate (163.8 g, 0.479 mmol) and freshly finely powdered sodium hydroxide (0.96 g, 23.95 mmol). The resulting solution was stirred for 15 minutes and acetyl chloride (1.6 ml, 23.95 mmol) was added dropwise over 15 minutes. The resulting slurry was vigorously stirred for 2 hours and quenched by addition of water. The organic layer was separated and the aqueous layer was extracted with dichloromethane. Combined organic layers were washed with brine, dried over MgSO$_4$, filtered and concentrated. Flash column chromatography purification (PE/EA: 95/5) led to 1-acetyl-3-methylindole as a white solid (0.81 g, 67.5%).

Step 2: Synthesis of I21-3

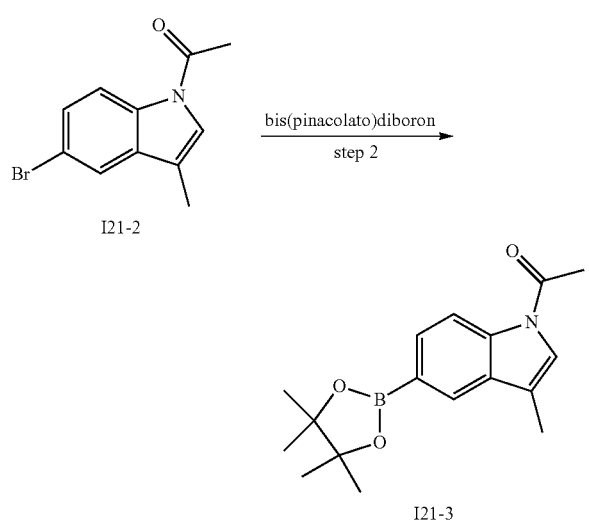

To a solution of compound I21-2 (0.50 g, 1.99 mmol) in 1,4-dioxane (10 mL) was added bis(pinacolato)diboron (758 mg, 2.98 mmol), CH$_3$COOK (0.390 g, 3.98 mmol), Pd(PPh$_3$)$_4$ (150 mg). The reaction mixture was heated to 100° C. under N$_2$ for 10 hours. The reaction was cooled to r.t, diluted with H$_2$O (100 mL) and extracted with EA (200 mL×2). The combined organic layers were washed with brine (50 mL), dried over Na$_2$SO$_4$, filtered and concentrated. The residue was purified by flash chromatography on silica gel (PE/EA=100/1) to afford compound I21-3 (400 mg, 67% yield) as a white solid.

Step 3: Synthesis of I21-4

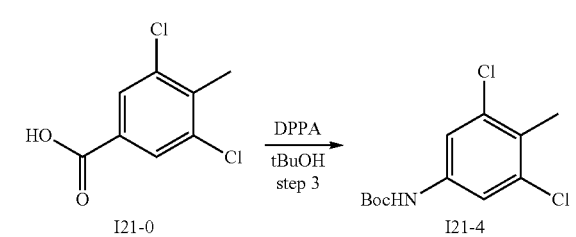 [SMILES: Cc1c(Cl)cc(C(=O)O)cc1Cl ; Cc1c(Cl)cc(NC(=O)OC(C)(C)C)cc1Cl]

To a solution of compound I21-0 (500 mg, 2.43 mmol) in t-BuOH (1 mL) and 1,4-dioxane (5 mL) was added DPPA (1.98 g, 7.3 mmol). The reaction mixture was stirred at reflux for 12 hours. Then the reaction was cooled to r.t, diluted with H$_2$O (50 mL), and extracted with EA (100 mL×2). The combined organic layers were washed with brine (50 mL), dried over Na$_2$SO$_4$, filtered and concentrated. The residue was purified by flash chromatography on silica gel (PE/EA=1/1) to afford compound I21-4 (410 mg, 61% yield) as a dark oil. LC-MS (ESI-MS): [M–55]+=219.7.

Step 4: Synthesis of I21-5

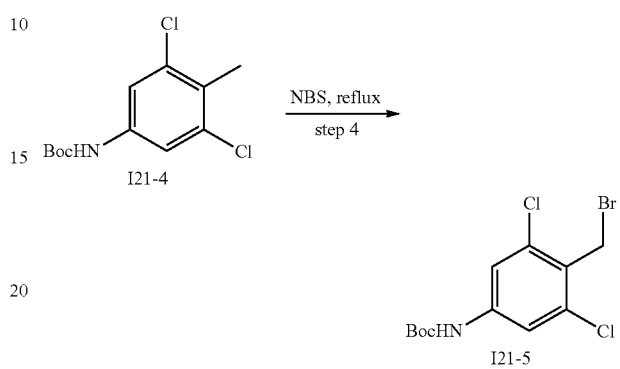

To a solution of compound I21-4 (500 mg, 1.818 mmol) in CCl$_4$ (6 mL) was added NBS (490 mg, 2.72 mmol) and BPO (100 mg). The reaction mixture was stirred at reflux for 3 hours. The reaction was diluted with H$_2$O (100 mL) and extracted with EA (200 mL×2). The combined organic layers were washed with brine (50 mL×2), dried over Na$_2$SO$_4$, filtered and concentrated. The residue was purified by flash chromatography on silica gel (PE/EA=10/1) to afford compound I21-5 (300 mg, 47% yield) as a white solid.

Step 5: Synthesis of I21-6

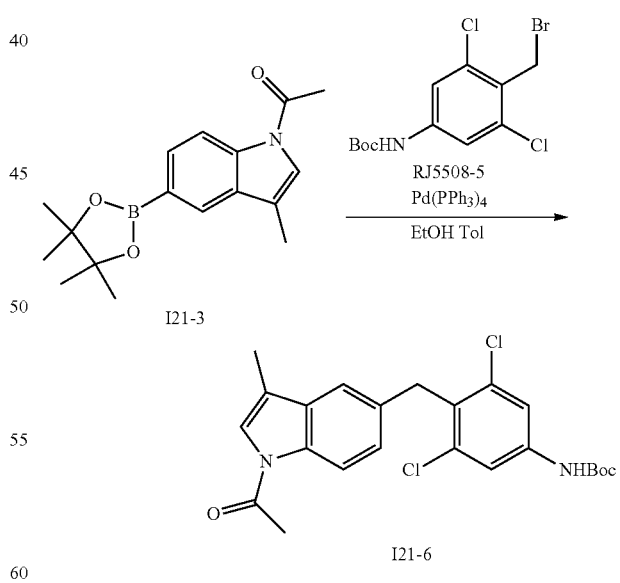

To a solution of compound I21-3 (0.70 g, 2.34 mmol) in Tol (20 mL) and EtOH (4 mL) was added I21-5 (828 mg, 2.34 mmol), Na$_2$CO$_3$ (0.496 g, 4.68 mmol), Pd(PPh$_3$)$_4$ (100 mg). The reaction mixture was heated to 100° C. under N$_2$ for 5 hours. The reaction was cooled to r.t, diluted with H$_2$O (100 mL) and extracted with EA (200 mL×2). The combined organic layers were washed with brine (50 mL), dried over Na$_2$SO$_4$, filtered and concentrated. The residue was purified by flash chromatography on silica gel (PE/EA=5/1) to afford compound I21-6 (400 mg, 38% yield) as a white solid. LC-MS (ESI-MS): [M−55]+=390.7.

Step 6: Synthesis of I21-7

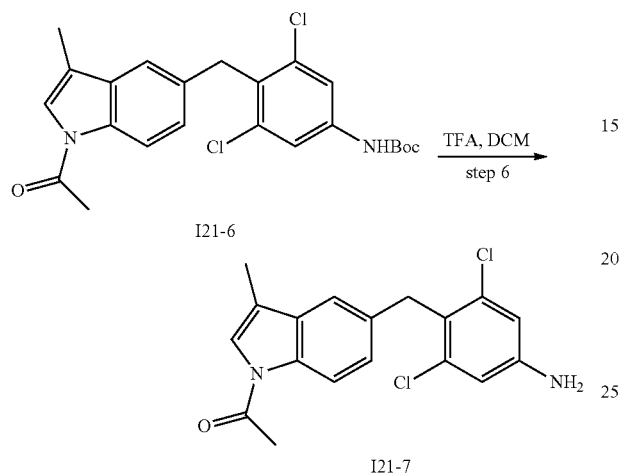

To a solution of compound I21-6 (100 mg, 0.224 mmol) in DCM (2 mL) was added TFA (2 mL). The reaction mixture was stirred r.t for 2 hours. The reaction mixture was concentrated to afford compound I21-7 (70 mg, 90% yield) as a dark solid.

Step 7: Synthesis of I21-8

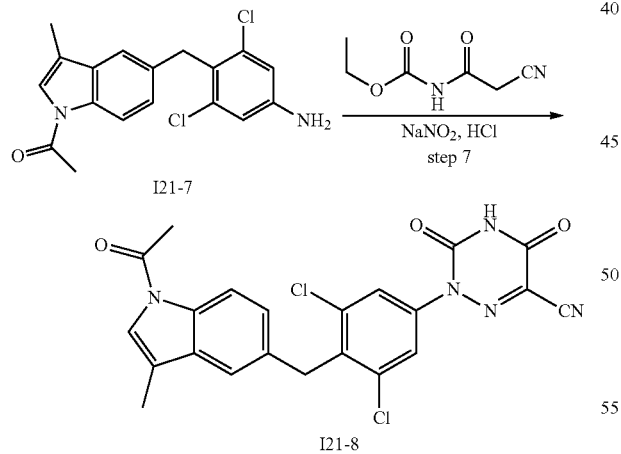

To a solution of compound I21-7 (200 mg, 0.578 mmol) in water (3 mL) was added HCl (0.5 mL, 5%) and NaNO$_2$ (80 mg, 1.156 mmol) at 0° C. The reaction mixture was stirred at r.t for 1 hour, ethyl (2-cyanoacetyl) carbamate (270 mg, 1.73 mmol) was added and the resulting mixture was stirred at r.t for 2 hours. The reaction was diluted with H$_2$O (50 mL) and extracted with EA (50 mL×2). The combined organic layers were washed with brine (10 mL×2), dried over Na$_2$SO$_4$, filtered and concentrated. The residue was dissolved in CH$_3$COOH (2 mL), CH$_3$COONa (30 mg) was added, the resulting mixture was stirred at reflux for 3 hours. The reaction was cooled to r.t., diluted with H$_2$O (50 mL) and extracted with EA (100 mL×3). The combined organic layers were washed with brine (20 mL×2), dried over Na$_2$SO$_4$, filtered and concentrated. The residue was purified by flash chromatography on silica gel (PE/EA=1/1) to afford compound I21-8 (160 mg, 59% yield) as a white solid. MS Calcd.: 467; MS Found: 468 [M+H].+

Step 8: Synthesis of I21

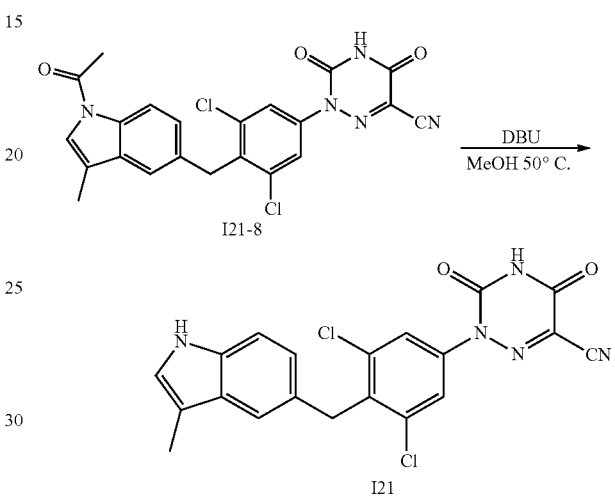

To a solution of compound I21-8 (80 mg, 0.17 mmol) in MeOH (2 mL) was added DBU (51.7 mg, 0.34 mmol). The reaction mixture was stirred at r.t for 1 hour, diluted with H$_2$O (50 mL) and extracted with EA (100 mL×3). The combined organic layers were washed with brine (50 mL×2), dried over Na$_2$SO$_4$, filtered and concentrated. The residue was purified by pre-HPLC to afford compound I21 (31 mg, 64% yield) as a yellow solid. LC-MS (ESI-MS): [M+H]+=426.0. 1H NMR (400 MHZ, DMSO-d6) δ ppm: 13.2 (br, 1H), 10.67 (s, 1H), 7.67 (s, 2H), 7.24 (d, J=8.8 Hz, 2H), 7.07 (s, 1H), 6.89-6.86 (m, 1H), 4.38 (s, 2H), 2.18 (s, 3H).

Example 22

(5-(2,6-dichloro-4-(6-cyano-3,5-dioxo-4,5-dihydro-1,2,4-triazin-2 (3H)-yl)phenoxy)-3-isopropyl-2-oxopyridin-1 (2H)-yl)methyl valinate (I22)

Compound I22 was synthesized through a method similar to that of compound 112.

Example 23 sodium (5-(2,6-dichloro-4-(6-cyano-3,5-dioxo-4,5-dihydro-1,2,4-triazin-2 (3H)-yl) phenoxy)-3-isopropyl-2-oxopyridin-1 (2H)-yl)methyl phosphate (I23)

Compound 123 was synthesized through a method similar to that of compound 112.

Example 24

(5-(2,6-dichloro-4-(6-cyano-3,5-dioxo-4,5-dihydro-1,2,4-triazin-2 (3H)-yl)phenoxy)-3-isopropyl-2-oxopyridin-1 (2H)-yl)methyl acetate (I24)

Compound I24 was synthesized through a method similar to that of compound I12.

Example 25

2-(3,5-dichloro-4-((2-isopropyl-5-oxo-2,5-dihydro-1H-pyrazol-3-yl)oxy)phenyl)-3,5-dioxo-2,3,4,5-tetrahydro-1,2,4-triazine-6-carbonitrile (I25)

Compound I25 was synthesized through a method similar to that of compound I12.

Example 26

2-(3,5-dichloro-4-((2-methyl-5-oxo-2,5-dihydro-1H-pyrazol-3-yl)oxy)phenyl)-3,5-dioxo-2,3,4,5-tetrahydro-1,2,4-triazine-6-carbonitrile (I26)

Compound I26 was synthesized through a method similar to that of compound I12.

Example 27

2-(3,5-dichloro-4-((6-isopropyl-5-oxo-4,5-dihydropyrazin-2-yl)oxy)phenyl)-3,5-dioxo-2,3,4,5-tetrahydro-1,2,4-triazine-6-carbonitrile (I27)

Compound I27 was synthesized through a method similar to that of compound I12.

Example 28

2-(3,5-dichloro-4-((1-isopropyl-2,4-dioxo-1,2,3,4-tetrahydropyrimidin-5-yl)oxy)phenyl)-3,5-dioxo-2,3,4,5-tetrahydro-1,2,4-triazine-6-carbonitrile (I28)

Step 1: Synthesis of I28-2

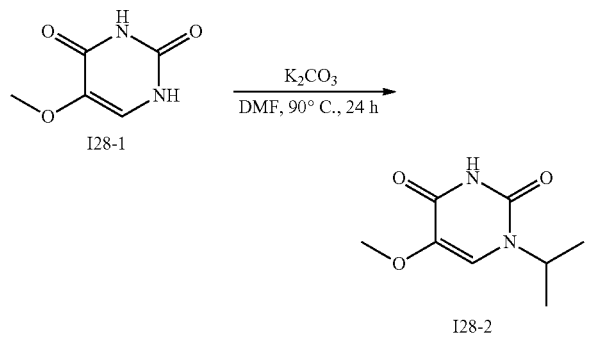

To a solution of compound I28-1 (2 g, 14.08 mmol) in DMF (40 mL) was added 2-iodopropane (4.8 g, 28.23 mmol) and K$_2$CO$_3$ (3.9 g, 28.23 mmol). The resulting mixture was stirred at 90° C. for 24 hours. Then filtered, washed with DMF and concentrated. The residue was purified by flash chromatography on silica gel (DCM/MeOH=100/1) to afford compound I28-2 (300 mg, 12% yield) as a white solid. MS Calcd.: 184; MS Found: 185 [M+H]$^+$.

Step 2: Synthesis of I28-3

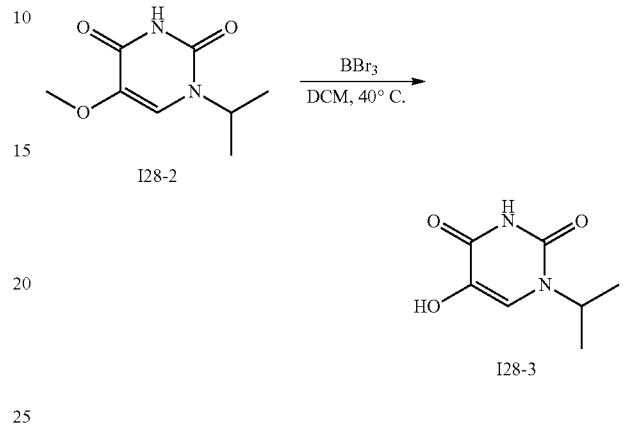

To a solution of compound I28-2 (300 mg, 1.63 mmol) in DCM (8 mL) was added BBr$_3$ (2 g, 7.98 mmol) dropwise at 0° C. and stirred at 40° C. for 10 hour. The reaction mixture was adjusted pH to 8 with Na$_2$CO$_3$ and concentrated. The product was dissolved out by THF, filtered and concentrated to afford compound I28-3 (270 mg, 97% yield) as a white solid. MS Calcd.: 170; MS Found: 171 [M+H]$^+$.

Step 3: Synthesis of I28-4

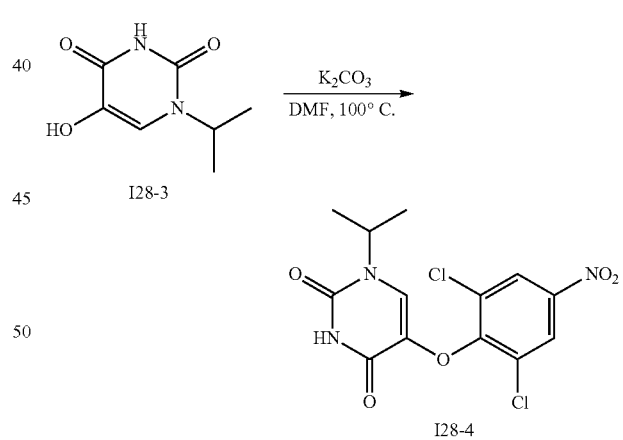

To a solution of compound I28-3 (320 mg, 1.88 mmol) in DMF (40 mL) was added 1,3-dichloro-2-fluoro-5-nitrobenzene (593 mg, 2.82 mmol) and K$_2$CO$_3$ (520 mg, 3.77 mmol). The resulting mixture was stirred at 100° C. for 2 hours. The reaction was diluted with H$_2$O (20 mL) and extracted with EA (30 mL×2). The combined organic layers were washed with brine (50 mL), dried over Na$_2$SO$_4$, filtered and concentrated. The residue was purified by flash chromatography on silica gel (DCM/MeOH=40/1) to afford compound I28-4 (290 mg, 43% yield) as a white solid. MS Calcd.: 359; MS Found: 360 [M+H]$^+$.

Step 4: Synthesis of I28-5

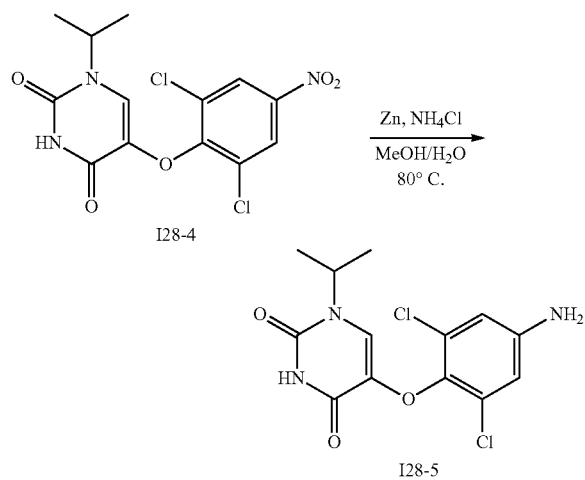

To a solution of compound I28-5 (300 mg, 0.84 mmol) in MeOH (10 mL) and water (1 mL) was added Zn (543 mg, 8.4 mmol) and NH$_4$Cl (443 mg, 8.4 mmol). The reaction mixture was stirred at 80° C. for 3 hours. Then filtered and concentrated. The residue was purified by flash chromatography on silica gel (DCM/MeOH-40/1) to afford compound I28-5 (270 mg, 98% yield) as a white solid. MS Calcd.: 329; MS Found: 330 [M+H]$^+$.

Step 5: Synthesis of I28-6

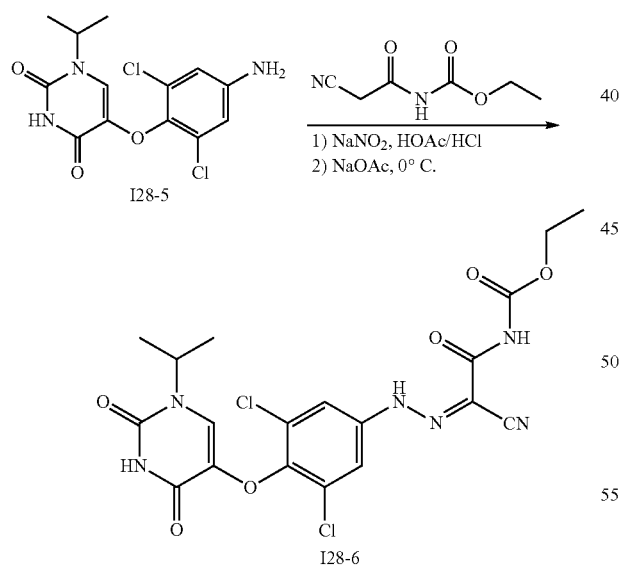

To a solution of compound I28-5 (300 mg, 0.91 mmol) in HOAc/HCl=6 mL/1 mL was added NaNO$_2$ (94 mg, 1.36 mmol) at 5-10° C. The reaction mixture was stirred at 5-10° C. for 30 minutes. Then ethyl (2-cyanoacetyl)carbamate (213 mg, 1.36 mmol) was added, followed by a solution of NaOAc (224 mg, 2.73 mmol) in H$_2$O. The reaction mixture was stirred at 5-10° C. for 8 hours. The reaction was diluted with H$_2$O (20 mL) and extracted with DCM (30 mL×2), concentrated to afford compound I28-6 (300 mg, 66% yield) as a yellow solid. MS Calcd.: 496; MS Found: 497 [M+H]$^+$.

Step 6: Synthesis of I28

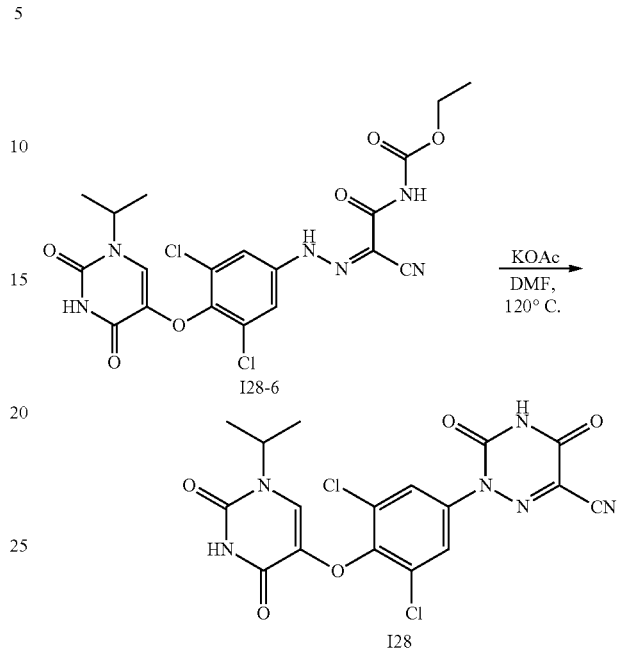

To a solution of compound I28-6 (300 mg, 0.60 mmol) in DMF (15 mL) was added KOAc (178 mg, 1.80 mmol). The reaction mixture was stirred at 120° C. for 3 hours. Then filtered and concentrated. The residue was purified by prep-HPLC to afford I28 (31.2 mg, 11% yield) as a white solid. $^1$H NMR (400 MHZ, DMSO-d$_6$) δ: 13.25 (s, 1H), 11.64 (s, 1H), 7.87 (s, 1H), 7.65 (s, 2H), 4.69-4.62 (m, 1H), 1.25 (d, J=6.8 Hz, 6H). MS Calcd.: 450; MS Found: 451 [M+H]$^+$.

Example 29 and 30

2-(3,5-dichloro-4-((5-isopropyl-6-oxopyrimidin-1(6H)-yl)methyl)phenyl)-3,5-dioxo-2,3,4,5-tetrahydro-1,2,4-triazine-6-carbonitrile (I29)

2-(3,5-dichloro-4-((5-isopropyl-4-oxopyrimidin-1(4H)-yl)methyl)phenyl)-3,5-dioxo-2,3,4,5-tetrahydro-1,2,4-triazine-6-carbonitrile (I30)

Step 1: Synthesis of I30-2

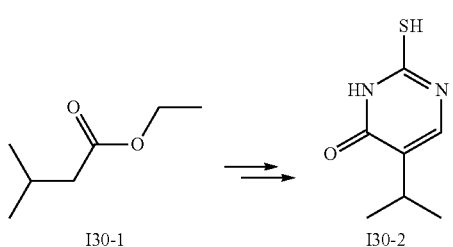

To a solution of I30-1 (10 g, 76.82 mmol) in THF (50 mL) was added LDA (50 mL, 99.87 mmol, 2 M/THF) at −50° C. for 2 min. After 20 min, ethyl formate (8.53 g, 115.2 mmol)

was added at this temperature. The reaction mixture was stirred at room temperature overnight. The reaction mixture was diluted with H₂O (50 mL) and extracted with EA (50 mL×2). The combined organic layers were washed with brine (50 mL×2), dried over Na₂SO₄, filtered and concentrated. The residue was dissolved in 30 mL of MeOH was added thiourea (4.55 g, 59.74 mmol). The reaction mixture was stirred at 70° C. for 4 hours. The reaction was concentrated and purified by flash chromatography on silica gel (PE/EA=5/1) to afford compound 130-2 (6.0 g, 46% yield) as a yellow solid. MS Calcd.: 170; MS Found: 171 [M+H]⁺.

Step 2: Synthesis of I30-3

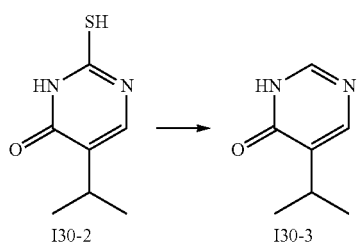

To a solution of compound I30-2 (3.0 g, 17.6 mmol) in MeOH (30 mL) was added Raney Ni (2 mL, 10%) and the reaction mixture was stirred under H₂ of balloon at 70° C. overnight. The reaction mixture was filtered and washed with MeOH (20 mL). The residue was concentrated to give compound I30-3 (1.4 g, 58% yield) as a yellow solid. MS Calcd.: 138; MS Found: 139 [M+H]⁺.

Step 3: Synthesis of I30-4 and I30-4a

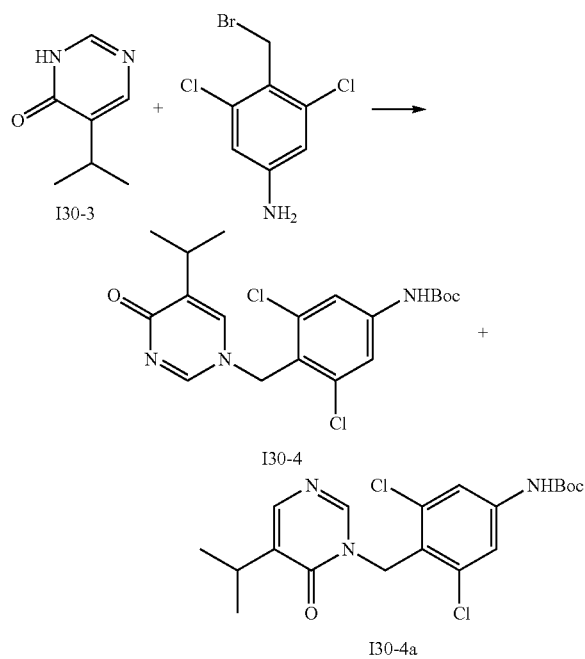

To a solution of compound I30-3 (0.4 g, 2.9 mmol) in DMF (20 mL) was added 4-(bromomethyl)-3,5-dichloroaniline (1.03 g, 2.9 mmol) and K₂CO₃ (1.2 g, 8.7 mmol). The resulting mixture was stirred at 100° C. under N₂ overnight. The reaction mixture was cooled to r.t., diluted with H₂O (20 mL) and extracted with EA (20 mL×3). The combined organic layers were washed with brine (50 mL×2), dried over Na₂SO₄, filtered and concentrated. The residue was purified by flash chromatography on reverse phase silica gel (ACN/H₂O=5%-95%, 254 nm, 30 min) to afford compound I30-4 (450 mg, 38% yield) and compound I30-4a (350 mg, 29% yield) as a yellow solid. MS Calcd.: 412; MS Found: 413 [M+H]⁺. ¹H NMR (I30-4, 400 MHZ, DMSO-d₆) δ: 9.92 (s, 1H), 8.25 (d, J=2.4 Hz, 1H), 7.66 (s, 2H), 7.32 (d, J=2.0 Hz, 1H), 5.25 (s, 2H), 2.78-2.72 (m, 1H), 1.48 (s, 9H), 1.06-1.03 (m, 6H). ¹H NMR (I30-4a, 400 MHz, DMSO-d₆) δ: 9.83 (s, 1H), 8.05 (s, 1H), 7.75 (s, 1H), 7.60 (s, 2H), 5.21 (s, 2H), 2.95-2.84 (m, 1H), 1.48 (s, 9H), 1.12 (d, J=6.8 Hz, 6H).

Step 4: Synthesis of I30-5

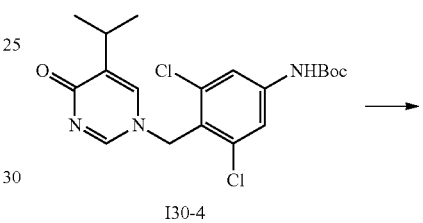

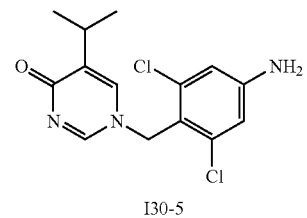

To a solution of compound I30-4 (450 mg, 1.1 mmol) in EA (20 mL) was added HCl/EA (2 mL). The reaction mixture was stirred at room temperature for 2 hours. The reaction mixture was filtered and washed with Et₂O (10 mL). The residue was concentrated to give compound I30-5 (340 mg, 100% yield) as a yellow solid. MS Calcd.: 312; MS Found: 313 [M+H]⁺.

Step 5: Synthesis of I30

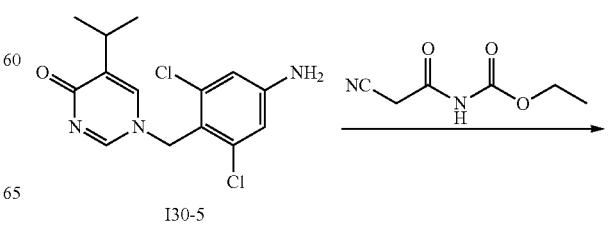

-continued

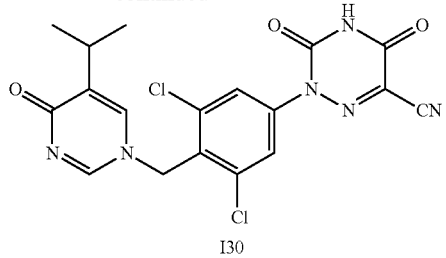

I30

Step 5: Synthesis of I29

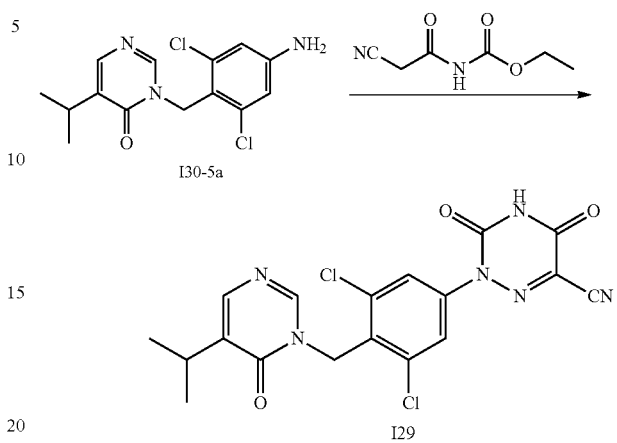

To a solution of compound I30-5 (300 mg, 0.96 mmol) in HOAc/HCl (6 mL/1 mL) was added NaNO$_2$ (99.4 mg, 1.44 mmol) at 5-10° C. The reaction mixture was stirred at 5-10° C. for 30 minutes. Then ethyl (2-cyanoacetyl) carbamate (225 mg, 1.44 mmol) was added followed by a solution of NaOAc (236.2 mg, 2.88 mmol) in H$_2$O (2 mL). The reaction mixture was stirred at room temperature for 2 hours. The reaction was diluted with H$_2$O (20 mL) and extracted with EA (30 mL×2). The combined organic layers were washed with brine (20 mL×2), dried over Na$_2$SO$_4$, filtered and concentrated. The residue was dissolved in 15 mL of DMF, was added KOAc (282.2 mg, 2.88 mmol). The reaction mixture was stirred at 120° C. for 2 hours. The reaction was diluted with H$_2$O (20 mL) and extracted with EA (30 mL×2). The combined organic layers were washed with brine (20 mL×2), dried over Na$_2$SO$_4$, filtered and concentrated. The residue was purified by prep-HPLC to afford I30 (37 mg, 9% yield) as a yellow solid. MS Calcd.: 433; MS Found: 434 [M+H]$^+$. $^1$H NMR (400 MHZ, DMSO-d$_6$) δ: 8.31 (d, J=2.8 Hz, 1H), 7.79 (s, 2H), 7.39-7.37 (m, 1H), 5.37 (s, 2H), 2.79-2.71 (m, 1H), 1.05 (d, J=6.8 Hz, 6H).

Step 6: Synthesis of I30-5a

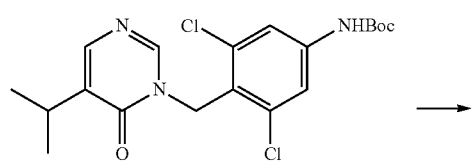

I30-4a

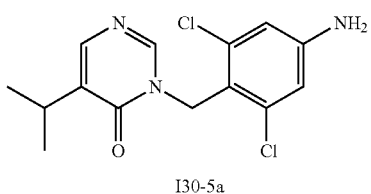

I30-5a

To a solution of compound I30-4a (264 mg, 1.1 mmol) in EA (20 mL) was added HCl/EA (2 mL). The reaction mixture was stirred at room temperature for 2 hours. The reaction mixture was filtered and washed with Et$_2$O (10 mL). The residue was concentrated to give compound I30-5a (200 mg, 100% yield) as a yellow solid. MS Calcd.: 312; MS Found: 313 [M+H]$^+$.

To a solution of compound I30-5a (200 mg, 0.96 mmol) in HOAc/HCl (6 mL/1 mL) was added NaNO$_2$ (66.2 mg, 0.96 mmol) at 5-10° C. The reaction mixture was stirred at 5-10° C. for 30 minutes. Then ethyl (2-cyanoacetyl) carbamate (150 mg, 0.96 mmol) was added followed by a solution of NaOAc (157.44 mg, 1.92 mmol) in H$_2$O (2 mL). The reaction mixture was stirred at room temperature for 2 hours. The reaction was diluted with H$_2$O (20 mL) and extracted with EA (30 mL×2). The combined organic layers were washed with brine (20 mL×2), dried over Na$_2$SO$_4$, filtered and concentrated. The residue was dissolved in 15 mL of DMF, was added KOAc (188.16 mg, 1.92 mmol). The reaction mixture was stirred at 120° C. for 2 hours. The reaction was diluted with H$_2$O (20 mL) and extracted with EA (30 mL×2). The combined organic layers were washed with brine (20 mL×2), dried over Na$_2$SO$_4$, filtered and concentrated. The residue was purified by prep-HPLC to afford I29 (14 mg, 5% yield) as a yellow solid. MS Calcd.: 433; MS Found: 434 [M+H]$^+$. $^1$H NMR (400 MHz, DMSO-d$_6$) δ: 8.26 (s, 1H), 7.77 (s, 1H), 7.69 (s, 2H), 7.08 (brs, 1H), 5.31 (s, 2H), 2.92-2.85 (m, 1H), 1.11 (d, J=6.8 Hz, 6H).

Example 31

2-(3,5-dichloro-4-((5-isopropyl-2,4-dioxo-3,4-dihydropyrimidin-1(2H)-yl)methyl)phenyl)-3, 5-dioxo-2, 3,4,5-tetrahydro-1,2,4-triazine-6-carbonitrile (I31)

Step 1: Synthesis of I31-02

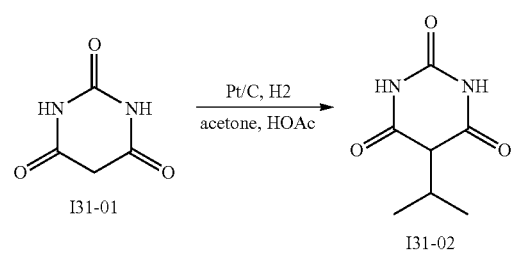

To a solution of compound I31-01 (10.0 g, 78.06 mmol) in HOAc (100 mL) was added acetone (50 mL) and Pt/C (5.0 g). The reaction mixture was stirred at room temperature under $H_2$ for 2 days. The reaction mixture was completed detected by LCMS. The solid was removed by filtration under reduced pressure and the filtrate was concentrated to give compound I31-02 (15.0 g, crude) as a gray solid. The crude was used into the following reaction without the further purification. MS Calcd.: 170.2; MS Found: 171.2 [M+H]+.

Step 2: Synthesis of I31-03

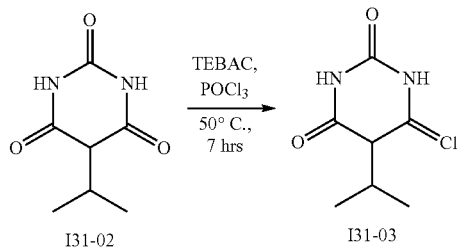

To a solution of compound I31-02 (1.0 g, 5.88 mmol) in $POCl_3$ (13.7 mL, 147.00 mmol) was added N-benzyl-N,N,N-triethylammonium chloride (2.7 g, 11.76 mmol). The reaction mixture was heated to 50° C. and stirred for 7 hours. The reaction was cooled to room temperature and evaporated to dryness in vacuum. The residue was carefully quenched with ice water (30 mL) at 0° C. and the slurry was kept in a refrigerator for 7 hours. The resulting white precipitate was collected and washed thoroughly with hexanes (30 mL×2) to afford compound I31-03 (770.0 mg, crude) as a white solid. The crude was used into the following reaction without the further purification. MS Calcd.: 188.6; MS Found: 189.6 [M+H]+.

Step 3: Synthesis of I31-04

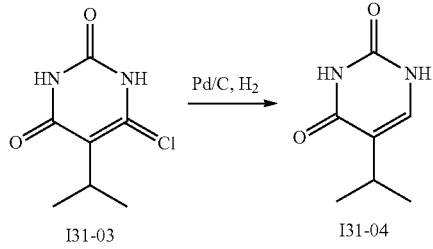

To a solution of compound I31-03 (770.0 mg, 4.09 mmol) in NaOH (100 mL, 2 N aq) was added Pd/C (500 mg). The reaction mixture was shaken in a hydrogen atmosphere for 3 hours with the initial pressure of 40 psi. The catalyst was removed by filtration and the filtrate was acidified with concentrated HCl to pH=2. The resulting precipitate was collected, washed, and dried to give compound I31-04 (418.0 mg, 66.5% yield).MS Calcd.: 154.2; MS Found: 155.2 [M+H]$^+$.

Step 4: Synthesis of I31-06

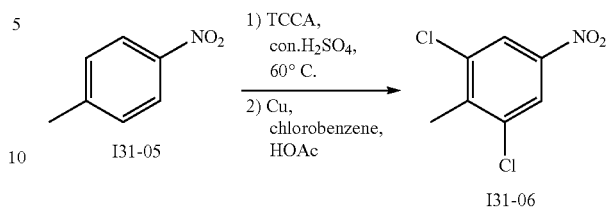

To a solution of compound I31-05 (8.2 g, 59.85 mmol), trichloroisocyanuric acid (15.9 g, 65.84 mmol) and concentrated sulfuric acid (50 mL) was stirred at 60° C. for 20 hours. The solution was cooled to 25° C. and then poured into iced water (100 mL). The resulting mixture was filtered through a pad of Celite (20 g), after which the pad was washed with diethyl ether (50 mL). Organic layer of the filtrate was separated and the aqueous layer was extract with diethyl ether (30 mL×2). The organic layer collected was washed with brine (50 mL×2), dried over $Na_2SO_4$ and concentrated in vacuum to give a crude product as a pale yellow solid. A mixture of the crude product, copper (12.0 g) and chlorobenzene (15 mL) was stirred at 25° C. for 5 minutes, then acetic acid (10 mL) was added to it, and the resulting solution was refluxed for 20 hours. After cooling to 25° C., the mixture was filtered through a pad of Celite, after which the pad was washed with toluene (50 mL). The filtrate was washed with brine (20 mL×3), dried over $Na_2SO_4$ and concentrated in vacuum. The crude residue was purified by chromatography on silica gel (PE) to give compound I31-06 (9.0 g, 73.0% yield) as a yellow solid.

Step 5: Synthesis of I31-07

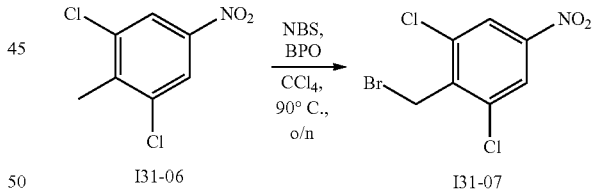

To a solution of compound I31-06 (8.0 g, 38.83 mmol) in $CCl_4$ (50 mL) was added NBS (10.4 g, 58.25 mmol) and BPO (932.0 mg, 0.39 mmol). The reaction mixture was stirred at 90° C. for 16 hours. The reaction mixture was completed detected by TLC (PE). The mixture was poured into 10 mL of water and the product was extracted with EA (100 mL×3). The organic layer was washed with water (100 mL×2) and 50 mL of brine, and then dried over $Na_2SO_4$. After filtration, the solvent was removed under reduced pressure. The residue was purified by chromatography on silica gel (PE) to give compound I31-07 (9.4 g, 84.9% yield) as a yellow solid. $^1$H NMR (400 MHZ, DMSO-$d_6$) δ: 8.37 (s, 2H), 4.83 (s, 2H).

Step 6: Synthesis of I31-08

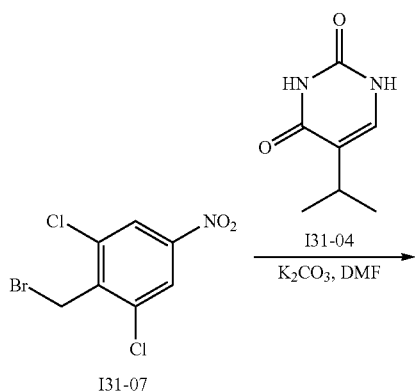

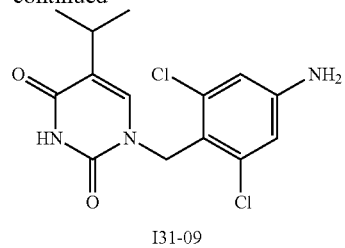

To a solution of compound I31-07 (722.0 mg, 2.53 mmol) in DMF (20 mL) was added compound I31-04 (390.0 mg, 2.53 mmol) and $K_2CO_3$ (1.05 g, 7.60 mmol). The reaction mixture was stirred at room temperature for 16 hours. The reaction mixture was completed detected by LCMS. The mixture was poured into 50 mL of water and the product was extracted with EA (50 mL×3). The organic layer was washed with water (50 mL×2) and 50 mL of brine, and then dried over $Na_2SO_4$. After filtration, the solvent was removed under reduced pressure. The residue was purified by chromatography on silica gel (PE:EA=5:1) to give compound I31-08 (550.0 mg, 60.6% yield) as a yellow solid. $^1$H NMR (400 MHz, DMSO-$d_6$) δ: 11.26 (s, 1H), 8.32 (s, 2H), 7.42 (s, 1H), 5.18 (s, 2H), 2.77-2.68 (m, 1H), 1.08-1.03 (m, 6H). MS Calcd.: 358.2; MS Found: 360.2 [M+H]+.

Step 7: Synthesis of I31-09

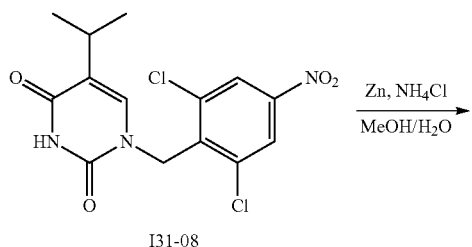

To a solution of compound I31-08 (520.0 mg, 1.46 mmol) in MeOH/$H_2O$ (30/5 mL) was added zinc powder (947.0 mg, 14.57 mmol) and $NH_4Cl$ (386.0 mg, 7.28 mmol). The reaction mixture was stirred at 80° C. for 3 hours. The reaction mixture was completed detected by LCMS. The solid was removed by filtration under reduced pressure and the filtrate was concentrated to give compound I31-09 (430.0 mg, 90.3% yield) as a yellow solid. The crude was used into the following reaction without the further purification. MS Calcd.: 328.2; MS Found: 330.3 [M+H]+

Step 8: Synthesis of I31-11

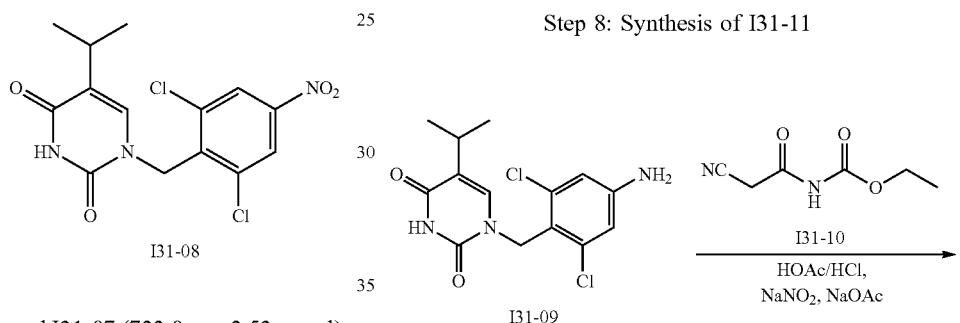

To a solution of compound I31-09 (380.0 mg, 1.16 mmol) in HOAc/HCl (6/1 mL) was added $NaNO_2$ aq (120.0 mg, 1.74 mmol, 1 mL) at 0° C. The reaction mixture was stirred at 5-10° C. for 30 minutes. Then compound I31-10 (272.0 mg, 1.74 mmol) was added a solution of NaOAc (286.0 mg, 3.49 mmol, 1 mL) in $H_2O$ was added subsequently. The reaction mixture was stirred at 5-10° C. for 2 hours. The reaction was diluted with $H_2O$ (20 mL) and extracted with DCM (30 mL×2). The organic layers were combined and concentrated to afford compound I31-11 (320.0 mg, 55.7% yield) as a yellow solid. The crude product was used into the following reaction without further purification. MS Calcd.: 495.3; MS Found: 496.8 [M+H]+.

Step 9: Synthesis of I31

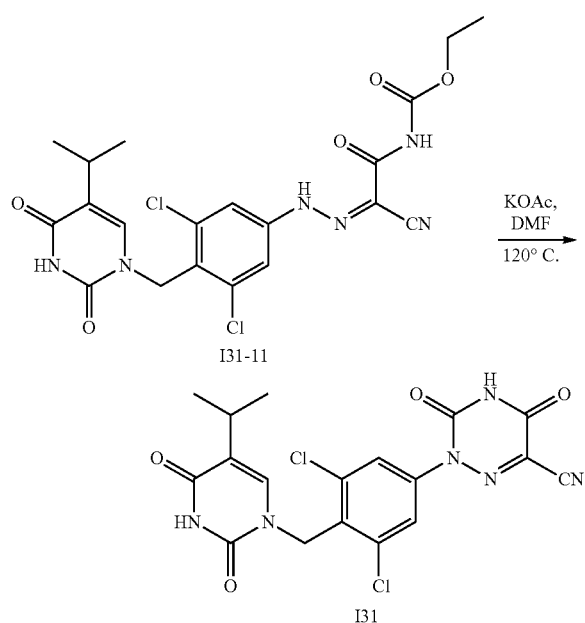

To a solution of compound I31-11 (320.0 mg, 0.65 mmol) in DMF (15 mL) was added KOAc (191.1 mg, 1.95 mmol). The reaction mixture was stirred at 120° C. for 3 hours. The reaction was quenched with water (20 mL). The resulting mixture was extracted with EA (20 mL×3). The organic layer was combined and washed with water (20 mL) and 20 mL of brine, and then dried over $Na_2SO_4$. After filtration, the solvent was removed under reduced pressure. The residue was purified by pre. HPLC to give compound I31 (45.0 mg, 15.4% yield) as a yellow solid. $^1$H NMR (400 MHZ, DMSO-$d_6$) δ: 7.71 (s, 2H), 7.23 (s, 1H), 7.09 (brs, 2H), 5.11 (s, 2H), 2.74-2.67 (m, 1H), 1.04 (d, J=6.8 Hz, 6H). MS Calcd.: 449.3; MS Found: 451.0 [M+H]+.

Example 32

2-(3,5-dichloro-4-((1-isopropyl-2-oxo-1,2-dihydropyrimidin-5-yl)oxy)phenyl)-3,5-dioxo-2,3, 4,5-tetrahydro-1,2,4-triazine-6-carbonitrile (I32)

Step1: Synthesis of I32-2

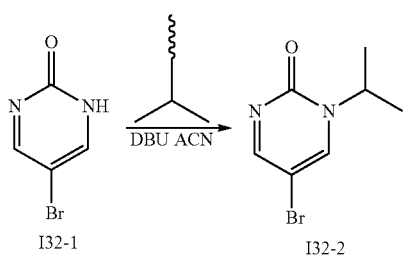

To a solution of compound I32-1 (7 g, 0.04 mol) in ACN (50 mL) was added DBU (7.3 g, 0.048 mol) and 2-iodopropane (8.16 g, 0.048 mol). The mixture was stirred at 70° C. for 8 hours. Then the reaction mixture was diluted with water, extracted with EA (100 mL×5). The combined organic phases were concentrated. The residue was purified by column chromatography on silica gel (PE/EA=1/10) to afford compound I32-2 (4.5 g, 51.8% yield) as a yellow solid. MS Calcd.: 217; MS Found: 218 [M+H]+.

Step 2: Synthesis of I32-3

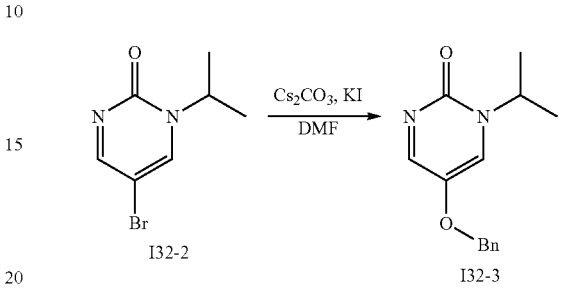

To a solution of compound I32-2 (1.5 g, 6.9 mmol) in DMF (20 mL) was added phenylmethanol (1.5 g, 13.8 mmol), $Cs_2CO_3$ (2.86 g, 20.7 mmol) and KI (0.57 g, 3.5 mmol). The mixture was stirred at 100° C. for 3 hours. The reaction mixture was diluted with water, extracted with EA (50 mL×2). The combined organic phases were washed with brine (50 mL) and concentrated. The residue was purified by column chromatography on silica gel (PE/EA=2/1) to afford compound I32-3 (0.38 g, 22.5% yield) as a yellow solid. MS Calcd.: 244; MS Found: 245 [M+H]+.

Step 3: Synthesis of I32-4

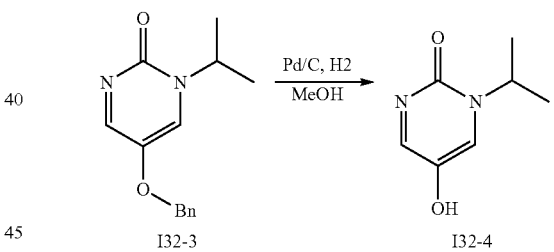

To a solution of compound I32-3 (380 mg, 1.56 mmol) in MeOH (10 mL) was added Pd/C (60% wet, 10 wt %, 50 mg). The mixture was stirred at room temperature under $H_2$ for 2 hours. The reaction was filtered and concentrated to afford compound I32-4 (250 mg, >100% yield) as a yellow oil. MS Calcd.: 154; MS Found: 155 [M+H]+.

Step 4: Synthesis of I32-5

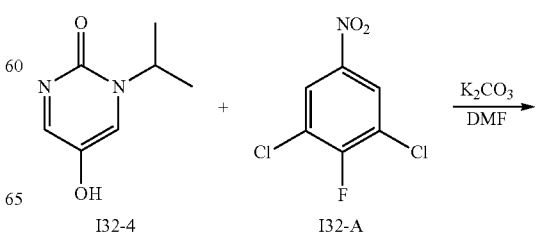

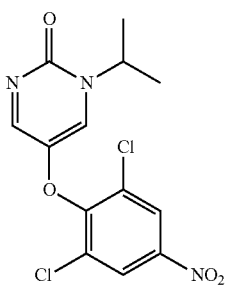

I32-5

To a solution of compound I32-4 (220 mg, 1.43 mmol) in DMF (5 mL) was added compound I32-A (300 mg, 1.43 mmol) and $K_2CO_3$ (591.4 mg, 4.29 mmol). The reaction mixture was stirred at 100° C. for 1 hour. The reaction mixture was diluted with water, extracted with EA (20 mL×2). The combined organic phases were washed with brine (20 mL) and concentrated. The residue was purified by column chromatography on silica gel (PE/EA=2/1) to afford compound I32-5 (250 mg, 51.0% yield) as a yellow solid. MS Calcd.: 344; MS Found: 345 $[M+H]^+$.

Step 5: Synthesis of I32-6

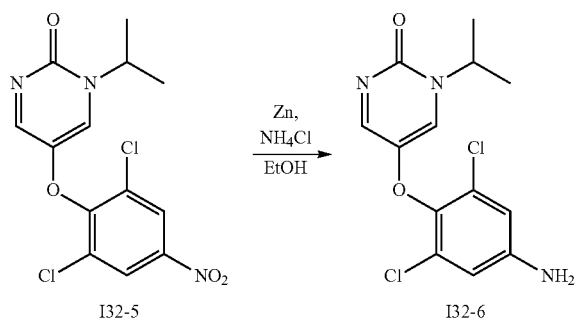

To a solution of compound I32-5 (250 mg, 0.73 mmol) in EtOH (10 mL) and water (1 mL) was added Zn (237 mg, 3.64 mmol) and $NH_4Cl$ (195 mg, 3.64 mmol). The reaction mixture was stirred at 80° C. for 5 hours. Then filtered and concentrated. The residue was purified by column chromatography on silica gel (DCM/MeOH=20/1) to afford compound I32-6 (200 mg, 87.7% yield) as a yellow solid. MS Calcd.: 314; MS Found: 315 $[M+H]^+$.

Step 6: Synthesis of I32

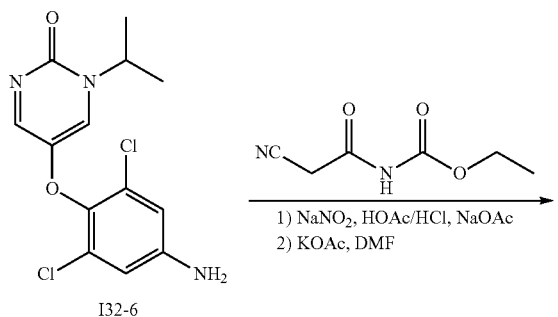

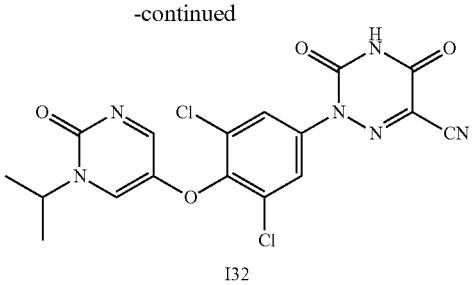

I32

To a solution of compound I32-6 (200 mg, 0.64 mmol) in the solution of HOAc (6 mL) and HCl (1 mL) was added $NaNO_2$ (66.1 mg, 0.96 mmol) at 5~10° C. The reaction mixture was stirred at 5-10° C. for 30 minutes. Then ethyl (2-cyanoacetyl) carbamate (149.5 mg, 0.96 mmol) was added followed by a solution of NaOAc (157.2 mg, 1.92 mmol) in $H_2O$. The reaction mixture was stirred at 5-10° C. for 5 hours. The reaction was diluted with water, extracted with DCM (20 mL). The combined organic phases were concentrated to get the crude product. The crude was dissolved in DMF (5 mL) and KOAc (128.6 mg, 1.31 mmol) was added. The mixture was stirred at 120° C. for 4 hours. Then filtered and concentrated. The residue was purified by prep-HPLC to afford 132 (14.5 mg, 7.6% yield) as a yellow solid. $^1$H NMR (400 MHZ, DMSO-$d_6$) δ: 7.79 (d, J=8 Hz, 1H), 7.77 (s, 2H), 5.83 (d, J=8 Hz, 1H), 4.72-4.68 (m, 1H), 1.31 (d, J=6.8 Hz, 6H), MS Calcd.: 434; MS Found: 435 $[M+H]^+$.

Example 33

2-(3,5-dichloro-4-((3-isopropyl-2,4-dioxo-1,2,3,4-tetrahydropyrimidin-5-yl)oxy)phenyl)-3,5-dioxo-2,3,4,5-tetrahydro-1,2,4-triazine-6-carbonitrile (I33)

Step 1: Synthesis of I33-2

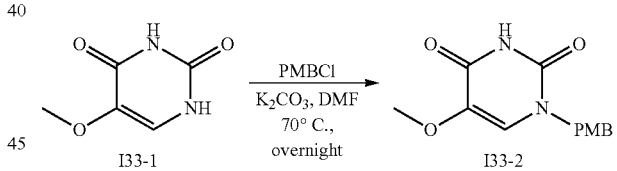

To a solution of compound I33-1 (20 g, 141 mmol) and $K_2CO_3$ (39 g, 283 mmol) in DMF (100 mL) was added PMBCl (26 g, 167 mmol) at 0° C. The resulting mixture was stirred at 70° C. overnight, then filtered, washed with DMF and concentrated. The residue was purified by flash chromatography on silica gel (DCM/MeOH=40/1) to afford compound I33-2 (4.6 g, 12% yield) as a white solid. MS Calcd.: 262; MS Found: 263 $[M+H]^+$.

Step 2: Synthesis of I33-3

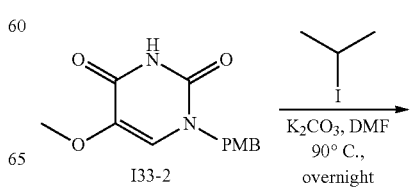

-continued

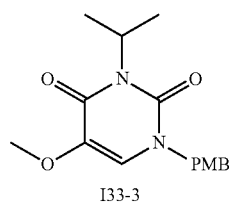

I33-3

To a solution of compound I33-2 (4.6 g, 17.56 mmol) in DMF (50 mL) was added 2-iodopropane (7.5 g, 44.12 mmol) and K₂CO₃ (6 g, 43.48 mmol). The resulting mixture was stirred at 90° C. for overnight, then filtered, washed with DMF and concentrated. The residue was purified by flash chromatography on silica gel (DCM/MeOH=100/1) to afford compound I33-3 (300 mg, 12% yield) as a white solid. MS Calcd.: 304; MS Found: 305 [M+H]⁺.

Step 3: Synthesis of I33-4

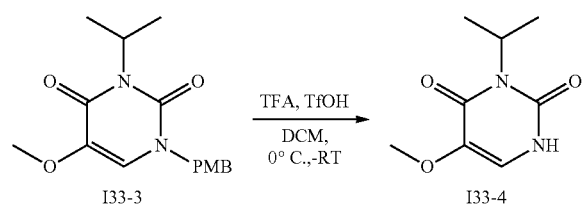

To a solution of compound I33-3 (4.2 g, 13.81 mmol) in DCM (50 mL) was added TFA (20 mL) and TfOH (2 mL) at 0° C. The resulting mixture was stirred at r.t for 4 hours. Then concentrated and adjusted pH to 8 with Na₂CO₃, concentrated. The residue was purified by flash chromatography on silica gel (DCM/MeOH=60/1) to afford compound I33-4 (2 g, 79% yield) as a white solid. MS Calcd.: 184; MS Found: 185 [M+H]⁺.

Step 4: Synthesis of I33-5

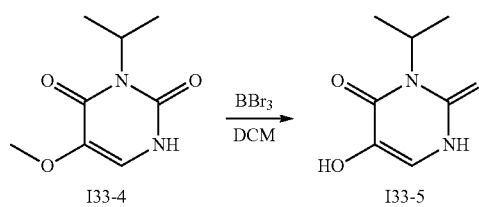

To a solution of compound I33-4 (2.6 g, 14.13 mmol) in DCM (8 mL) was added BBr₃ (17.6 g, 17.70 mmol) dropwise at 0° Cr and stirred at r.t for 6 hour. The reaction mixture was adjusted pH to 8 with Na₂CO₃ and concentrated. The product was dissolved out by THF, filtered and concentrated to afford compound I33-5 (2 g, 83% yield) as a white solid. MS Calcd.: 170; MS Found: 171 [M+H]⁺.

Step 5: Synthesis of I33-6

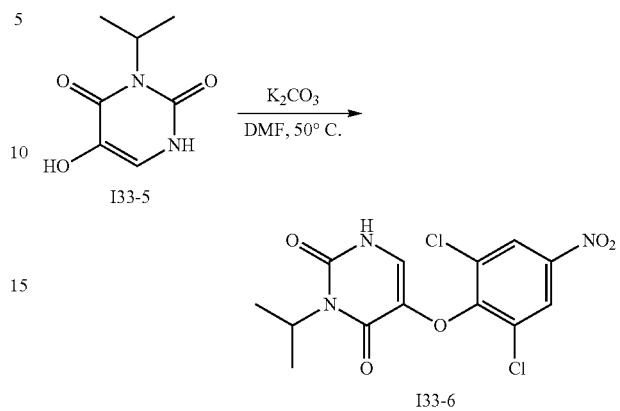

To a solution of compound I33-5 (1.6 mg, 9.41 mmol) in DMF (20 mL) was added 1,3-dichloro-2-fluoro-5-nitrobenzene (2 mg, 9.52 mmol) and K₂CO₃ (2.6 mg, 18.84 mmol). The resulting mixture was stirred at 50° C. for 2 hours. The reaction was diluted with H₂O (20 mL) and extracted with EA (30 mL×2). The combined organic layers were washed with brine (50 mL), dried over Na₂SO₄, filtered and concentrated. The residue was purified by flash chromatography on silica gel (DCM/MeOH=60/1) to afford compound I33-6 (1.5 g, 44% yield) as a white solid. MS Calcd.: 359; MS Found: 360 [M+H]⁺.

Step 6: Synthesis of I33-7

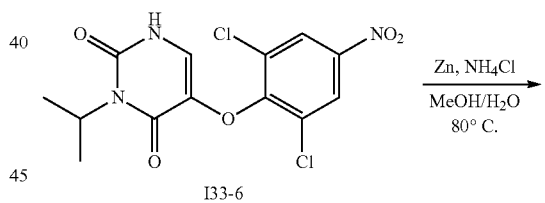

To a solution of compound I33-6 (1.1 mg, 3.06 mmol) in MeOH (10 mL) and water (1 mL) was added Zn (2 g, 30.70 mmol) and NH₄Cl (1.6 g, 30.19 mmol). The reaction mixture was stirred at 80° C. for 3 hours, then filtered and concentrated. The residue was purified by flash chromatography on silica gel (DCM/MeOH=30/1) to afford compound I33-7 (0.9 g, 90% yield) as a white solid. MS Calcd.: 329; MS Found: 330 [M+H]⁺.

Step 7: Synthesis of I33-8

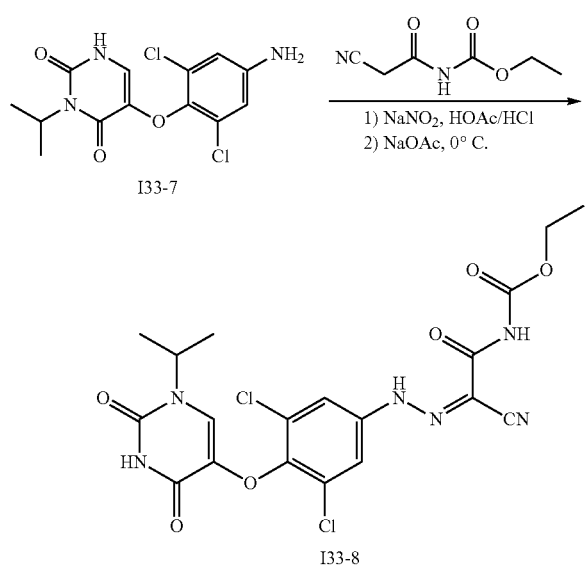

To a solution of compound I33-7 (500 mg, 1.52 mmol) in HOAc/HCl=12 mL/2 mL was added NaNO₂ (157 mg, 2.28 mmol) at 5-10° C. The reaction mixture was stirred at 5-10° C. for 30 minutes. Then ethyl (2-cyanoacetyl) carbamate (356 mg, 2.28 mmol) was added followed by a solution of NaOAc (374 mg, 4.56 mmol) in H₂O. The reaction mixture was stirred at 5-10° C. for 8 hours. The reaction was diluted with H₂O (20 mL) and extracted with DCM (30 mL×2). The combined organic layers were concentrated to afford compound I33-8 (700 mg, 93% yield) as a yellow solid. MS Calcd.: 496; MS Found: 497 [M+H]⁺.

Step 8: Synthesis of I33

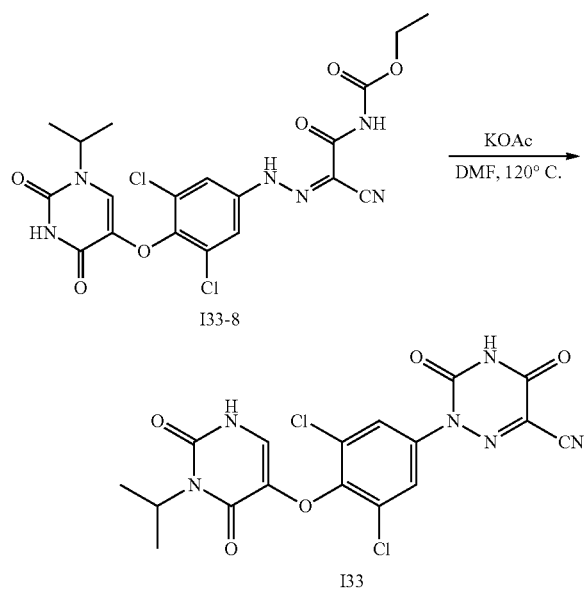

To a solution of compound I33-8 (700 mg, 1.41 mmol) in DMF (15 mL) was added KOAc (415 mg, 4.23 mmol). The reaction mixture was stirred at 120° C. for 3 hours. Then filtered and concentrated. The residue was purified by prep-HPLC to afford I33 (75.6 mg, 12% yield) as a white solid. ¹H NMR (400 MHZ, DMSO-d₆) δ: 13.24 (s, 1H), 10.98 (d, J=6.0 Hz, 1H), 7.67 (s, 2H), 7.39 (d, J=6.4 Hz, 1H), 5.00-4.97 (m, 1H), 1.37 (d, J=7.2 Hz, 6H). MS Calcd.: 450; MS Found: 451

Example 34

2-(3,5-dichloro-4-((1-(hydroxymethyl)-5-isopropyl-6-oxo-1,6-dihydropyridin-3-yl)oxy)phe nyl)-3,5-dioxo-2,3,4,5-tetrahydro-1,2,4-triazine-6-carbonitrile (I34)

Example 35

2-(3,5-dibromo-4-((5-isopropyl-6-oxo-1,6-dihydro-pyridin-3-yl)oxy)phenyl)-3,5-dioxo-2,3,4, 5-tetrahydro-1,2,4-triazine-6-carbonitrile (I35)

Example 36

2-(3,5-dichloro-4-((5-cyclobutyl-6-oxo-1,6-dihydro-pyridin-3-yl)oxy)phenyl)-3,5-dioxo-2,3,4, 5-tetrahydro-1,2,4-triazine-6-carbonitrile (I36)

Example 37

2-(3,5-dichloro-4-((3-isopropyl-1H-indol-5-yl)oxy) phenyl)-3,5-dioxo-2,3,4,5-tetrahydro-1,2, 4-triazine-6-carbonitrile (I37)

Example 38

2-(3,5-dichloro-4-((5-isopropyl-6-oxo-1,6-dihydro-pyridazin-3-yl)methyl)phenyl)-3,5-dioxo-2,3,4,5-tetrahydro-1,2,4-triazine-6-carbonitrile (I38)

Example 39

The biological properties of examples were investigated based on the following assay methods.
In Vitro Thyroid Hormone Receptor Binding Assay The interaction between the compounds of present invention and Human Thyroid Receptor (TR) are evaluated by Time-Resolved Fluorescence Resonance Energy Transfer (TR-FRET) competition assay. FRET describes a radiation-free energy transfer between two chromophores: a donor fluorophore in its excited state can transfer energy to an acceptor fluorophore in close proximity (typically <10 nm). In contrast to standard FRET, TR-FRET unites time-resolved fluorescence (TRF) and the FRET principle. TRF use a long-lifetime lanthanide chelate as the donor species, while lanthanide chelates are unique in that their excited-state lifetime can be on the order of a millisecond or longer. Suitable neighbors for FRET are known in the art and can be obtained. The assay was adopted from the manual of LanthaScreen™ TR-FRET Thyroid Receptor beta Coactivator Assay kit from Invitrogen.

The assay is performed in following steps: first, prepare reaction buffer containing 50mMTris-HCl (pH7.4) with 100 mM NaCl, 1mMEDTA, 50mMKF, 1mMDTT, 1mMMgCl₂, 10% glycerol, 0.01% NP-40, 0.1% BSA. Second, use the buffer to prepare the appropriate dilution series of the test and reference compounds. The3,3',5-Triiodothyronine (T3) was used aspositive control agonist. Third, add 5 μl of 4× compound serial dilution and 5 µl TRa LBD (4×, 4 nM) (or 5 µl TRβ LBD, 4×, 2 nM) into 384-well plate (784075, greiner). Then, add 10 µl of a solution consist of 400 nM Biotin-SRC2-2 (2×) and anti-GST Eu (1:200, 2×) and 50 nM anti-biotin-d2 (2×) in 1× reaction buffer to initiate the reaction. Centrifuge the plates at 1000 g for 1 min and then incubate 1 hour at room temperature protected from light. Finally, read the plate at wavelengths of 665 nm and 615nm on Envision2104 plate reader.

A ratio ($Ratio_{665\ nm/615\ nm}-Ratio_{background}$) is calculated for each well. Percentage of activity, as well as $EC_{50}$ was calculated. Effect-dose curve was plotted. Relative selectivity was calculated as the ratio of $EC_{50}TR\alpha/EC_{50}TR\beta$.

The following results were obtained:

| | $EC_{50}$(µM) | | Relative Selectivity |
|---|---|---|---|
| | TR-α | TR-β | TR-α/TR-β |
| MGL3196 | 7.546000 | 0.235600 | 10.81 |
| I4 | 3.599000 | 0.440800 | 8.165 |
| I1 | 0.006765 | 0.017280 | 0.3915 |
| I2 | 0.007365 | 0.016150 | 0.4560 |
| I3 | 3.138000 | 0.277000 | 11.51 |
| I5 | >10 | >10 | NA |
| I6 | >10 | 1.981 | >5.05 |
| I7 | >10 | >10 | NA |
| I8 | >10 | 2.892 | >3.46 |
| I9 | >10 | >10 | NA |
| I10 | NA | NA | NA |
| I11 | >10 | 0.754 | NA |
| I12 | 2.286 | 0194 | 1176 |
| I13 | 12.210 | 2.612 | 4.67 |
| I14 | 0.172 | 0.046 | 3.70 |
| I15 | 1.786 | 0.854 | 2.09 |
| I16 | 0.532 | 0.125 | 4.25 |
| I17 | 1.015 | 0.135 | 7.50 |
| I18 | NA | NA | NA |
| I19 | 0.024 | 0.006 | 3.83 |
| I20 | 8.374 | 2.088 | 4.01 |
| I21 | 1.042 | 0.086 | 12.11 |
| I22 | NA | NA | NA |
| I23 | NA | NA | NA |
| I24 | >100 | 0.273 | 366 |
| I25 | NA | NA | NA |
| I26 | NA | NA | NA |
| I27 | 6.406 | 2.265 | 2.83 |
| I28 | >100 | >10 | NA |
| I29 | 5.231 | 6.395 | 0.82 |
| I30 | >100 | >10 | NA |
| I31 | >100 | >10 | NA |
| I32 | >100 | >10 | NA |
| I33 | >100 | >10 | NA |
| I34 | NA | NA | NA |
| I35 | NA | NA | NA |
| I36 | NA | NA | NA |
| I37 | NA | NA | NA |
| I38 | 0.578 | 0.038 | 14.85 |

In Vitro Thyroid Hormone Transactivation Assay

TRα-LBD (or TRβ-LBD) and RXRα-LBD, coding sequence were inserted into the pBIND expression vector (Promega, E1581) respectively to express TRα-GAL4 (or TRβ-GAL4) and RXRα-GAL4 chimeric receptors. The two expression vectors and reporter vector (pGL4.35 which carry a stably integrated GAL4 promoter driven luciferase reporter gene) were co-transfected into HEK293T host cells. Upon agonist binding to the corresponding TRα-GAL4 (or TRβ-GAL4) chimeric receptor, the chimeric receptor binds to the GAL4 binding sites and stimulates the reporter gene. The ability of test compound to stimulate TRα (or TRβ) transactivation activity was determined, respectively.

The assay is performed in following steps: first, prepare compound stock solution be serial dilution with DMSO. Second, seed $2.5\times10^6$ HEK293T cells into a 60 mm dish and incubated at 37° C., 5% $CO_2$ for 16 hours. Third, cell transfection was performed by mixing DNA and Lipo LTX reagent in Opti-MEM™ medium, as well as 2.5 µg TRβ (or 2.5 µg TRα) plasmid/2.5 µg RXRα plasmid/1 µg pGL4.35 luciferase plasmid and incubating for 4-7 hours at 37° C., 5% $CO_2$. Fourth, the prepared cells were seeded at 17,000 cells/well and the diluted compound solutions was added. The cells were incubated for 16-20 hours at 37° C., 5% $CO_2$. Finally, add 25 µl of Luciferase Detection Reagent (LDT) to the assay plate at room temperature. Shake the plate at room temperature for at least 5 min, and then read the luminescence value on Evision 2104 plate reader. Calculate $EC_{50}$ by fitting % Inhibition values and log of compound concentrations to nonlinear regression (dose response-variable slope) with Graphpad 5.0. In the test of this invention, the Z'-factors show >0.5.

The following results were obtained:

| | $EC_{50}$(µM) | |
|---|---|---|
| | TR-α | TR-β |
| MGL3196 | >10 | 1.9740 |
| I4 | >10 | 6.0940 |
| I1 | NA | NA |
| I2 | NA | NA |
| I3 | >10 | 2.0650 |
| I5 | NA | NA |
| I6 | NA | NA |
| I7 | NA | NA |
| I8 | NA | NA |
| I9 | NA | NA |
| I10 | >10 | >10 |
| I12 | 7.3700 | 12660 |

It is to be understood that the invention is not limited to the particular embodiments of the invention described above, as variations of the particular embodiments may be made and still fall within the scope of the appended claims.

What is claimed is:

1. A compound of Formula (I) or (Ia), or a tautomer or a pharmaceutically acceptable salt thereof,

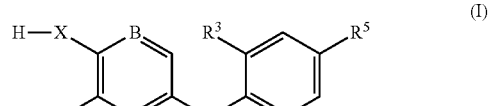

(I)

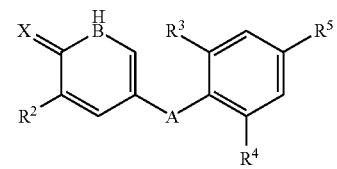

(Ia)

Wherein:
A is O or $CH_2$;
B is N or CH;
X is O or $NR^1$ or $CHR^1$:
$R^1$ is selected from bond or H or lower alkyl;
$R^2$ is H or lower alkyl;
or $R^1$ and $R^2$ together with the X—C=C to which they are connected form a 5- to 9-membered carbon or hetero cycle, the hetero cycle is non-substituted or substituted by $R^6$ and $R^7$, $R^6$ and $R^7$ are independently selected from the group H or lower alkyl;

$R^3$ and $R^4$ are independently selected from the group consisting of H, F, Cl, Br and $CH_3$;

$R^5$ is selected from the group consisting of:

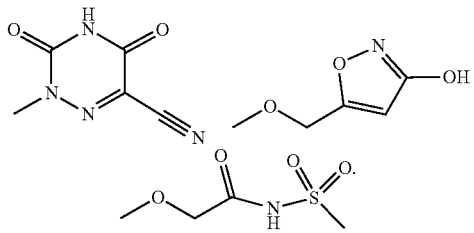

2. The compound of claim 1, wherein B is CH, A is $CH_2$.
3. The compound of claim 1, wherein A is O, B is CH.
4. The compound of claim 3, wherein $R^5$ is

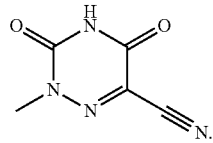

5. The compound of claim 4, wherein X is $NR^1$ or $CHR^1$, $R^1$ and $R^2$ together with the X—C=C to which they are connected form a 5-membered hetero cycle which is

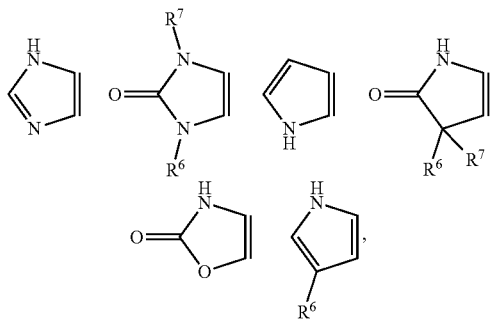

$R^6$ and $R^7$ are independently selected from the group H or Me.

6. The compound of claim 1, wherein B is N.
7. The compound of claim 6, wherein $R^5$ is

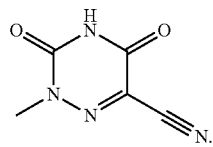

8. The compound of claim 7, wherein A is $CH_2$, X is O.
9. The compound of claim 7, wherein A is O, X is O.
10. The compound of claim 1, selected from one of the following structures:

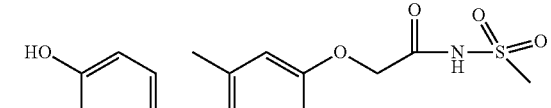
I1

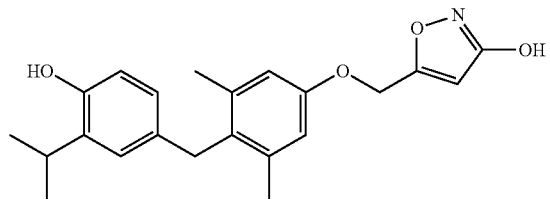
I2

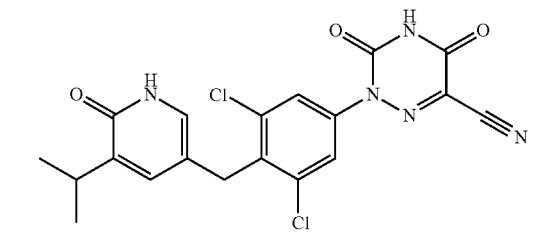
I3

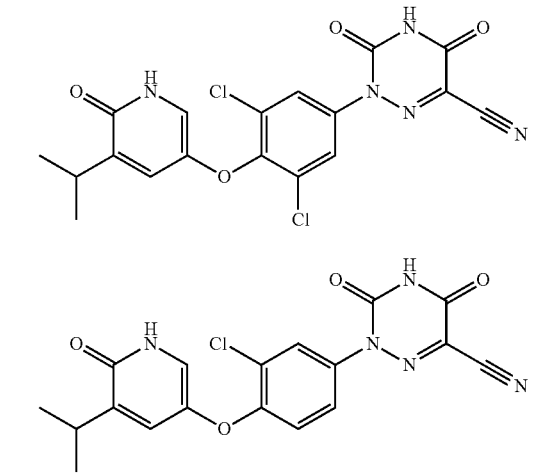

I4

I5

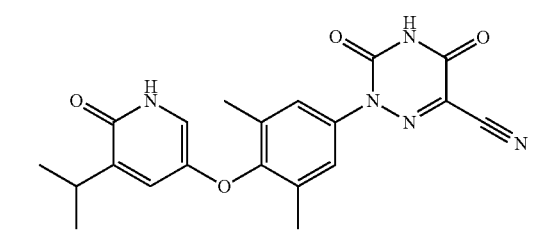
I6

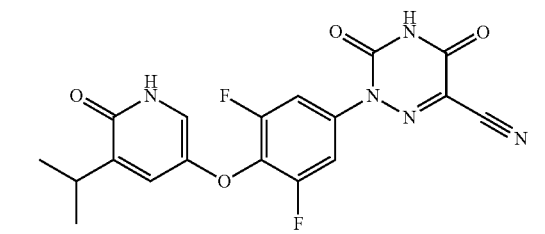
I7

I8
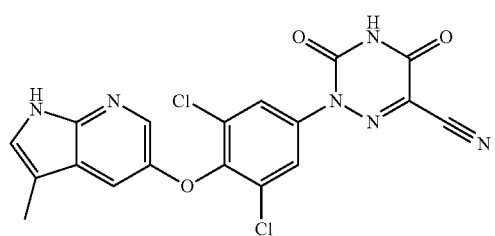
I9
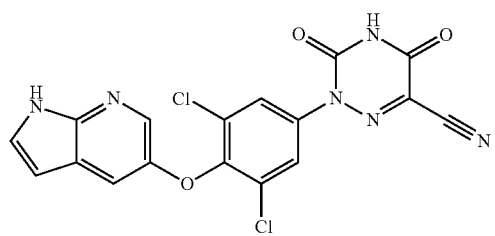
I10
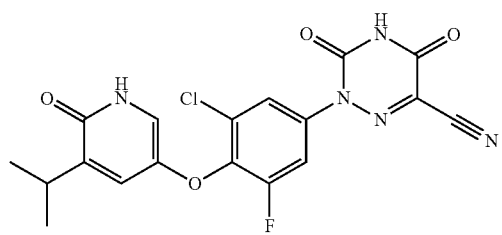
I11
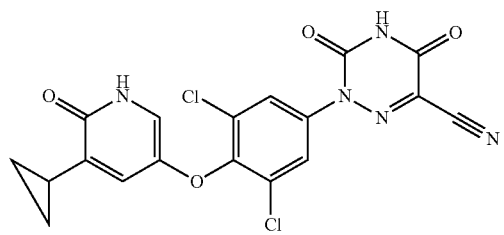
I12
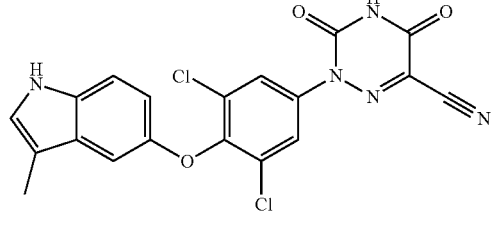
I13
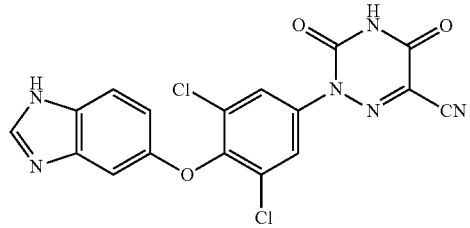
I14
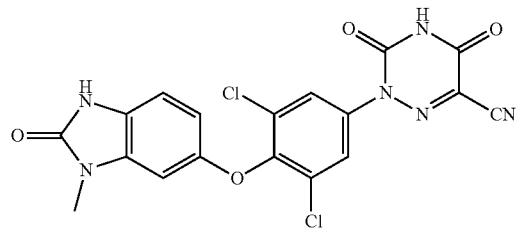
I15
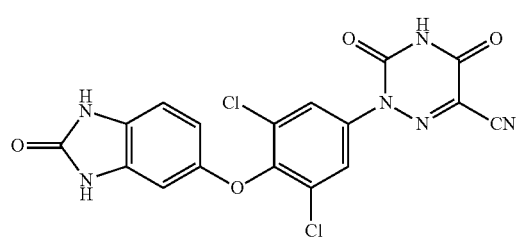
I16
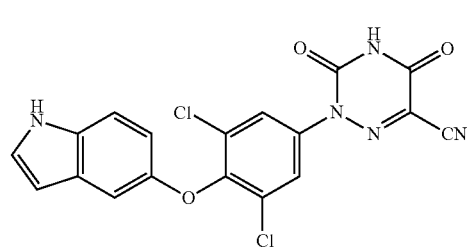
I17
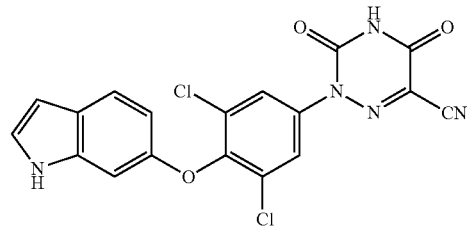
I18
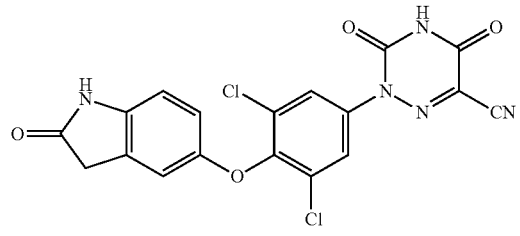
I19
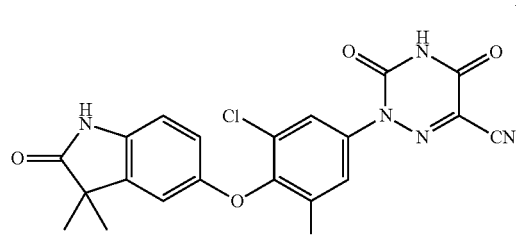

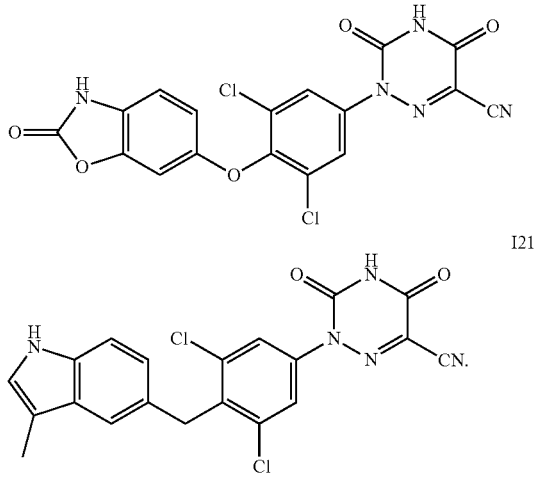

11. Pharmaceutical compositions comprising a compound according to claim 1 and a pharmaceutically acceptable carrier and/or adjuvant.

12. A method for the therapeutic and/or prophylactic treatment of diseases which are modulated by thyroid hormone analogs comprising administering a compound according to claim 1 to a human being or animal.

13. The method of claim 12, wherein the diseases which are modulated by thyroid hormone analogs are metabolic diseases.

14. The method of claim 12, wherein the diseases which are modulated by thyroid hormone analogs are obesity, hyperlipidemia, hypercholesterolemia, diabetes, nonalcoholic steatohepatitis, atherosclerosis, cardiovascular diseases, hypothyroidism, or thyroid cancer.

* * * * *